(12) United States Patent
Lesieur et al.

(10) Patent No.: US 7,126,012 B2
(45) Date of Patent: *Oct. 24, 2006

(54) SUBSTITUTED CYCLIC COMPOUNDS

(75) Inventors: Daniel Lesieur, Gondecourt (FR);
Frederique Klupsch, Hulluch (FR);
Gerald Guillaumet, Saint Jean le Blanc
(FR); Marie-Claude Viaud, Tours
(FR); Michel Langlois, Sceaux (FR);
Caroline Bennejean, Charenton le Pont
(FR); Pierre Renaud, Le Chesnay
(FR); Philippe Delagrange, Issy les
Moulineaux (FR)

(73) Assignee: Les Laboratoires Servier, Courbevoie
Cedex (FR)

( * ) Notice: Subject to any disclaimer, the term of this
patent is extended or adjusted under 35
U.S.C. 154(b) by 0 days.

This patent is subject to a terminal disclaimer.

(21) Appl. No.: 10/947,757

(22) Filed: Sep. 23, 2004

(65) Prior Publication Data

US 2005/0059729 A1   Mar. 17, 2005

Related U.S. Application Data

(62) Division of application No. 09/700,098, filed as application No. PCT/FR99/01100 on May 10, 1999, now Pat. No. 6,872,851.

(30) Foreign Application Priority Data

May 12, 1998   (FR) ................... 98 05957

(51) Int. Cl.
C07D 333/52   (2006.01)
A61K 31/385   (2006.01)
C07C 233/05   (2006.01)
A61K 31/165   (2006.01)

(52) U.S. Cl. .................. 549/55; 549/57; 549/466; 549/467; 549/468; 514/433; 514/469; 514/470

(58) Field of Classification Search .......... 549/55, 549/57, 466, 467, 468; 514/433, 469, 470
See application file for complete search history.

(56) References Cited

U.S. PATENT DOCUMENTS 5,350,748 A *  9/1994  Boschelli et al. ........ 514/237.2
8,605,632       8/2003  Lesieur et al. ............ 514/411

FOREIGN PATENT DOCUMENTS

| EP | 0 530 087 | 3/1993 |
| EP | 0 562 956 | 9/1993 |
| EP | 0 662 471 | 7/1995 |
| EP | 0 728 738 | 8/1996 |
| EP | 0 745 583 | 12/1996 |
| EP | 0 745 584 | 12/1996 |

* cited by examiner

*Primary Examiner*—Shailendra Kumar
(74) *Attorney, Agent, or Firm*—Hueschen and Sage

(57) ABSTRACT

The invention concerns compounds of formula (I): R-A-R' wherein: A is as defined in the description; R represents a group (V), (VI), (VII) or (VIII), where E, Q, $R^1$, $R^2$, $R^3$, v and $R^4$ are as defined in the description; R' represents a —$(CH^2)t$-$R^5$ group wherein t and $R^5$ are as defined in the description

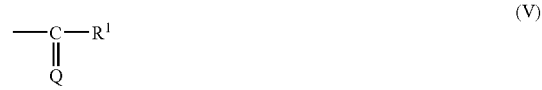

(V)

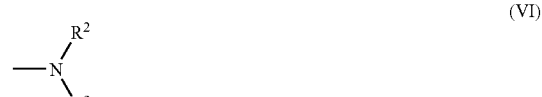

(VI)

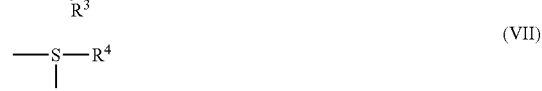

(VII)

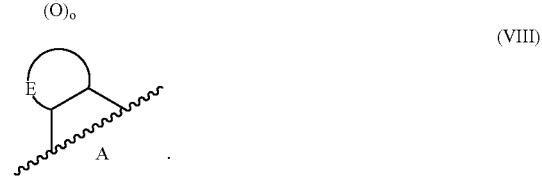

(VIII)

24 Claims, No Drawings

SUBSTITUTED CYCLIC COMPOUNDS

This application is a DIV of Ser. No. 09/700,098, filed Nov. 10, 2000, now U.S. Pat. No. 6,872,851; which is a 371 of PCT/FR99/01100, filed May 10, 1999.

FIELD OF THE INVENTION

The present invention relates to new substituted cyclic compounds having very valuable pharmacological characteristics in respect of melatoninergic receptors.

DESCRIPTION OF THE PRIOR ART

The prior art discloses thio-substituted indole amides for use as anti-inflammatory agents (EP 624575, EP 535923), as antagonists of the release of gonadotrophin (WO 9721703), as 5HT-2B or 2C antagonists (WO 9602537), or as synthesis intermediates (Akad. Nauk Gruz., 1991, 141 (3), pp. 545–8; Pept. Chem., 1993, 31, pp. 33–6, J. Pharm. Sci., 1973, 62 (8), pp. 1374–5).

Benzo[b]thiophene compounds have also been described as anti-inflammatory agents (U.S. Pat. No. 5,350,748, U.S. Pat. No. 5,068,248) or as anti-cancer agents (Heterocycles, 1985, 23 (5), pp. 1173–80).

BACKGROUND OF THE INVENTION

In the last ten years, numerous studies have demonstrated the major role played by melatonin (5-methoxy-N-acetyl-tryptamine) in numerous physiopathological phenomena and also in the control of circadian rhythm. Its half-life is, however, quite short owing to its being rapidly metabolised. It is thus very useful to be able to provide the clinician with melatonin analogues that are metabolically more stable and that have an agonist or antagonist character on the basis of which a therapeutic effect that is superior to that of the hormone itself may be expected.

In addition to their beneficial action on disorders of circadian rhythm (J. Neurosurg. 1985, 63, pp 321–341) and sleep disorders (Psychopharmacology, 1990, 100, pp 222–226), ligands of the melatoninergic system have valuable pharmacological properties in respect of the central nervous system, especially anxiolytic and antipsychotic properties (Neuropharmacology of Pineal Secretions, 1990, 8 (3–4), pp 264–272) and analgesic properties (Pharmacopsychiat., 1987, 20, pp 222–223), and also for the treatment of Parkinson's disease (J. Neurosurg. 1985, 63, pp 321–341) and Alzheimer's disease (Brain Research, 1990, 528, pp 170–174). Those compounds have also shown activity on certain cancers (Melatonin—Clinical Perspectives, Oxford University Press, 1988, pp 164–165), ovulation (Science 1987, 227, pp 714–720), diabetes (Clinical Endocrinology, 1986, 24, pp 359–364), and in the treatment of obesity (International Journal of Eating Disorders, 1996, 20 (4), pp 443–446).

Those various effects take place via the intermediary of specific melatonin receptors. Molecular biology studies have shown the existence of a number of receptor sub-types that can bind the hormone (Trends Pharmacol. Sci., 1995, 16, p 50; WO 97.04094). It has been possible to locate some of those receptors and to characterise them for different species, including mammals. In order to be able to understand the physiological functions of those receptors better, it is very valuable to have specific ligands available. Moreover, by interacting selectively with one or other of those receptors, such compounds can be excellent medicaments for the clinician in the treatment of pathologies associated with the melatoninergic system, some of which have been mentioned above.

In addition to the fact that the compounds of the present invention are new, they exhibit very great affinity for melatonin receptors and/or selectivity for one or other of the melatoninergic receptor sub-types.

DETAILED DESCRIPTION OF THE INVENTION

More specifically, the present invention relates to compounds of formula (I):

R-A-R'  (I)

wherein:

A represents:
  a ring system of formula (II):

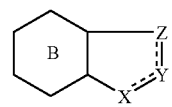

wherein

X represents an oxygen, sulphur or nitrogen atom or a group $C(H)_q$ (wherein q is 0, 1 or 2) or $NR_0$ (wherein $R_0$ represents a hydrogen atom, a linear or branched $(C_1-C_6)$alkyl group, an aryl group, an aryl-$(C_1-C_6)$alkyl group in which the alkyl moiety is linear or branched, or $SO_2Ph$), Y represents a nitrogen atom or a group $C(H)_q$ (wherein q is 0, 1 or 2), Z represents a nitrogen atom or a group $C(H)_q$ (wherein q is 0, 1 or 2), but X, Y and Z cannot represent three hetero atoms simultaneously, B represents a benzene or pyridine nucleus, the symbol  means that the bonds may be single or double, it being understood that the valency of the atoms is respected, wherein R substitutes the ring B and R' substitutes the ring containing the groups X, Y and Z, or R and R' substitute the ring B, a ring system of formula (III):

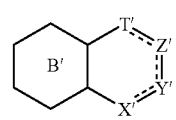

wherein

X' represents an oxygen or sulphur atom or a group $C(H)_q$ (wherein q is 0, 1 or 2), Y' represents a group $C(H)_q$ (wherein q is 0, 1 or 2) or $NR_0$ wherein $R_0$ is as defined hereinbefore, Z' represents a group $C(H)_q$ (wherein q is 0, 1 or 2) or $NR_0$ wherein $R_0$ is as defined hereinbefore, T' represents an oxygen or sulphur atom or a group $C(H)_q$ (wherein q is 0, 1 or 2), it being understood that, when Y' or Z' represents a hetero atom, the other three variables ((X', Z', T') and (X', Y', T'), respectively) cannot represent a hetero atom, the symbol ⁓⁓⁓⁓ is as defined hereinbefore, B' represents:
- a benzene nucleus,
- a naphthalene nucleus when X', Y', Z' and T' do not simultaneously represent a group $C(H)_q$ (wherein q is 0, 1 or 2),
- or a pyridine nucleus when X' and T' simultaneously represent a group $C(H)_q$ (wherein q is 0, 1 or 2), wherein R substitutes the ring B' and R' substitutes the ring containing the groups X', Y', Z' and T', or R and R' substitute the ring B', a ring system of formula (IV):

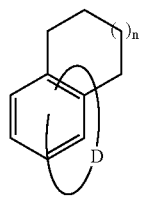
(IV)

representing the ring systems $(IV_{a-d})$:

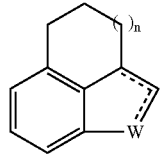
$(IV_a)$

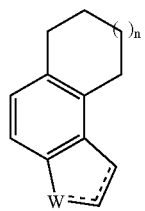
$(IV_b)$

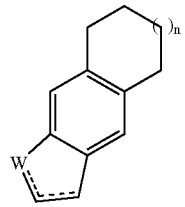
$(IV_c)$

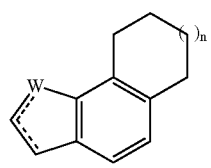
$(IV_d)$ wherein
n is an integer such that $0 \leq n \leq 3$,
W represents an oxygen, sulphur or nitrogen atom, or a group $[C(H)_q]_p$ (wherein q is 0, 1 or 2, and p is 1 or 2) or $NR_0$ wherein $R_0$ is as defined hereinbefore, the symbol ⁓⁓⁓⁓ is as defined hereinbefore, wherein R' substitutes the ring

and R substitutes one or other of the two other rings,
or a biphenyl group wherein R substitutes one of the benzene rings and R' substitutes the other, or R and R' substitute the same benzene ring, it being understood that the ring systems of formulae (II), (III) and (IV) and the biphenyl group may be unsubstituted or substituted (in addition to the substituents R and R') by from 1 to 6 radicals, which may be the same or different, selected from $R_a$, $OR_a$, $COR_a$, $COOR_a$, $OCOR_a$, $OSO_2CF_3$, cyano, nitro and halogen atoms, wherein $R_a$ represents a hydrogen atom, an unsubstituted or substituted linear or branched ($C_1$–$C_6$)alkyl group, an unsubstituted or substituted linear or branched ($C_2$–$C_6$)alkenyl group, an unsubstituted or substituted linear or branched ($C_2$–$C_6$)alkynyl group, a linear or branched ($C_1$–$C_6$)polyhaloalkyl group, an unsubstituted or substituted ($C_3$–$C_8$)cycloalkyl group, an unsubstituted or substituted ($C_3$–$C_8$)cycloalkyl-($C_1$–$C_6$)alkyl group in which the alkyl group is linear or branched, an unsubstituted or substituted ($C_3$–$C_8$)cycloalkenyl group, an unsubstituted or substituted ($C_3$–$C_8$)cycloalkenyl-($C_1$–$C_6$) alkyl group in which the alkyl group is linear or branched, an aryl group, an aryl-($C_1$–$C_6$)alkyl group in which the alkyl moiety is linear or branched, an aryl-($C_1$–$C_6$)alkenyl group in which the alkenyl moiety is linear or branched, a heteroaryl group, a heteroaryl-($C_1$–$C_6$)alkyl group in which the alkyl moiety is linear or branched, a heteroaryl-($C_1$–$C_6$) alkenyl group in which the alkenyl moiety is linear or branched, an unsubstituted or substituted linear or branched ($C_1$–$C_6$)heterocycloalkyl group, an unsubstituted or substituted heterocycloalkenyl group, a substituted or unsubstituted heterocycloalkyl-($C_1$–$C_6$)alkyl group in which the alkyl moiety is linear or branched, or a substituted or unsubstituted heterocycloalkenyl-($C_1$–$C_6$)alkyl group in which the alkyl moiety is linear or branched, R represents:
a group of formula (V):

(V)

wherein r is an integer such that $0 \leq r \leq 2$,

R¹ represents a halogen atom, a group $R_a$, $OR_a$, $COR_a$ or $COOR_a$, wherein $R_a$ is as defined hereinbefore, it being understood that R cannot represent a group SO₃H, a group —NR′$_a$R″$_a$ wherein R′$_a$ and R″$_a$, which may be the same or different, may take any of the values of $R_a$ and also may form, together with the nitrogen atom carrying them, a 5- to 10-membered cyclic group which may contain, in addition to the nitrogen atom, from one to three hetero atoms selected from oxygen, sulphur and nitrogen, or, when A represents a ring system of formula (II) or (III) or a biphenyl group, forms, together with two adjacent carbon atoms of the ring structure A carrying it, a ring of formula (VI):

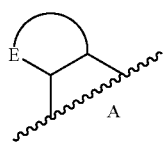

(VI)

wherein E represents a group

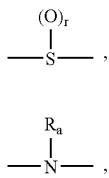

wherein r and $R_a$ are as defined hereinbefore, the ring formed containing from 5 to 7 atoms and it being possible for the said ring to contain from 1 to 3 hetero atoms selected from nitrogen, sulphur and oxygen, and one or more unsaturations, and being optionally substituted by one or more radicals, which may be the same or different, selected from $R_a$, $OR_a$, $COR_a$, $COOR_a$, $OCOR_a$, NR′$_a$R″$_a$, $NR_a$COR′$_a$, CONR′$_a$R″$_a$, cyano, oxo, $SR_a$, $S(O)R_a$, $SO_2R_a$, $CSR_a$, $NR_a$CSR′$_a$, CSNR′$_a$R″$_a$, $NR_a$CONR′$_a$R″$_a$, $NR_a$CSNR′$_a$R″$_a$ and halogen atoms, wherein $R_a$, R′$_a$ and R″$_a$, which may be the same or different, may take any of the values of $R_a$ and R′$_a$ and R″$_a$ may also form, together with the nitrogen atom carrying them, a cyclic group as defined hereinbefore, and R′ represents a group of formula (VII):

-G-R²  (VII)

wherein

G represents an alkylene chain —(CH₂)$_t$— (wherein t is an integer such that $0 \leq t \leq 4$), optionally substituted by one or more radicals, which may be the same or different, selected from $R_a$, $OR_a$, $COOR_a$, $COR_a$ (wherein $R_a$ is as defined hereinbefore) and halogen atoms, and R² represents a group

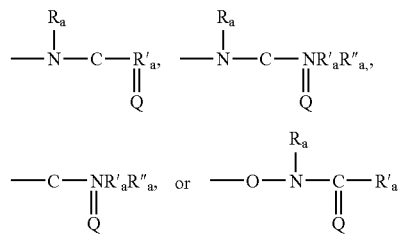

wherein Q is oxygen or sulfur, $R_a$, R′$_a$, and R″$_a$ (which may be the same or different) are as defined hereinbefore, it being possible for R′$_a$ and R″$_a$ to form, together with the nitrogen atom carrying them, a cyclic group as defined hereinbefore, it being understood that:

"heterocycloalkyl" is taken to mean any saturated mono- or poly-cyclic group containing from 5 to 10 atoms containing from 1 to 3 hetero atoms selected from nitrogen, oxygen and sulphur, "heterocycloalkenyl" is taken to mean any non-aromatic mono- or poly-cyclic group containing one or more unsaturations, containing from 5 to 10 atoms and which may contain from 1 to 3 hetero atoms selected from nitrogen, oxygen and sulphur, the term "substituted" used in respect of the expressions "alkyl", "alkenyl" and "alkynyl" indicates that the groups in question are substituted by one or more radicals, which may be the same or different, selected from hydroxy, linear or branched $(C_1$–$C_6)$ alkoxy, linear or branched $(C_1$–$C_6)$alkyl, linear or branched $(C_1$–$C_6)$polyhaloalkyl, amino and halogen atoms, the term "substituted" used in respect of the expressions "cycloalkyl", "cycloalkylalkyl", "cycloalkenyl", "cycloalkenylalkyl", "heterocycloalkyl", "heterocycloalkenyl", "heterocycloalkylalkyl" and "heterocycloalkenylalkyl" indicates that the cyclic moiety of the groups in question is substituted by one or more radicals, which may be the same or different, selected from hydroxy, linear or branched $(C_1$–$C_6)$ alkoxy, linear or branched $(C_1$–$C_6)$alkyl, linear or branched $(C_1$–$C_6)$polyhaloalkyl, amino and halogen atoms, "aryl" is taken to mean any aromatic, mono- or poly-cyclic group containing from 6 to 22 carbon atoms, and also the biphenyl group, "heteroaryl" is taken to mean any aromatic mono- or poly-cyclic group containing from 5 to 10 atoms containing from 1 to 3 hetero atoms selected from nitrogen, oxygen and sulphur, it being possible for the "aryl" and "heteroaryl" groups to be substituted by one or more radicals, which may be the same or different, selected from hydroxy, linear or branched $(C_1$–$C_6)$alkoxy, linear or branched $(C_1$–$C_6)$ alkyl, linear or branched $(C_1$–$C_6)$polyhaloalkyl, cyano, nitro, amino and halogen atoms, it being understood that:

when A represents a ring system of formula (IIa):

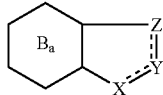
(IIa)

wherein X, Y, Z and the symbol ----- are as defined hereinbefore, Ba represents a benzene nucleus and R represents a group of formula (V), then R' cannot represent a group G-R² wherein G represents a single bond (t=0) and R² represents a group —CONR'$_a$R"$_a$ wherein R'$_a$ and R"$_a$ are as defined hereinbefore, when A represents a naphthalene nucleus and R represents a group of formula (V), then R' cannot represent a group G-R wherein G represents a single bond (t=0) and R² represents a group —NHCOR$_b$ wherein R$_b$ represents a group (C$_1$–C$_4$)alkyl or phenol optionally substituted, when A represents 1-naphthol and R represents a group of formula (V), then R' cannot represent a group G-R² wherein G represents a single bond (t=0) and R² represents a group —CONHR$_c$ wherein R$_c$ represents an optionally substituted phenyl group, when A represents a tetrahydronaphthalene nucleus and R represents a group of formula (V), then R' cannot represent a group G-R² wherein G represents a single bond (t=0) and R² represents a group —NR$_a$COR$_d$ wherein R$_d$ represents a (C$_3$–C$_8$)cycloalkyl group, when A represents an indole nucleus substituted in the 2-position by an optionally substituted phenyl group, then R² cannot represent a group —NHCOR$_e$ wherein R$_e$ is a group containing an aromatic or non-aromatic mono- or bi-cyclic heterocycle, the compound of formula (I) cannot represent:
N-{2-[4-methylthio]-1H-3-indolyl]ethyl}formamide
2-(acetylamino)-3-{7-[(2-hydroxyethyl)thio]-1H-3-indolyl}propanamide
2-(acetylamino)-3-{2,7-di[(2-hydroxyethyl)thio]-1H-3-indolyl}propanamide, their enantiomers and diastereoisomers, and addition salts thereof with a pharmaceutically acceptable acid or base.

Among the pharmaceutically acceptable acids there may mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid etc.

Among the pharmaceutically acceptable bases there may mentioned, without implying any limitation, sodium hydroxide, potassium hydroxide, triethylamine, tert-butylamine etc.

Preferred compounds of the invention are those wherein A represents a ring system of formula (II) or (III) and, more especially, of formula (II'):

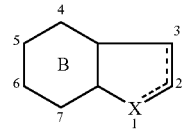
(II')

wherein B, X and the symbol ----- are as defined hereinbefore,
or of formula (III'):

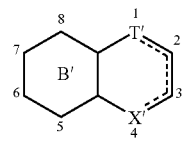
(III')

wherein B', T', X' and the symbol ----- are as defined hereinbefore.

The invention advantageously relates to compounds wherein A, which is unsubstituted or substituted by a single substituent (in addition to R and R') preferably in the 2-position (formula II') or in the 3-position (formula III'), represents a ring system of formula (II'):

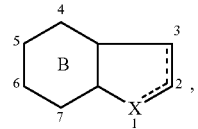
(II')

wherein B, X and the symbol ----- are as defined hereinbefore, such as, for example, benzothiophene, dihydrobenzothiophene, benzofuran, dihydrobenzofuran, indole, indoline, indan, indene, azaindole, thienopyridine or furopyridine, or of formula (III'):

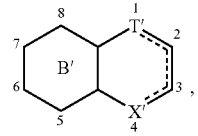
(III')

wherein B', T', X' and the symbol ----- are as defined hereinbefore, such as, for example, naphthalene, tetrahydronaphthalene, (thio)chroman, (dihydro)benzodioxin, (dihydro)benzoxathiin, (dihydro)benzochromene.

Even more advantageously, the invention relates to compounds wherein A of formula (II') or (III') is substituted by R in the 5-position (formula II') or 7-position (formula III') and by R' in the 3-position (formula II') or 1- or 2-position (formula III').

Preferred substituents R of the invention are those represented by a group of formula (V), (VI) or —NR'$_a$R"$_a$ (wherein R'$_a$ and R"$_a$ are as defined hereinbefore).

More advantageously, preferred substituents R of the invention are those represented by a group of formula (V) (wherein r is 0 and $R^1$ represents a group $R_a$ as defined hereinbefore), a group $NR'_aR''_a$ (wherein $R'_a$ and $R''_a$ are as defined hereinbefore), or a group of formula (VI) wherein E represents a group

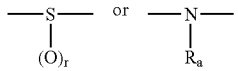

wherein r and $R_a$ are as defined hereinbefore.

Even more advantageously, preferred substituents R of the invention are those represented by a group of formula (V) wherein r is 0 and $R^1$ represents an alkyl, polyhaloalkyl, alkenyl, alkynyl, cycloalkyl, cycloalkenyl, cycloalkylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, or a group $NR'_aR''_a$, wherein $R'_a$ and $R''_a$ (which may be the same or different) represent a hydrogen atom, an alkyl, polyhaloalkyl, alkenyl, alkynyl, cycloalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, or form, together with the nitrogen atom carrying them, a piperazine, piperidine, morpholine or thiomorpholine group.

Preferred substituents R' of the invention are those wherein G represents an unsubstituted or substituted alkylene chain $—(CH_2)_t—$, wherein t is 2 or 3, and $R^2$ represents a group

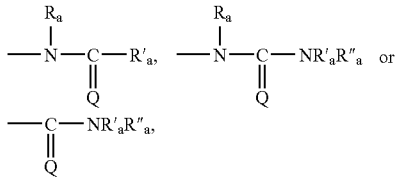

wherein $R_a$, $R'_a$ and $R''_a$ are as defined hereinbefore.

Even more advantageously, preferred substituents R' of the invention are those wherein G represents a group $—(CH_2)_t—$, wherein t is 2 or 3, and $R^2$ represents a group

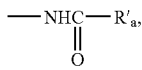

wherein $R'_a$ represents an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, or G represents a group $—(CH_2)_3—$ and $R^2$ represents a group

wherein $R_a$ represents an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl.

More especially, preferred compounds of the invention are those wherein A represents a ring system of formula (II') or (III') and R represents a group of formula (V), (VI) or $—NR'_aR''_a$.

More advantageously, the invention relates to compounds wherein:

A represents a group of formula (II') or (III') substituted in the 5-position (formula II') or 7-position (formula III') by R and in the 3-position (formula II') or 1- or 2-position (formula III') by R', and R represents a group $SR_a$, $NR'_aR''_a$ (wherein $R'_a$ and $R''_a$ are as defined hereinbefore) or a group of formula (VI) wherein E represents a group

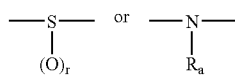

wherein r and $R_a$ are as defined hereinbefore.

Even more advantageously, preferred compounds of the invention are those wherein A represents a ring system of formula (II') or (III') optionally substituted (in addition to R and R') by a substituent in the 2-position (formula II') or 3-position (formula III'), substituted in the 5-position (formula II') or 7-position (formula III') by R and in the 3-position (formula II') or 1- or 2-position (formula III') by R', R represents a group $—SR_a$, $NR'_aR''_a$ (wherein $R_a'$ and $R''_a$ are as defined hereinbefore), or a group of formula (VI) wherein E represents a group

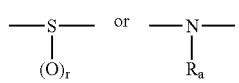

wherein r and $R_a$ are as defined hereinbefore, and R' is such that G represents an unsubstituted or substituted alkylene chain $—(CH_2)_t—$, wherein t is 2 or 3, and $R^2$ represents a group

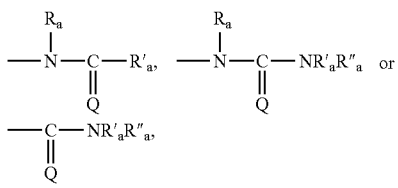

wherein $R_a$, $R'_a$ and $R''_a$ are as defined hereinbefore.

Even more especially, the invention relates to (dihydro)benzothiophenes, (dihydro)benzofurans, indoles, indolines, indenes, indans, azaindoles, thieno- or furopyridines optionally substituted in the 2-position, and to dihydronaphthalenes, tetrahydronaphthalenes, naphthalenes or chromans optionally substituted in the 3-position, substituted in the 5-position (or 7-position, respectively) by a group —$SR_a$ or —$NR'_a R''_a$ wherein $R'_a$ and $R''_a$, which may be the same or different, represent a hydrogen atom, an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, or R'a and R''a form, together with the nitrogen atom carrying them, a piperazine, piperidine, morpholine or thiomorpholine group, and substituted in the 3-position (or 1- or 2-position, respectively) by a group —$(CH_2)_t$—$NHCOR'_a$ wherein t is 2 or 3 and $R'_a$ represents an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl.

Even more advantageously, preferred compounds of the invention are naphthalenes, optionally substituted in the 3-postion, substituted in the 7-position by a thioalkyl group such as, for example, thiomethyl, thioethyl, thiopropyl, and substituted in the 1-position by a group —$(CH_2)_t$—$NHCOR'_a$ wherein t is 2 or 3 and $R'_a$ represents an alkyl, polyhaloalkyl or cycloalkyl group, such as, for example, methyl, ethyl, propyl, trifluoromethyl, cyclopropyl, cyclobutyl, cyclopentyl, cyclohexyl.

The invention relates very particularly to the compounds of formula (I) that are:

N-{2-[7-(methylthio)-1-naphthyl]ethyl}acetamide
N-{2-[7-(methylthio)-1-naphthyl]ethyl}butanamide
N-{2-[7-(methylthio)-1-naphthyl]ethyl}-1-cyclopropanecarboxamide
N-{2-[7-(methylthio)-1-naphthyl]ethyl}-2,2,2-trifluoroacetamide
N-methyl-N'-{2-[7-(methylthio)-1-naphthyl]ethyl}urea
N-{2-[3-benzoyl-7-(methylthio)-1-naphthyl]ethyl}acetamide
N-{2-[3-benzyl-7-(methylthio)-1-naphthyl]ethyl}acetamide
N-{2-[7-(ethylthio)-1-naphthyl]ethyl}acetamide
N-{2-[7-(propylthio)-1-naphthyl]ethyl}acetamide
N-[2-(7-mercapto-1-naphthyl)ethyl]benzamide
N-{2-[7-(allylthio)-1-naphthyl]ethyl}-2-phenylacetamide
N-{2-[7-(benzylthio)-1-naphthyl]ethyl}heptanamide
N-methyl-2-[7-(cyclopentylthio)-1-naphthyl]acetamide
N-cyclohexyl-4-[7-(phenylthio)-1-naphthyl]butanamide
N-{2-[7-(allylthio)-3-phenyl-1-naphthyl]ethyl}acetamide
N-{2[7-(benzylthio)-3-phenyl-1-naphthyl]ethyl}acetamide
N-{2-[5-(2-pyridylthio)benzo[b]furan-3-yl]ethyl}acetamide
N-{[2-benzyl-5-(3-butenylthio)benzo[b]thiophen-3-yl]methyl}acetamide
N-{2-[1-methyl-2-phenyl-5-(propylthio)-1H-pyrrolo[2,3-b]pyridin-3-yl]ethyl}acetamide
N-{2-[5-(allylthio)-2-benzylbenzo[b]furan-3-yl]ethyl}-1-cyclopropanecarboxamide
N-{2-[5-(propylthio)-2-phenylbenzo[b]thiophen-3-yl]ethyl}acetamide
N-{[6-(benzylthio)-2-phenyl-2H-3-chromenyl]methyl}acetamide
N-{2-[5-(isopentylthio)benzo[b]thiophen-3-yl]ethyl}acrylamide
N-{3-[7-(1-propenylthio)-1,2,3,4-tetrahydro-1-naphthyl]propyl}acetamide
N-{[2-(2-furylmethyl)-5-(2-propynylthio)benzo[b]furan-3-yl]methyl}acetamide
N-[4-(butylthio)-2,3-dihydro-1H-2-phenalenyl]propanamide
ethyl 10-{3-[(cyclohexylcarbonyl)amino]propyl}-1-methyl-3H-benzo[f]thiochromene-3-carboxylate
N-[3-(1-oxo-2,3,7,8,9,10-hexahydro-1H-benzo[f]thiochromen-10-yl)propyl]acetamide
N-[(2-benzyl-8,9-dihydro-7H-thieno[3,2-f]thiochromen-1-yl)methyl]acetamide
N-[2-(3H-benzo[f]thiochromen-10-yl)ethyl]-2-bromoacetamide
N-[3-(7-methyl-7H-thiochromeno[6,5-b]furan-1-yl)propyl]acetamide
N-methyl-4-(8-hydroxy-7,7-dimethyl-7,8-dihydrothieno[3',2':3,4]benzo[f]furan-1-yl)-butanamide
N-{2-[7-amino-3-(cyclopropylmethyl)-1-naphthyl]ethyl}acetamide
N-{2-[7-(diethylamino)-1-naphthyl]ethyl}-2-phenylacetamide
N-{2-[7-(hexylamino)-1,2,3,4-tetrahydro-1-naphthyl]ethyl}acetamide
N-[(6-morpholino-2-phenyl-2H-3-chromenyl)methyl]acetamide
N-[2-(3-benzyl-3H-benzo[e]indol-9-yl)propyl]-1-cyclohexanecarboxamide
N-[(2-benzyl-6-ethyl-6,7-dihydrothieno[3,2-f]quinolin-1-yl)methyl]acetamide
ethyl 9-[2-(phenylacetylamino)ethyl]-1-methyl-3H-benzo[e]indole-2-carboxylate
N-[2-(4-methyl-1,2,3,4-tetrahydro[f]quinolin-10-yl)ethyl]-2-phenylacetamide
N-[2-(1-hydroxy-4-methyl-1,2,3,4-tetrahydrobenzo[f]quinolin-10-yl)ethyl]-2-phenylacetamide,
N-{2-[7-(methylsulphinyl)-1-naphthyl]ethyl}acetamide,
N-{2-[7-(methylsulphonyl)-1-naphthyl]ethyl}acetamide,
N-{2-[7-(methylthio)-1,2,3,4-tetrahydro-1-naphthyl]ethyl}acetamide,
N-{2-[7-(methylsulphinyl)-1,2,3,4-tetrahydro-1-naphthyl]ethyl}acetamide,
N-{2-[7-(methylsulphonyl)-1,2,3,4-tetrahydro-1-naphthyl]ethyl}acetamide, N-{2-[7-(benzylthio)-1-naphthyl]ethyl}acetamide,
N-{2-[7-(benzylsulphinyl)-1-naphthyl]ethyl}acetamide,
N-{2-[7-(benzylsulphonyl)-1-naphthyl]ethyl}acetamide,
N-[2-(7-mercapto-1-naphthyl)ethyl]benzamide,
N-[2-(3-benzyl-7-mercapto-1-naphthyl)ethyl]-1-cyclohexanecarboxamide,
N-[2-(5-mercaptobenzo[b]furan-3-yl)ethyl]acetamide,
N-[2-(2-benzyl-5-mercaptobenzo[b]furan-3-yl)ethyl]-1-cyclopropanecarboxamide.

The enantiomers and diastereoisomers, as well as the addition salts with a pharmaceutically acceptable acid or base, of the preferred compounds of the invention form an integral part of the invention.

The invention relates also to a process for the preparation of compounds of formula (I), which process is characterised in that there is used as starting material the compound of formula (VIII):

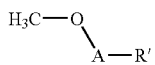 (VIII)

wherein A and R' are as defined hereinbefore, which is subjected to demethylation using conventional agents such as HBr, AlCl$_3$, AlBr$_3$, BBr$_3$ or Lewis acid/nucleophile binary systems such as AlCl$_3$/PhCH$_2$SH, or BBr$_3$/Me$_2$S, for example, to obtain the compound of formula (IX):

HO-A-R' (IX)

wherein A and R' are as defined hereinbefore,
with which, in the presence of trifluoromethanesulphonic acid, there is condensed a thiol of formula (X):

R$^1$—SH (X)

wherein R$^1$ is as defined hereinbefore, to obtain the compound of formula (I/a), a particular case of the compounds of formula (I):

R$^1$—S-A-R' (I/a)

wherein R$^1$, A and R' are as defined hereinbefore, which compound of formula (I/a), when R$^1$ represents a group R$_a$ as defined hereinbefore, may be obtained directly starting from the compound of formula (X) by the action of AlCl$_3$ and the thiol of formula (XI):

R$_a$—SH (XI)

wherein R$_a$ is as defined hereinbefore, which compound of formula (I/a) may be obtained starting from the compound of formula (I/a'), a particular case of the compounds of formula (I/a):

HS-A-R' (I/a')

wherein A and R' are as defined hereinbefore, which is reacted in a basic medium with a compound of formula (XII):

R'$^1$-M (XII)

wherein R'$^1$ may have any of the meanings of R$^1$ except for hydrogen and M represents a leaving group such as a halogen atom, for example, which compound of formula (I/a) may also be obtained, when A represents a ring system of formula (XIII):

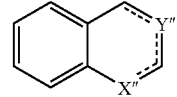 (XIII)

wherein the symbol ⋯ is as defined hereinbefore, Y" represents a group C(H)$_q$ (wherein q is 0, 1 or 2) or a bond, and X" represents an oxygen, nitrogen or sulphur atom or a group C(H)$_q$ (wherein q is 0, 1 or 2) or NR$_0$ (wherein R$_0$ is as defined hereinbefore), it being understood that when X" represents a nitrogen atom or a group NR$_0$ then Y" represents a bond, starting from a compound of formula (XIV):

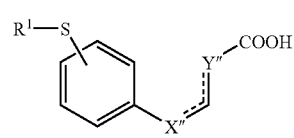 (XIV)

wherein R$^1$, X", Y" and the symbol ⋯ are as defined hereinbefore, which is cyclised in the presence of polyphosphoric acid to yield the compound of formula (XV):

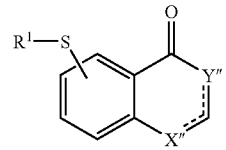 (XV)

wherein R$^1$, X", Y" and the symbol ⋯ are as defined hereinbefore, which is subjected to a Wittig reaction and then to reduction to yield the compound of formula (XVI):

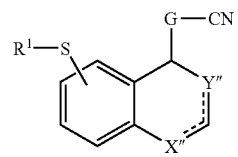 (XVI)

wherein R$^1$, X", Y", G and the symbol ⋯ are as defined hereinbefore, which may be oxidised to yield the compound of formula (XVII):

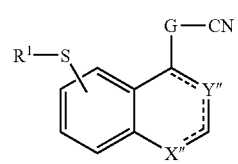 (XVII)

wherein R¹, X″, Y″, G and the symbol ⋯ are as defined hereinbefore, which is:
either hydrolysed in an acid or basic medium and then subjected, after activation to the acid chloride form or in the presence of a coupling agent, to the action of an amine HNR'$_a$R″$_a$, wherein R'$_a$ and R″$_a$ are as defined hereinbefore, to yield the compound of formula (I/b), a particular case of the compounds of formula (I):

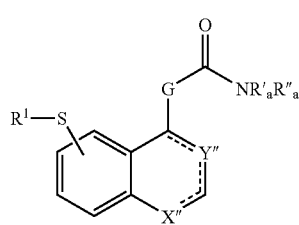

(I/b)

wherein R¹, X″, Y″, G, R'$_a$, R″$_a$ and the symbol ⋯ are as defined hereinbefore, which may be subjected to a thionating agent such as Lawesson's reagent to yield the compound of formula (I/c), a particular case of the compounds of formula (I):

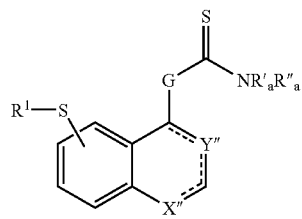

(I/c)

wherein R¹, X″, Y″, G, R'$_a$, R″$_a$ and the symbol ⋯ are as defined hereinbefore, or reduced and then reacted with:
an acyl chloride ClCOR'$_a$ or the corresponding anhydride (mixed or symmetrical), wherein R'$_a$ is as defined hereinbefore, optionally followed by the action of a compound of formula (XVIII):

R$_{1a}$-J (XVIII)

wherein R$_{1a}$ can take any of the meanings of the group R$_a$ except for a hydrogen atom and J represents a leaving group such as a halogen atom or a tosyl group, and/or by the action of a thionating agent to yield the compound of formula (I/d), a particular case of the compounds of formula (I):

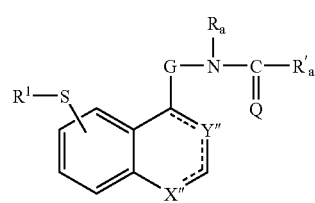

(I/d)

wherein R¹, X″, Y″, G, R$_a$, R'$_a$, Q and the symbol ⋯ are as defined hereinbefore, or with a compound of formula (XIX):

Q=C=N—R'$_a$ (XIX)

wherein Q and R'$_a$ are as defined hereinbefore, optionally followed by the action of a compound of formula (XVIII) to yield the compound of formula (I/e), a particular case of the compounds of formula (I):

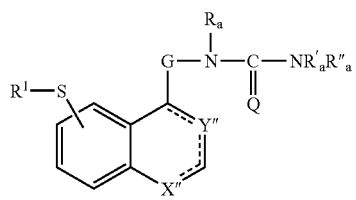

(I/e)

wherein R¹, X″, Y″, G, R$_a$, R'$_a$, R″$_a$, Q and the symbol ⋯ are as defined hereinbefore, which compounds (I/a) to (I/e) may be reacted with an oxidising agent such as H$_2$O$_2$, NaIO$_4$, KMnO$_4$ or NaOCl or meta-chloroperbenzoic acid, for example, to yield the compound of formula (I/f), a particular case of the compounds of formula (I):

$$R^1-S-A-R'$$
$$(O)_{r'}$$

(I/f)

wherein R¹, A and R' are as defined hereinbefore and r' represents an integer such that 1≦r'≦2, or which compound of formula (IX) is converted, by means of the action of reagents such as POCl$_3$, PCl$_5$, Ph$_3$PBr$_2$, PhPCl$_4$, HBr or HI, into the corresponding halogenated compound of formula (XX):

Hal-A-R' (XX)

wherein A and R' are as defined hereinbefore and Hal represents a halogen atom (which compounds of formula (XX) can be obtained by exchange reactions such as, for example, the treatment of a chlorinated compound with KF in dimethylformamide to yield the corresponding fluorinated compound or the treatment of a brominated compound with KI in the presence of copper salts to yield the corresponding iodinated compound, and which compounds of formula (XX) can also be obtained starting from compounds of formula (XX$_1$) or (XX$_2$):

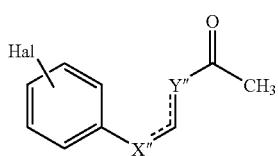

(XX$_1$)

-continued (XX₂)

[structure: Hal-substituted benzene ring with X″ and Y″ substituents, -COOH group]

wherein Hal, X″ and Y″ are as defined hereinbefore), which compound of formula (XX) is:
  either treated with carbon monoxide and Bu₃SnH, the reaction being catalysed with palladium(0), to yield the corresponding aldehyde of formula (XXI):

$$H-\underset{\underset{O}{\|}}{C}-A-R' \qquad (XXI)$$

wherein A and R' are as defined hereinbefore, which compound of formula (XXI) may alternatively be obtained by customary lithiation methods starting from the halogenated compound of formula (XX), or via the corresponding vinyl compound (obtained starting from the compound of formula (XX) by the action of vinyltributyltin and tetrakis palladium) subjected to ozonolysis, or furthermore by direct formylation of the nucleus A, for example according to a Vilsmeier reaction, which compound of formula (XXI) is subjected to an oxidising agent to obtain the compound of formula (XXII):

HOOC-A-R' (XXII)

wherein A and R' are as defined hereinbefore, which is converted, after the action of thionyl chloride and an azide, and then of an acid, into the compound of formula (I/g), a particular case of the compounds of formula (I):

H₂N-A-R' (I/g)

wherein A and R' are as defined hereinbefore, with which there is condensed one or two molecules of a compound of formula (XVIII) to obtain the compound of formula (I/h), a particular case of the compounds of formula (I):

R'$_{2a}$R$_{2a}$N-A-R' (I/h)

wherein A and R' are as defined hereinbefore and R'$_{2a}$ and R$_{2a}$, which may be the same or different, represent a group R$_a$ with the following proviso: R'$_{2a}$ and R$_{2a}$ cannot simultaneously represent a hydrogen atom and cannot form, together with the nitrogen atom carrying them, a cyclic group,
  or which compound of formula (XX) is subjected, under conditions of nucleophilic aromatic substitution, to the action of an amine R'$_a$R″$_a$NH, wherein R'$_a$ and R″$_a$ are as defined hereinbefore (R'$_a$ and R″$_a$ may, inter alia, form, together with the nitrogen atom carrying them, a cyclic group as defined hereinbefore), to yield the compound of formula (I/i), a particular case of the compounds of formula (I):

R'$_a$R″$_a$N-A-R' (I/i)

wherein R'$_a$, R″$_a$, A and R' are as defined hereinbefore, which compounds (I/a) to (I/i) can be purified in accordance with a conventional separation technique, are converted, if desired, into their addition salts with a pharmaceutically acceptable acid or base and, optionally, are separated into their isomers in accordance with a conventional separation technique.

The starting compounds (VIII) are either commercially available or are described in the literature, for example in the Patent Applications EP0447285, EP0527687, EP0562956, EP0591057, EP0662471, EP0745586, EP0709371, EP0745583, EP0721938, EP0745584, EP0737670, EP0737685, or WO9738682.

The invention relates also to a process for the preparation of compounds of formula (I) wherein R represents a ring of formula (VI), which process is characterised in that compounds of formulae (I/a) to (I/i) are used as starting materials, which are cyclised according to methods described in the literature, for example in the Patent Applications EP0708099 or WO9732871.

The compounds of the invention and pharmaceutical compositions comprising them are proving to be useful in the treatment of disorders of the melatoninergic system.

The invention relates also to the compounds of formula (XX$_A$), a particular case of the compounds of formula (XX):

Hal-A$_A$-R'$_A$ (XX$_A$)

wherein:
  Hal represents a halogen atom (fluorine, chlorine, bromine, iodine),
  A$_A$ represents:
    a ring system of formula (a):

(a)

[structure: benzene ring fused with 5-membered ring containing X$_A$]

wherein X$_A$ represents a sulphur atom or a group C(H)$_q$ (wherein q is 0, 1 or 2) or NR$_0$ (wherein R$_0$ is as defined hereinbefore), and the symbol ····· is as defined hereinbefore,
  wherein the halogen atom substitutes the benzene nucleus and the group R'$_A$ substitutes the 5-membered ring,
  or a ring system of formula (b):

(b)

[structure: benzene ring fused with 6-membered ring containing Y$_A$ and Z$_A$]

wherein Y$_A$ and Z$_A$, which may be the same or different, represent an oxygen or sulphur atom or a group C(H)$_q$ (wherein q is 0, 1 or 2), and the symbol ····· is as defined hereinbefore,
  wherein the halogen atom substitutes the benzene nucleus and the group R'$_A$ substitutes one or other of the two rings,
  which ring systems of formula (a) or (b) may be substituted (in addition to the halogen atom and the group R'$_A$) by one or more groups selected from R$_a$, COR$_a$, COOR$_a$, OCOR$_a$ wherein R$_a$ is as defined hereinbefore, and R'$_A$ represents a group G-R$^2_A$ wherein G is as defined hereinbefore and R$^2_A$ represents a group

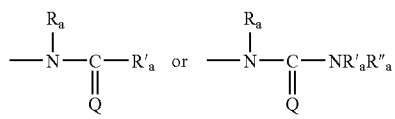

wherein R$_a$, R'$_a$, R"$_a$ and Q are as defined hereinbefore, their enantiomers and diastereoisomers, and addition salts thereof with a pharmaceutically acceptable acid or base, as synthesis intermediates but also as compounds for use in the treatment of disorders associated with the melatoninergic system.

Pharmacological study of the compounds of the invention has in fact shown them to be non-toxic, to have strong affinity for melatonin receptors and to possess important activities in respect of the central nervous system and, in particular, there have been found therapeutic properties in relation to sleep disorders, anxiolytic, antipsychotic and analgesic properties and in relation to the microcirculation, enabling it to be established that the products of the invention are useful in the treatment of stress, sleep disorders, anxiety, seasonal affective disorder, cardiovascular pathologies, pathologies of the digestive system, insomnia and fatigue resulting from jet lag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and also cerebral circulation disorders. In another field of activity, it appears that, in treatment, the products of the invention can be used in sexual dysfunction, that they have ovulation-inhibiting properties and immunomodulating properties and are able to be used in the treatment of cancers.

The compounds will preferably be used in the treatment of seasonal affective disorder, sleep disorders, cardiovascular pathologies, insomnia and fatigue resulting from jet lag, appetite disorders and obesity.

For example, the compounds will be used in the treatment of seasonal affective disorder and sleep disorders.

The present invention relates also to pharmaceutical compositions comprising at least one compound of formula (I), alone or in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration and especially tablets, dragées, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, or possible associated treatments, and ranges from 0.01 mg to 1 g per 24 hours in 1 or more administrations.

The following Examples illustrate the invention but do not limit it in any way. The following Preparations yield compounds of the invention or synthesis intermediates that are useful in preparation of the compounds of the invention.

Preparation 1

2-[7-(Methylthio)-1-naphthyl]-1-ethylamine hydrochloride

Step A: 4-[4-(Methylthio)phenyl]-4-oxo-butanoic acid

Succinic anhydride (17 g, 170 mmol) is added to a solution of thioanisole (20 ml, 170 mmol) in 140 ml of tetrachloroethane and the reaction mixture is then brought to 0° C. Aluminium trichloride (45.43 g, 341 mmol) is added in portions and the reaction mixture is then heated at 60° C. for 3.00 hours. After cooling and hydrolysis in the presence of ice-cold water (500 ml) and concentrated hydrochloric acid (50 ml), the white precipitate formed is filtered off, rinsed with water and recrystallised from ethyl acetate to yield the desired acid.

Melting point=153–155° C.

Step B: 4-[4-(Methylthio)phenyl]butanoic acid

A solution of the acid obtained in Step A (19.8 g, 88.1 mmol) in trifluoroacetic acid (68 ml, 881 mmol) is brought to 0° C. and then triethylsilane hydride (35.2 ml, 220 mmol) is added dropwise using a dropping funnel. Stirring is carried out at ambient temperature for 17 hours. After hydrolysis, the white precipitate formed is filtered off, rinsed with water and with cyclohexane and is then purified by chromatography on silica gel (eluant: acetone/toluene/cyclohexane 30/50/20) to yield the title compound.

Melting point=53–55° C.

Step C: 7-(Methylthio)-1,2,3,4-tetrahydro-1-naphthalenone

With the aid of a mechanical stirrer, the acid obtained in Step B (10 g, 52 mmol) is heated at 70° C. for 2 hours in the presence of 10 times as much, by weight, polyphosphoric acid (100 g). The reaction mixture is hydrolysed in ice and is then extracted with ethyl ether. The organic phase is washed with water, dried over magnesium sulphate and evaporated. The residue is purified by chromatography on silica gel (eluant: dichloromethane) to yield the expected tetralone in the form of a yellow oil.

Step D: 2-[7-(Methylthio)-1,2,3,4-tetrahydro-1-naphthalenylidene]acetonitrile

Under an inert atmosphere and at 0° C., diethyl cyanomethylphosphonate (7.6 ml, 46.8 mmol) is added dropwise to a suspension of sodium hydride (2.25 g, 46.8 mmol) in 50 ml of tetrahydrofuran. Stirring is carried out at 0° C. for 30 minutes; the compound obtained in Step C (6 g, 31.2 mmol), dissolved in 50 ml of tetrahydrofuran, is then added and the reaction mixture is stirred at ambient temperature for 3 hours. After hydrolysis and extraction with ethyl acetate, the organic phase is washed with water, dried over magnesium sulphate and evaporated. The residue is purified by chromatography on silica gel (eluant: petroleum ether/dichloromethane 50/50) to yield the unsaturated nitrile of the title.

Melting point=60–61° C.

Step E: 2-[7-(Methylthio)-1-naphthyl]acetonitrile

The compound obtained in Step D (2 g, 9.29 mmol) is heated at 230° C. in the presence of sulphur (357 mg, 11.1 mmol) for 16 hours. After hydrolysis and extraction with ethyl acetate, the organic phase is washed with water, dried over magnesium sulphate and evaporated. The residue is purified by chromatography on silica gel (eluant: cyclohexane/ethyl acetate 80/20) to yield the corresponding aromatic compound in the form of a beige solid.

Step F: 2-[7-(Methylthio)-1-naphthyl]-1-ethylamine hydrochloride

Under an inert atmosphere, the compound obtained in Step E (1.93 g, 9.04 mmol), previously dissolved in 30 ml of tetrahydrofuran, is added to a 1M solution of borane in tetrahydrofuran (27.1 ml, 22.1 mmol) and the reaction mixture is then heated at reflux for 3 hours. A 6N hydrochloric acid solution (18 ml, 108 mmol) is then added very slowly and stirring is carried out at reflux for 30 minutes more. After extraction with ethyl acetate, the aqueous phase is rendered alkaline with 16% sodium hydroxide solution and is then extracted with ethyl acetate. The organic phase is washed with water, dried over magnesium sulphate and evaporated. The residue is purified by chromatography on silica gel (eluant: dichloromethane/methanol 50/50 and then methanol/ammonium hydroxide 95/5) to yield the expected amine. The amine is taken up in ethyl ether; ethyl ether saturated with gaseous hydrogen chloride is then added dropwise and the precipitate obtained is filtered off to yield the corresponding hydrochloride in the form of a white solid.

Melting point=199° C.

Elemental Microanalysis:

|  | C | H | N |
|---|---|---|---|
| % calculated | 61.52 | 6.35 | 5.52 |
| % found | 61.60 | 6.33 | 5.45 |

Preparation 2

N-[2-(7-Hydroxy-1-naphthyl)ethyl]acetamide

Under an inert atmosphere, 27.5 mmol of boron tribromide/dimethyl sulphide complex are dissolved in 100 ml of dichloromethane and stirred for 15 min at ambient temperature. A solution of 13.7 mmol of N-[2-(7-methoxy-1-naphthyl)ethyl]acetamide in 50 ml of dichloromethane is added and the reaction mixture is heated at reflux for 30 hours. After cooling, the reaction mixture is hydrolysed with caution and the dichloromethane is evaporated off. The mixture is then extracted with ethyl acetate, the combined organic phases are washed with a 1M aqueous solution of potassium bicarbonate and then with 1M sodium hydroxide solution. The organic phase is dried over magnesium sulphate and concentrated to yield the title compound.

Preparation 3

N-[2-(7-Hydroxy-1-naphthyl)ethyl]-2-phenylacetamide

The procedure is as in Preparation 2, but the N-[2-(7-methoxy-1-naphthyl)ethyl]acetamide is replaced by N-[2-(7-methoxy-1-naphthyl)ethyl]-2-phenylacetamide.

In Preparations 4 to 125, the procedure is as in Preparation 2, but the N-[2-(7-methoxy-1-naphthyl)ethyl]acetamide is replaced by the appropriate methoxylated starting substrate.

Preparation 4

N-[2-(7-Hydroxy-1-naphthyl)ethyl]-2-(2-oxotetrahydro-1H-1-pyrrolyl)acetamide

Preparation 5

N-[2-(7-Hydroxy-1-naphthyl)ethyl]benzamide

Preparation 6

N-[2-(7-Hydroxy-1-naphthyl)ethyl]-3-(trifluoromethyl)benzamide

Preparation 7

N-[2-(7-Hydroxy-1-naphthyl)ethyl]-2-thiophenecarboxamide

Preparation 8

N-[2-(7-Hydroxy-1-naphthyl)ethyl]-2-bromoacetamide

Preparation 9

N-[2-(7-Hydroxy-1-naphthyl)ethyl]-4-chlorobutanamide

Preparation 10

N-[2-(7-Hydroxy-1-naphthyl)ethyl]heptanamide

Preparation 11

N-[2-(8-Allyl-7-hydroxy-1-naphthyl)ethyl]acetamide

Preparation 12

N-[2-(8-Allyl-7-hydroxy-1-naphthyl)ethyl]heptanamide

Preparation 13

N-{2-[7-Hydroxy-8-(1-propenyl)-1-naphthyl]ethyl)acetamide

Preparation 14

N-(2-[7-Hydroxy-8-(1-propynyl)-1-naphthyl]ethyl)acetamide

Preparation 15

N-[2-(8-Hexyl-7-hydroxy-1-naphthyl)ethyl]-2-phenylacetamide

Preparation 16

N-[2-(8-Allyl-7-hydroxy-1-naphthyl)ethyl]-N'-cyclobutylthiourea

Preparation 17

N-Methyl-2-(7-hydroxy-1-naphthyl)acetamide

Preparation 18

N-Cyclobutyl-3-(7-hydroxy-1-naphthyl)propanamide

Preparation 19

N-Propyl-4-(7-hydroxy-1-naphthyl)butanamide

Preparation 20

N-Cyclopropylmethyl-2-(7-hydroxy-1-naphthyl)acetamide

Preparation 21

N-Cyclohexyl-4-(7-hydroxy-1-naphthyl)butanamide

Preparation 22

N-Allyl-3-(7-hydroxy-1-naphthyl)propanamide

Preparation 23

N-Cyclobutyl-N'-[2-(7-hydroxy-1-naphthyl)ethyl]urea

Preparation 24

N-Isopropyl-N'-[2-(7-hydroxy-1-naphthyl)ethyl]thiourea

Preparation 25

N-[2-(7-Hydroxy-1-naphthyl)ethyl]-N-methyl-N'-propylurea

Preparation 26

N-Butyl-N'-[2-(7-hydroxy-1-naphthyl)ethyl]thiourea

Preparation 27

N-Di(4-chlorophenyl)methyl-N'-[2-(7-hydroxy-1-naphthyl)ethyl]urea

Preparation 28

Methyl 2-(7-hydroxy-1-naphthyl)-3-[(2-morpholinoacetyl)amino]propanoate

Preparation 29

Methyl 2-(7-hydroxy-1-naphthyl)-3-[(cyclopropylcarbonyl)amino]propanoate

Preparation 30

Methyl 2-(7-hydroxy-1-naphthyl)-3-[(2,2,2-trifluoroacetyl)amino]propanoate

Preparation 31

O-[(7-Hydroxy-1-naphthyl)methyl]-N-acetylhydroxylamine

Preparation 32

O-[(7-Hydroxy-1-naphthyl)methyl]-N-(2-butenoyl)hydroxylamine

Preparation 33

N-[3-(7-Hydroxy-1-naphthyl)propyl]acetamide

Preparation 34

N-[3-(7-Hydroxy-1-naphthyl)propyl]-1-cyclohexanecarboxamide

Preparation 35

N-[3-(7-Hydroxy-1-naphthyl)propyl]-N'-propylthiourea

Preparation 36

N-[2-(2-Hydroxy-1-naphthyl)ethyl]-2,2,2-trifluoroacetamide

Preparation 37

N-[2-(2-Hydroxy-1-naphthyl)ethyl]-2-butenamide

Preparation 38

N-[2-(2-Hydroxy-1-naphthyl)ethyl]-1-cyclohexanecarboxamide

Preparation 39

N-[2-(2-Hydroxy-1-naphthyl)-1-methylethyl]propanamide

Preparation 40

N-[2-(7-Hydroxy-3-phenyl-1-naphthyl)ethyl]acetamide

Preparation 41

N-[2-(3-Benzoyl-7-hydroxy-1-naphthyl)ethyl]acetamide

Preparation 42

N-[2-(3-Benzoyl-7-hydroxy-1-naphthyl)ethyl]-N'-propylurea

Preparation 43

N-{2-[3-(Cyclopropylcarbonyl)-7-hydroxy-1-naphthyl]ethyl}-1-cyclobutanecarboxamide Preparation 44

N-{2-[3-(Cyclopropylcarbonyl)-7-hydroxy-1-naphthyl]ethyl}-N'-propylurea

Preparation 45

N-[2-(3,7-Dihydroxy-1-naphthyl)ethyl]propanamide

Preparation 46

4-{2-[(Cyclopropylcarbonyl)amino]ethyl}-6-hydroxy-2-naphthyl acetate

Preparation 47

N-[2-(3-Benzyl-7-hydroxy-1-naphthyl)ethyl]pentanamide

Preparation 48

N-[2-(3-Benzyl-7-hydroxy-1-naphthyl)ethyl]cyclohexanecarboxamide

Preparation 49

N-Cyclohexyl-N'-[2-(3-ethyl-7-hydroxy-1-naphthyl)ethyl]urea

Preparation 50

N-{2-[3-(Cyclopropylmethyl)-7-hydroxy-1-naphthyl]ethyl}acetamide

Preparation 51

N-[(5-Hydroxybenzo[b]furan-3-yl)methyloxy]-N'-propylthiourea

Preparation 52

N-[3-(5-Hydroxybenzo[b]furan-3-yl)propyl]acetamide

Preparation 53

N-[2-(5-Hydroxy-2-methylbenzo[b]furan-3-yl)ethyl]heptanamide

Preparation 54

N-Methyl-4-(5-hydroxybenzo[b]furan-3-yl)butanamide

Preparation 55

N-[2-(4-Allyl-5-hydroxybenzo[b]furan-3-yl)ethyl]benzamide

Preparation 56

N-[2-(5-Hydroxybenzo[b]furan-3-yl)ethyl]acetamide

Preparation 57

O-[(5-Hydroxybenzo[b]thiophen-3-yl)methyl]-N-thiopropionylhydroxylamine

Preparation 58

N-[3-(5-Hydroxybenzo[b]thiophen-3-yl)propyl]-1-cyclopropane-carboxamide

Preparation 59

N-[(2-Benzyl-5-hydroxybenzo[b]thiophen-3-yl)methyl]acetamide

Preparation 60

N-[2-(5-Hydroxythieno[3,2-b]pyridin-3-yl)ethyl]acetamide

Preparation 61

N-[2-(4-Allyl-5-hydroxybenzo[b]thiophen-3-yl)ethyl]benzamide

Preparation 62

N-[2-(5-Hydroxy-1H-4-indolyl)ethyl]-1-cyclopropanecarboxamide

Preparation 63

N-Methyl-4-(5-hydroxybenzo-1H-3-indolyl)butanamide

Preparation 64

N-[2-(5-Hydroxy-1H-3-indolyl)ethyl]-2-morpholinoacetamide

Preparation 65

N-Benzyl-N'-[2-(5-hydroxy-1H-3-indolyl)ethyl]urea

Preparation 66

N-[2-(5-Hydroxy-1H-3-indolyl)ethyl]benzamide

Preparation 67

N-[2-(5-Hydroxy-1-methyl-2-phenyl-1H-pyrrolo[2,3-b]pyridin-3-yl)ethyl]acetamide

Preparation 68

N-{2-[5-Hydroxy-2-(2-methoxyphenyl)-1-methyl-1H-pyrrolo[2,3-b]pyridin-3-yl]ethyl}acetamide Preparation 69

N-{2-[2-(4-Fluorobenzyl)-5-hydroxy-1-methyl-1H-pyrrolo[2,3-b]pyridin-3-yl]ethyl}acetamide Preparation 70

N-[2-(2-Benzyl-5-hydroxy-1-methyl-1H-pyrrolo[2,3-b]pyridin-3-yl]ethyl}acetamide

Preparation 71

N-[2-(5-Hydroxy-1H-pyrrolo[2,3-b]pyridin-3-yl)ethyl]acetamide

Preparation 72

N-[2-(5-Hydroxy-1H-pyrrolo[2,3-b]pyridin-3-yl)ethyl]trifluoroacetamide

Preparation 73

N-[2-(5-Hydroxy-2-phenyl-1H-pyrrolo[2,3-b]pyridin-3-yl)ethyl]acetamide

Preparation 74

N-[2-(5-Hydroxy-1H-pyrrolo[2,3-b]pyridin-3-yl)ethyl]-N'-propylurea

Preparation 75

N-[2-(5-Hydroxy-1H-pyrrolo[2,3-b]pyridin-3-yl)ethyl]cyclobutanecarboxamide

Preparation 76

N-[2-(5-Hydroxy-1H-pyrrolo[2,3-b]pyridin-3-yl)ethyl]-N'-butylthiourea

Preparation 77

N-[2-(2-Benzyl-5-hydroxybenzo[b]furan-3-yl)ethyl]-1-cyclopropane-carboxamide

Preparation 78

N-[2-(6-Hydroxy-1H-benzo-imidazol-1-yl)ethyl]-1-cyclopropane-carboxamide

Preparation 79

N-[(6-Hydroxy-3,4-dihydro-2H-3-chromenyl)methyl]acetamide

Preparation 80

N-[(6-Hydroxy-3,4-dihydro-2H-3-chromenyl)methyl]cyclopropane-carboxamide

Preparation 81

N-[2-(6-Hydroxy-3,4-dihydro-2H-3-chromenyl)ethyl]acetamide

Preparation 82

N-[(6-Hydroxy-3,4-dihydro-2H-4-chromenyl)methyl]acetamide

Preparation 83

N-[(6-Hydroxy-3,4-dihydro-2H-3-chromenyl)methyl]butanamide

Preparation 84

N-[2-(6-Hydroxy-3,4-dihydro-2H-4-chromenyl)ethyl]-3-butenamide

Preparation 85

N-[2-(6-Hydroxy-3,4-dihydro-2H-4-chromenyl)ethyl]acetamide

Preparation 86

N-[2-(6-Hydroxy-3,4-dihydro-2H-4-chromenyl)ethyl]-2-phenylacetamide

Preparation 87

N-[(6-Hydroxy-2H-3-chromenyl)methyl]acetamide

Preparation 88

N-[(6-Hydroxy-2H-3-chromenyl)methyl]butanamide

Preparation 89

N-Methyl-3-(6-hydroxy-2H-3-chromenyl)propanamide

Preparation 90

N-[(6-Hydroxy-2-phenyl-2H-3-chromenyl)methyl]acetamide

Preparation 91

N-[(6-Hydroxy-2-phenyl-2H-3-chromenyl)methyl]butanamide

Preparation 92

N-[2-(6-Hydroxy-3,4-dihydro-2H-4-thiochromenyl)ethyl]acetamide

Preparation 93

N-[(7-Hydroxy-3-phenyl-1,4-benzodioxin-2-yl)methyl]acetamide

Preparation 94

N-[(3-Benzyl-7-hydroxy-1,4-benzodioxin-2-yl)methyl]acetamide

Preparation 95

N-[(7-Hydroxy-1,4-benzodioxin-2-yl)methyl]cyclopropanecarboxamide

Preparation 96

N-[2-(7-Hydroxy-1,4-benzodioxin-2-yl)ethyl-N'-propylurea

Preparation 97

N-[2-(7-Hydroxy-2,3-dihydro-1,4-benzodioxin-2-yl)ethyl]acetamide

Preparation 98

N-Phenyl-2-(7-hydroxy-2,3-dihydro-1,4-benzodioxin-2-yl)acetamide

Preparation 99

N-[2-(6-Hydroxy-2,3-dihydro-1,4-benzodioxin-5-yl)ethyl]acetamide

Preparation 100

N-[3-(7-Hydroxy-1,2,3,4-tetrahydro-1-naphthyl)propyl]acetamide

Preparation 101

N-[2-(5-Hydroxybenzo[d]isoxazol-3-yl)ethyl]-1-cyclopropanecarboxamide

Preparation 102

N-(9-Hydroxy-2,3-dihydro-1H-benzo[f]chromen-2-yl)acetamide

Preparation 103

N-[(9-Hydroxy-2,3-dihydro-1H-benzo[f]chromen-2-yl)methyl]-2-cyclopropylacetamide

Preparation 104

N-(9-Hydroxy-2,3-dihydro-1H-benzo[f]chromen-1-yl)butanamide

Preparation 105

N-[(9-Hydroxy-2,3-dihydro-1H-benzo[f]chromen-1-yl)methyl]acetamide

Preparation 106

N-Methyl-9-hydroxy-3H-benzo[f]chromene-2-carboxamide

Preparation 107

N-(4-Hydroxy-2,3-dihydro-1H-2-phenalenyl)propanamide

Preparation 108

N-(4-Hydroxy-2,3-dihydro-1H-2-phenalenyl)-2-methylpropanamide

Preparation 109

N-Cyclopropyl-N'-(4-hydroxy-2,3-dihydro-1H-2-phenalenyl)thiourea

Preparation 110

N-Cyclohexyl-N'-(4-hydroxy-2,3-dihydro-1H-2-phenalenyl)urea

Preparation 111

N-(4,9-Dihydroxy-2,3-dihydro-1H-2-phenalenyl)acetamide

Preparation 112

N-[(4-Hydroxy-2,3-dihydro-1H-1-phenalenyl)methyl]acetamide

Preparation 113

N-[2-(4-Hydroxy-2,3-dihydro-1H-1-phenalenyl)ethyl]-1-cyclopropane-carboxamide

Preparation 114

N-[(4,9-Dihydroxy-2,3-dihydro-1H-1-phenalenyl)methyl]-N'-methylurea

Preparation 115

N-(6-Hydroxy-1,3,4,5-tetrahydrobenzo[cd]indol-4-yl)acetamide

Preparation 116

N-(6-Hydroxy-4,5-dihydro-3H-benzo[cd]isobenzofuran-4-yl)acetamide

Preparation 117

N-(6-Hydroxy-4,5-dihydro-3H-naphtho[1,8-bc]thiophen-4-yl)acetamide

Preparation 118

N-Cyclobutyl-3-hydroxy-4,5-dihydro-3H-benzo[cd]isobenzofuran-4-carboxamide

Preparation 119

N-{[2-(2-Furylmethyl)-5-hydroxybenzo[b]furan-3-yl]methyl}acetamide

Preparation 120

N-{[5-Hydroxy-2-(3-pyridylmethyl)benzo[b]furan-3-yl]methyl}benzamide

Preparation 121

N-{[5-Hydroxy-2-(3-phenyl-2-propenyl)benzo[b]thiophen-3-yl]methyl}-1-cyclobutanecarboxamide

Preparation 122

N-{2-[7-Hydroxy-3-naphthyl-1-naphthyl]ethyl}heptanamide

Preparation 123

4-[2-(Benzoylamino)ethyl]-6-hydroxy-2-naphthyl trifluoromethanesulphonate

Preparation 124

N-{2-[7-Hydroxy-3-(3-phenyl-2-propenyl)-1-naphthyl]ethyl}-2-phenylacetamide

Preparation 125

N-{[7-Hydroxy-3-(2-thienyl)-1-naphthyl]methyl}butanamide

Preparation 126

N-[2-(7-Chloro-1-naphthyl)ethyl]benzamide

Chlorine (10 mmol) is bubbled into dichlorophenylphosphine at a flow rate such that the reaction temperature is maintained between 70 and 80° C. After all the chlorine has been added, the phenylphosphine tetrachloride so obtained is a pale yellow liquid. 10 mmol of the product obtained in Preparation 5 are added all at once and the reaction mixture is heated at 160° C. overnight. After cooling, the solution is poured into a water/ice mixture (20 ml) and is neutralised with a 50% aqueous solution of sodium hydroxide. After extraction with ether, the organic phases are dried and concentrated under reduced pressure to yield a residue, which is chromatographed on silica gel to obtain the pure title product.

In Preparations 127 to 133, the procedure is as in Preparation 126, but the appropriate starting compound is used.

Preparation 127

N-{2-[7-Chloro-8-(1-propenyl)-1-naphthyl]ethyl}acetamide

Starting Compound: Preparation 13

Preparation 128

N-Cyclohexyl-4-(7-chloro-1-naphthyl)butanamide

Starting Compound: Preparation 21

Preparation 129

N-[2-(7-Chloro-3-ethyl-1-napthyl)ethyl]-N'-cyclohexylurea

Starting Compound: Preparation 49

Preparation 130

N-[2-(5-Chloro-1H-4-indolyl)ethyl-1-cyclopropanecarboxamide

Starting Compound: Preparation 62

Preparation 131

N-[(6-Chloro-3,4-dihydro-2H-3-chromenyl)methyl]acetamide

Starting Compound: Preparation 79

Preparation 132

N-(9-Chloro-2,3-dihydro-1H-benzo[f]chromen-2-yl)acetamide

Starting Compound: Preparation 102

Preparation 133

N-(4-Chloro-2,3-dihydro-1H-2-phenalenyl)-N'-cyclohexylurea

Starting Compound: Preparation 110

Preparation 134

N-[2-(7-Bromo-1-naphthyl)ethyl]-2-phenylacetamide

Triphenylphosphine (10 mmol) and acetonitrile (70 ml) are poured into a 150 ml three-necked flask equipped with a bromine funnel, a condenser surmounted by a tube filled with calcium chloride and a mechanical stirrer. The solution is cooled with the aid of an ice bath, with stirring, and bromine is added (10 mmol). At the end of the addition, the ice bath is removed and the product obtained in Preparation 3 (8 mmol) is then added. The reaction mixture is stirred at 60–70° C. until the starting compound has disappeared (monitored by TLC). At the end of the reaction, the mixture is filtered and the filtrate is then concentrated under reduced pressure. The residue is taken up in ethyl acetate, washed with water and then with saturated potassium hydrogen carbonate solution and once again with water, and is then dried over magnesium sulphate and concentrated under reduced pressure. The residue is filtered through silica gel to yield the title product.

In Preparations 135 to 159, the procedure is as in Preparation 134, starting from the appropriate reactant.

Preparation 135

N-[2-(8-Allyl-7-bromo-1-naphthyl)ethyl]-N'-cyclobutylthiourea

Starting Compound: Preparation 16

Preparation 136

N-Cyclopropylmethyl-2-(7-bromo-1-naphthyl)acetamide

Starting Compound: Preparation 20

Preparation 137

N-[2-(7-Bromo-1-naphthyl)ethyl]-N-methyl-N'-propylurea

Starting Compound: Preparation 25

Preparation 138

Methyl 2-(7-bromo-1-naphthyl)-3-[(2,2,2-trifluoroacetyl)amino]propanoate

Starting Compound: Preparation 30

Preparation 139

N-[3-(7-Bromo-1-naphthyl)propyl]-1-cyclohexanecarboxamide

Starting Compound: Preparation 34

Preparation 140

N-[2-(2-Bromo-1-naphthyl)ethyl]-2,2,2-trifluoroacetamide

Starting Compound: Preparation 36

Preparation 141

N-[2-(3-Benzoyl-7-bromo-1-naphthyl)ethyl]-N'-propylurea

Starting Compound: Preparation 42

Preparation 142

N-[3-(5-Bromobenzo[b]furan-3-yl)propyl]acetamide

Starting Compound: Preparation 52

Preparation 143

N-[(2-Benzyl-5-bromobenzo[b]thiophen-3-yl)methyl]acetamide

Starting Compound: Preparation 59

Preparation 144

N-[2-(4-Allyl-5-bromobenzo[b]thiophen-3-yl)ethyl]benzamide

Starting Compound: Preparation 61

Preparation 145

N-[2-(5-Bromo-1H-3-indolyl)ethyl]-2-morpholinoacetamide

Starting Compound: Preparation 64

Preparation 146

N-[2-(5-Bromo-2-(4-fluorobenzyl)-1-methyl-1H-pyrrolo[2,3-b]pyridin-3-yl)ethyl]acetamide Starting Compound: Preparation 69

Preparation 147

N-[2-(6-Bromo-1H-benzo[b]imidazol-1-yl)ethyl]-1-cyclopropane-carboxamide

Starting Compound: Preparation 78

Preparation 148

N-[(6-Bromo-3,4-dihydro-2H-3-chromenyl)methyl]acetamide

Starting Compound: Preparation 79

Preparation 149

N-[2-(6-Bromo-3,4-dihydro-2H-4-chromenyl)ethyl]-2-phenylacetamide

Starting Compound: Preparation 86

Preparation 150

N-[(6-Bromo-2-phenyl-2H-3-chromenyl)methyl]acetamide

Starting Compound: Preparation 90

Preparation 151

N-[2-(6-Bromo-3,4-dihydro-2H-4-thiochromenyl)ethyl]acetamide

Starting Compound: Preparation 92

Preparation 152

N-[2-(7-Bromo-1,4-benzodioxin-2-yl)ethyl]-N'-propylurea

Starting Compound: Preparation 96

Preparation 153

N-[2-(6-Bromo-2,3-dihydro-1,4-benzodioxin-5-yl)ethyl]acetamide

Starting Compound: Preparation 99

Preparation 154

N-[(9-Bromo-2,3-dihydro-1H-benzo[f]chromen-2-yl)methyl]-2-cyclopropylacetamide

Starting Compound: Preparation 103

Preparation 155

N-(4-Bromo-2,3-dihydro-1H-2-phenalenyl)-N'-cyclopropylthiourea

Starting Compound: Preparation 109

Preparation 156

N-(6-Bromo-1,3,4,5-tetrahydrobenzo[cd]indol-4-yl)acetamide

Starting Compound: Preparation 115

Preparation 157

N-Cyclobutyl-6-bromo-4,5-dihydro-3H-benzo[cd]isobenzofuran-4-carboxamide

Starting Compound: Preparation 118

Preparation 158

N-[2-(7-Bromo-3-naphthyl)ethyl]heptanamide

Starting Compound: Preparation 122

Preparation 159

N-{2-[7-Bromo-3-(3-phenyl-2-propenyl)-1-naphthyl]ethyl}-2-cyclohexylacetamide

Starting Compound: Preparation 124

Preparation 160

N-[2-(7-Iodo-1-naphthyl)ethyl]-2-phenylacetamide

A mixture of the product obtained in Preparation 134 (2 mmol), potassium iodide (30 mmol) and copper(I) iodide (10 mmol) in hexamethylphosphoramide (6 ml) is heated at 150–160° C., with stirring, under a nitrogen atmosphere until 90% conversion has been achieved (monitored by TLC). Then, dilute hydrochloric acid, and then ether, are added and the mixture is then filtered to remove the insoluble copper(I) salts. The organic phase is separated off, washed with sodium sulphite solution and with water, dried over magnesium sulphate and evaporated to yield a residue which is chromatographed on silica gel to yield the title product.

In Preparations 161 to 185 the procedure is as in Preparation 160, but the product of Preparation 134 is replaced by the appropriate substrate.

Preparation 161

N-[2-(8-Allyl-7-iodo-1-naphthyl)ethyl]-N'-cyclobutylthiourea

Starting Compound: Preparation 135

Preparation 162

N-Cyclopropylmethyl-2-(7-iodo-1-naphthyl)acetamide

Starting Compound: Preparation 136

Preparation 163

N-[2-(7-Iodo-1-naphthyl)ethyl]-N-methyl-N'-propylurea

Starting Compound: Preparation 137

Preparation 164

Methyl 2-(7-iodo-1-naphthyl)-3-[(2,2,2-trifluoroacetyl)amino]propanoate

Starting Compound: Preparation 138

Preparation 165

N-[3-(7-Iodo-1-naphthyl)propyl]-1-cyclohexanecarboxamide

Starting Compound: Preparation 139

Preparation 166

N-[2-(2-Iodo-1-naphthyl)ethyl]-2,2,2-trifluoroacetamide

Starting Compound: Preparation 140

Preparation 167

N-[2-(3-Benzoyl-7-iodo-1-naphthyl)ethyl]-N'-propylurea

Starting Compound: Preparation 141

Preparation 168

N-[3-(5-Iodobenzo[b]furan-3-yl)propyl]acetamide

Starting Compound: Preparation 142

Preparation 169

N-[(2-Benzyl-5-iodobenzo[b]thiophen-3-yl)methyl]acetamide

Starting Compound: Preparation 143

Preparation 170

N-[2-(4-Allyl-5-iodobenzo[b]thiophen-3-yl)ethyl]benzamide

Starting Compound: Preparation 144

Preparation 171

N-[2-(5-Iodo-1H-3-indolyl)ethyl]-2-morpholinoacetamide

Starting Compound: Preparation 145

Preparation 172

N-[2-(5-Iodo-2-(4-fluorobenzyl)-1-methyl-1H-pyrrolo[2,3-b]pyridin-3-yl)-ethyl]acetamide Starting Compound: Preparation 146

Preparation 173

N-[2-(6-Iodo-1H-benzo[d]imidazol-1-yl)ethyl]-1-cyclopropane-carboxamide

Starting Compound: Preparation 147

Preparation 174

N-[(6-Iodo-3,4-dihydro-2H-3-chromenyl)methyl]acetamide

Starting Compound: Preparation 148

Preparation 175

N-[2-(6-Iodo-3,4-dihydro-2H-4-chromenyl)ethyl]-2-phenylacetamide

Starting Compound: Preparation 149

Preparation 176

N-[(6-Iodo-2-phenyl-2H-3-chromenyl)methyl]acetamide

Starting Compound: Preparation 150

Preparation 177

N-[2-(6-Iodo-3,4-dihydro-2H-4-thiochromenyl)ethyl]acetamide

Starting Compound: Preparation 151

Preparation 178

N-[2-(7-Iodo-1,4-benzodioxin-2-yl)ethyl]-N'-propylurea

Starting Compound: Preparation 152

Preparation 179

N-[2-(6-Iodo-2,3-dihydro-1,4-benzodioxin-5-yl)ethyl]acetamide

Starting Compound: Preparation 153

Preparation 180

N-[(9-Iodo-2,3-dihydro-1H-benzo[f]chromen-2-yl)methyl]-2-cyclopropylacetamide

Starting Compound: Preparation 154

Preparation 181

N-(4-Iodo-2,3-dihydro-1H-2-phenalenyl)-N'-cyclopropylthiourea

Starting Compound: Preparation 155

Preparation 182

N-(6-Iodo-1,3,4,5-tetrahydrobenzo[cd]indol-4-yl)acetamide

Starting Compound: Preparation 156

Preparation 183

N-Cyclobutyl-6-iodo-4,5-dihydro-3H-benzo[cd]isobenzofuran-4-carboxamide

Starting Compound: Preparation 157

Preparation 184

N-[2-(7-Iodo-3-naphthyl-1-naphthyl)ethyl]heptanamide

Starting Compound: Preparation 158

Preparation 185

N-{2-[7-Iodo-3-(3-phenylpropenyl)-1-naphthyl]ethyl}-2-cyclohexylacetamide

Starting Compound: Preparation 159

In Preparations 186 to 197 the procedure is as in Preparation 134, starting from the appropriate substrate.

Preparation 186

N-[2-(7-Bromo-1-naphthyl)ethyl]-2-bromoacetamide

Starting Compound: Preparation 8

Preparation 187

N-[2-(7-Bromo-8-hexyl-1-naphthyl)ethyl]-2-phenylacetamide

Starting Compound: Preparation 15

Preparation 188

N-Cyclohexyl-4-(7-bromo-1-naphthyl)butanamide

Starting Compound: Preparation 21

Preparation 189

N-[3-(7-Bromo-1-naphthyl)propyl]acetamide

Starting Compound: Preparation 33

Preparation 190

N-[2-(2-Bromo-1-naphthyl)-1-methylethyl]propanamide

Starting Compound: Preparation 39

Preparation 191

N-{2-[7-Bromo-3-(cyclopropylmethyl)-1-naphthyl]ethyl}acetamide

Starting Compound: Preparation 50

Preparation 192

N-Methyl-3-(5-bromobenzo[b]furan-3-yl)butanamide

Starting Compound: Preparation 54

Preparation 193

N-[2-(5-Bromothieno[3,2-b]pyridin-3-yl)ethyl]acetamide

Starting Compound: Preparation 60

Preparation 194

N-[2-(5-Bromo-1H-3-indolyl)ethyl]benzamide

Starting Compound: Preparation 66

Preparation 195

N-[2-(2-Benzyl-5-bromobenzo[b]furan-3-yl)ethyl]-1-cyclopropane-carboxamide

Starting Compound: Preparation 77

Preparation 196

N-[(6-Bromo-2-phenyl-2H-3-chromenyl)methyl]butanamide

Starting Compound: Preparation 91

Preparation 197

N-(4,9-Dibromo-2,3-dihydro-1H-2-phenalenyl)acetamide

Starting Compound: Preparation 111

In Preparations 198 to 209 the procedure is as in Preparation 160, starting from the appropriate substrate.

Preparation 198

N-[2-(7-Iodo-1-naphthyl)ethyl]-2-bromoacetamide

Starting Compound: Preparation 186

Preparation 199

N-[2-(7-Iodo-8-hexyl-1-naphthyl)ethyl]-2-phenylacetamide

Starting Compound: Preparation 187

Preparation 200

N-Cyclohexyl-4-(7-iodo-1-naphthyl)butanamide

Starting Compound: Preparation 188

Preparation 201

N-[3-(7-Iodo-1-naphthyl)propyl]acetamide

Starting Compound: Preparation 189

Preparation 202

N-[2-(2-Iodo-1-naphthyl)-1-methylethyl]propanamide

Starting Compound: Preparation 190

Preparation 203

N-{2-[7-Iodo-3-(cyclopropylmethyl)-1-naphthyl]ethyl}acetamide

Starting Compound: Preparation 191

Preparation 204

N-Methyl-4-(5-iodobenzo[b]furan-3-yl)butanamide

Starting Compound: Preparation 192

Preparation 205

N-[2-(5-Iodothieno[3,2-b]pyridin-3-yl)ethyl]acetamide

Starting Compound: Preparation 193

Preparation 206

N-[2-(5-Iodo-1H-3-indolyl)ethyl]benzamide

Starting Compound: Preparation 194

Preparation 207

N-[2-(2-Benzyl-5-iodobenzo[b]furan-3-yl)ethyl]-1-cyclopropane-carboxamide

Starting Compound: Preparation 195

Preparation 208

N-[(6-Iodo-2-phenyl-2H-3-chromenyl)methyl]butanamide

Starting Compound: Preparation 196

Preparation 209

N-[4,9-Diiodo-2,3-dihydro-1H-2-phenalenyl)acetamide

Starting Compound: Preparation 197

In Preparations 210 to 223 the procedure is as in Preparation 2.

Preparation 210

N-[2-(5-Hydroxy-2-phenylbenzo[b]thiophen-3-yl)ethyl]acetamide

Preparation 211

N-[2-(5-Hydroxybenzo[b]thiophen-3-yl)ethyl]acetamide

Preparation 212

N-[2-(5-Hydroxybenzo[b]thiophen-3-yl)ethyl]acrylamide

Preparation 213

N-[2-(5-Hydroxybenzo[b]thiophen-3-yl)ethyl]-2,2,2-trifluoroacetamide

Preparation 214

N-[2-(5-Hydroxybenzo[b]thiophen-3-yl)ethyl]-1-cyclopropane-carboxamide

Preparation 215

N-[2-(5-Hydroxybenzo[b]thiophen-3-yl)ethyl]butanamide

Preparation 216

N-[2-(5-Hydroxybenzo[b]thiophen-3-yl)ethyl]-N'-methylurea

Preparation 217

N-[2-(5-Hydroxybenzo[b]thiophen-3-yl)ethyl]benzamide

Preparation 218

N-[2-(5-Hydroxybenzo[b]thiophen-3-yl)ethyl]-2-(3,4-dichlorophenyl)acetamide

Preparation 219

N-[2-(7-Hydroxy-1,2,3,4-tetrahydro-1-naphthyl)ethyl]acetamide

Preparation 220

N-(8-Hydroxy-5-methyl-1,2,3,4-tetrahydro-2-naphthyl)acetamide

Preparation 221

N-2,5-Dimethyl-8-hydroxy-1,2,3,4-tetrahydro-2-naphthalenecarboxamide

Preparation 222

N-[2-(5-Hydroxybenzo[b]thiophen-3-yl)ethyl]-3-butenamide

Preparation 223

N-[2-(6-Hydroxy-2,3-dihydro-1H-1-indenyl)ethyl]acetamide

Preparation 224

N-[2-(5-Chloro-2-phenylbenzo[b]thiophen-3-yl)ethyl]acetamide

Step A: 1-[(4-Chlorophenyl)thio]-1-phenylacetone

In a 100 ml round-bottomed flask, 1 eq. of 4-chlorothiophenol is dissolved in 4 eq. of pyridine and 50 ml of anhydrous ether, with magnetic stirring. 1.2 eq. of bromophenylacetone are then added dropwise and stirring is then carried out overnight at ambient temperature. The reaction mixture is then poured onto ice-cold water and is extracted with ethyl acetate. The organic phase is washed with 1M HCl solution and then with water, is dried over MgSO$_4$ and is evaporated under reduced pressure. The residue obtained is purified by chromatography on a silica gel column.

Step B: 5-Chloro-3-methyl-2-phenyl-1-benzothiophene

In a 100 ml round-bottomed flask, 1 eq. of the compound obtained in Step A, 10 eq. of polyphosphoric acid and 1 eq. of phosphoric anhydride are mixed together. The mixture is stirred for 3 hours at 180° C. and is then hydrolysed. Extraction with ether is carried out, and the organic phase is washed with water, dried over MgSO$_4$ and evaporated under reduced pressure. The residue obtained is purified by chromatography on a silica gel column.

Melting point=108–109° C.

Step C: 3-(Bromomethyl)-5-chloro-2-phenyl-1-benzothiophene

In a 100 ml round-bottomed flask, 1 eq. of the compound obtained in Step B is dissolved in 20 ml of CCl$_4$. 1 eq. of N-bromosuccinimide and 0.04 eq. of benzoyl peroxide are then added, and the mixture is irradiated by means of a halogen lamp and maintained at reflux for 4 hours. At the end of the reaction, the insoluble material is filtered off, and the carbon tetrachloride is evaporated off. The residue obtained is purified by chromatography on a silica gel column.

Melting point=128–129° C.

Step D: 2-(5-Chloro-2-phenyl-1-benzothiophen-3-yl)acetonitrile 1.2 eq. of NaCN are suspended in 20 ml of dimethyl sulphoxide. The mixture is heated at 60° C. for 30 minutes and then 1 eq. of the compound obtained in Step C is added gradually. The reaction mixture is stirred for 1 hour at 60° C. and is then hydrolysed. Extraction with ethyl acetate is carried out and the organic phase is washed with water, dried over MgSO$_4$ and evaporated under reduced pressure. The residue obtained is purified by chromatography on silica gel.

Melting point=156–157° C.

Step E: 2-(5-Chloro-2-phenyl-1-benzothiophen-3-yl)-1-ethanamine Hydrochloride 3 eq. of diborane in tetrahydrofuran and 1 eq. of the nitrile obtained in Step D are introduced into a 100 ml round-bottomed flask, and the mixture is then heated at reflux for 2 hours. After cooling, 15 eq. of 6M HCl are added and the tetrahydrofuran is evaporated off under reduced pressure. The precipitate formed is filtered off and recrystallised.

Melting point=291–292° C.

Elemental Microanalysis:

|  | C | H | N |
|---|---|---|---|
| % calculated | 52.12 | 4.10 | 3.78 |
| % found | 52.48 | 4.42 | 3.37 |

Step F: N-[2-(5-Chloro-2-phenylbenzo[b]thiophen-3-yl)ethyl]acetamide

The compound obtained in Step E is dissolved in a mixture of water/dichloromethane (2/3); 2 eq. of potassium carbonate are then added and 2 eq. acetyl chloride are added dropwise. After stirring for 2 hours at ambient temperature, the 2 phases are separated; the organic phase is washed with 1M HCl and then with water, until the washing waters are neutral, and is then dried over MgSO$_4$ and evaporated. The residue obtained is purified by chromatography on silica gel.

Melting point=147–149° C.

Elemental Microanalysis:

|  | C | H | N |
|---|---|---|---|
| % calculated | 65.54 | 4.89 | 4.25 |
| % found | 65.55 | 4.90 | 4.25 |

Preparations 225 to 235 are obtained by proceeding as in Preparation 224.

Preparation 225

N-[2-(5-Chlorobenzo[b]thiophen-3-yl)ethyl]acetamide

Melting point=129–130° C.

Elemental Microanalysis:

|  | C | H | N |
|---|---|---|---|
| % calculated | 56.80 | 4.77 | 5.52 |
| % found | 56.73 | 4.72 | 5.44 |

Preparation 226

N-[2-(5-Chlorobenzo[b]thiophen-3-yl)ethyl]acrylamide

Melting point=111–113° C.

Elemental Microanalysis:

|  | C | H | N |
|---|---|---|---|
| % calculated | 58.75 | 4.55 | 5.27 |
| % found | 58.65 | 4.58 | 5.14 |

Preparation 227

N-[2-(5-Chlorobenzo[b]thiophen-3-yl)ethyl]-2,2,2-trifluoroacetamide

Melting point=132–134° C.

Elemental Microanalysis:

|  | C | H | N |
|---|---|---|---|
| % calculated | 46.83 | 2.95 | 4.55 |
| % found | 47.10 | 2.99 | 4.47 |

Preparation 228

N-[2-(5-Chlorobenzo[b]thiophen-3-yl)ethyl]-1-cyclopropanecarboxamide

Melting point=161–163° C.

Elemental Microanalysis:

|  | C | H | N |
|---|---|---|---|
| % calculated | 60.10 | 5.04 | 5.01 |
| % found | 60.23 | 5.14 | 4.93 |

Preparation 229

N-[2-(5-Bromobenzo[b]thiophen-3-yl)ethyl]acetamide

Melting point=134–136° C.

Elemental Microanalysis:

|  | C | H | N |
|---|---|---|---|
| % calculated | 48.33 | 4.06 | 4.70 |
| % found | 48.65 | 4.14 | 4.72 |

Preparation 230

N-[2-(5-Bromobenzo[b]thiophen-3-yl)ethyl]-2,2,2-trifluoroacetamide

Melting point=144.5–145.5° C.

Elemental Microanalysis:

|  | C | H | N |
|---|---|---|---|
| % calculated | 40.92 | 2.58 | 3.98 |
| % found | 41.09 | 2.66 | 4.05 |

Preparation 231

N-[2-(5-Bromobenzo[b]thiophen-3-yl)ethyl]butanamide

Melting point=124–125° C.

Elemental Microanalysis:

|  | C | H | N |
|---|---|---|---|
| % calculated | 51.54 | 4.94 | 4.29 |
| % found | 51.41 | 5.01 | 4.35 |

Preparation 232

N-[2-(5-Bromobenzo[b]thiophen-3-yl)ethyl]-N'-methylurea

Melting point=174–178° C.
Elemental Microanalysis:

|  | C | H | N |
|---|---|---|---|
| % calculated | 46.01 | 4.18 | 8.94 |
| % found | 45.64 | 4.17 | 8.86 |

Preparation 233

N-[2-(5-Bromobenzo[b]thiophen-3-yl)ethyl]benzamide

Melting point=142–145° C.
Elemental Microanalysis:

|  | C | H | N |
|---|---|---|---|
| % calculated | 56.67 | 3.92 | 3.89 |
| % found | 56.76 | 3.94 | 3.82 |

Preparation 234

N-[2-(5-Bromobenzo[b]thiophen-3-yl)ethyl]-2-(3,4-dichlorophenyl)acetamide

Melting point=170–171° C.
Elemental Microanalysis:

|  | C | H | N |
|---|---|---|---|
| % calculated | 48.78 | 3.18 | 3.16 |
| % found | 48.88 | 3.20 | 3.38 |

Preparation 235

N-[2-(5-Bromobenzo[b]thiophen-3-yl)ethyl]-3-butenamide

Melting point=90–91° C.
Preparations 236 to 238 are obtained by proceeding as in Preparation 134.

Preparation 236

N-[2-(7-Bromo-1,2,3,4-tetrahydro-1-naphthyl)ethyl]acetamide

Preparation 237

N-(8-Bromo-5-methyl-1,2,3,4-tetrahydro-2-naphthyl)acetamide

Preparation 238

N-2,5-Dimethyl-8-bromo-1,2,3,4-tetrahydro-2-naphthalenecarboxamide

Preparation 239

N-[2-(7-Fluoro-1,2,3,4-tetrahydro-1-naphthyl)ethyl]acetamide

Step A: 4-(4-Fluorophenyl)-4-oxobutanoic acid 0.4 mol of aluminium chloride and 94 ml of fluorobenzene are introduced into a 500 ml flask with a ground neck and then 0.2 mol of succinic anhydride is added in small portions, with magnetic stirring. The mixture is heated at 60° C. for 5 hours and is then cooled and poured into ice-cold water. After acidification using 3M HCl solution, the precipitate formed is filtered off under suction, washed with cyclohexane and recrystallised.
Melting point=102–103° C.

Step B: Methyl 4-(4-fluorophenyl)-4-oxobutanoate

In a 500 ml round-bottomed flask, 0.092 mol of the compound obtained in Step A is dissolved in 200 ml of methanol The mixture is cooled using an ice bath and 0.138 mol of thionyl chloride is added dropwise. The reaction mixture is stirred for 5 hours at ambient temperature; the methanol is then evaporated off and the solid obtained is taken up in petroleum ether, filtered off under suction and used directly in the following Step.

Step C: Methyl 4-(4-fluorophenyl)butanoate

In a 500 ml round-bottomed flask, 0.095 mol of the compound obtained in Step B is dissolved in 250 ml of methanol. 1 g of 10% activated palladium-on-carbon is added and magnetic stirring is carried out under a hydrogen atmosphere for 12 hours. The palladiated carbon is then filtered off, and the methanol is evaporated off under reduced pressure. The oil obtained is purified by chromatography on silica gel.

Step D: 4-(4-Fluorophenyl)butanoic acid 0.076 mol of the compound obtained in Step C is introduced in a 500 ml round-bottomed flask, and then 250 ml of water and 0.152 mol of NaOH are added. The reaction mixture is stirred for 12 hours at ambient temperature. The reaction mixture is then acidified with 3M HCl and is extracted twice with ethyl ether. The organic phase is dried over $MgSO_4$ and evaporated under reduced pressure to obtain the title product in the form of a white solid.
Melting point=38° C.

Step E: 7-Fluoro-3,4-dihydro-1(2H)-naphthalenone 0.055 mol of the compound obtained in Step D is introduced into a 500 ml round-bottomed flask together with 100 g of polyphosphoric acid. The reaction mixture is heated at 60° C. for 4 hours. The mixture is then cooled and poured into water; the precipitate formed is then dried and recrystallised.
Melting point=57° C.

Step F: 2-[7-Fluoro-3,4-dihydro-1(2H)-naphthalenylidene]acetonitrile 1.6 eq. of NaH are suspended in 130 ml of anhydrous THF under a nitrogen atmosphere in a 250 ml three-necked flask. The mixture is cooled in a bath of ice/salt and 1.6 eq. of diethyl cyanomethylenephosphonate in 40 ml of THF are added dropwise. The reaction mixture is stirred for 45 minutes and then, whilst still cold, 1 eq. of the compound obtained in Step E, in 70 ml of THF, is added dropwise. The mixture is stirred for 4 hours and is then poured onto a mixture of ice/water, acidified with 3M HCl solution and extracted 3 times with ethyl ether. The organic phase is dried over MgSO$_4$ and evaporated under reduced pressure; the residue obtained is recrystallised.

Melting point=124–125° C.

Step G: 2-(7-Fluoro-1,2,3,4-tetrahydro-1-naphthyl)-1-ethylamine hydrochloride 0.011 mol of the compound obtained in Step F is dissolved in 100 ml of 95° alcohol and introduced into a 400 ml autoclave; 0.5 g of Raney nickel is then added. The solution is saturated with ammonia gas, and hydrogen is introduced until a pressure of 50 bars is obtained. The reaction mixture is stirred for 5 hours at 60° C. and is then cooled, filtered and evaporated under reduced pressure. The oil obtained is dissolved in anhydrous ethyl ether and a solution of ethyl ether saturated with gaseous hydrogen chloride is added dropwise. The precipitate formed is filtered off under suction and recrystallised.

Melting point=121–122° C.

Step H: N-[2-(7-Fluoro-1,2,3,4-tetrahydro-1-naphthyl) ethyl]acetamide 1 eq. of the compound obtained in Step G is dissolved in 4 ml of pyridine and is cooled in an ice bath before adding 3 eq. of acetic anhydride dropwise. The reaction mixture is stirred for 5 hours at ambient temperature and is then poured into 3M HCl solution and extracted with ethyl ether. The organic phase is washed with 10% potassium carbonate solution and then with water, dried over MgSO$_4$ and evaporated under reduced pressure. The oil obtained is precipitated from a mixture of ethyl ether/petroleum ether (1/2) and the precipitate formed is filtered off under suction and recrystallised.

Melting point=58–59° C.
Elemental Microanalysis:

|  | C | H | N |
|---|---|---|---|
| % calculated | 71.40 | 7.71 | 5.95 |
| % found | 71.40 | 7.79 | 5.66 |

Preparation 240

N-[2-(6-Bromo-2,3-dihydro-1H-1-indenyl)ethyl] acetamide

The procedure is as in Preparation 134.

Preparation 241

N-[2-(6-Iodo-2,3-dihydro-1H-1-indenyl)ethyl]acetamide

The procedure is as in Preparation 160.

Preparation 242

N-[2-(7-Bromo-3-phenyl-1-naphthyl)ethyl]acetamide

The procedure is as in Preparation 134.

Preparation 243

N-[2-(7-Iodo-3-phenyl-1-naphthyl)ethyl]acetamide

The procedure is as in Preparation 160.

Preparation 244

N-[2-(7-Iodo-1,2,3,4-tetrahydro-1-naphthyl)ethyl] acetamide

The procedure is as in Preparation 160.

Preparation 245

N-[2-(5-Bromobenzo[b]furan-3-yl)ethyl]acetamide

The procedure is as in Preparation 134.

Preparation 246

N-[2-(5-Iodobenzo[b]furan-3-yl)ethyl]acetamide

The procedure is as in Preparation 160.

Preparations 247 to 257 are obtained by proceeding as in Preparation 224.

Preparation 247

N-[2-(5-Bromo-1-benzothiophen-3-yl)ethyl]-2-phenylacetamide

Melting point=147–148.2° C.
Elemental Microanalysis:

|  | C | H | N |
|---|---|---|---|
| % calculated | 57.76 | 4.31 | 3.74 |
| % found | 57.77 | 4.33 | 3.85 |

Preparation 248

N-[2-(5-Bromo-1-benzothiophen-3-yl)ethyl]-3,4-dichlorobenzamide

Melting point=170–171° C.
Elemental Microanalysis:

|  | C | H | N |
|---|---|---|---|
| % calculated | 48.78 | 3.18 | 3.16 |
| % found | 48.88 | 3.20 | 3.38 |

Preparation 249

N-[2-(5-Bromo-1-benzothiophen-3-yl)ethyl]-2-furamide

Melting point=87–88° C.

Preparation 250

N-[2-(5-Chloro-1-benzothiophen-3-yl)ethyl]-2-butynamide

Melting point=79–80° C.

Preparation 251

4-Chloro-N-[2-(5-chloro-1-benzothiophen-3-yl)ethyl]butanamide

Melting point=83–84° C.

Preparation 252

N-[2-(5-Chloro-1-benzothiophen-3-yl)ethyl]-2-furamide

Melting point=70–71° C.

Preparation 253

N-[2-(5-Bromo-2-phenyl-1-benzothiophen-3-yl)ethyl]acetamide

Melting point=140–141° C.

Preparation 254

-[2-(5-Chloro-1-benzothiophen-3-yl)ethyl]-3-phenyl-2-propenamide

Melting point=162–163° C.

Preparation 255

N-[2-(5-Bromo-1-benzothiophen-3-yl)ethyl]-3-phenyl-2-propenamide

Melting point=152–153° C.

Preparation 256

N-[2-(5-Chloro-1-benzothiophen-3-yl)ethyl]-4-phenyl-3-butenamide

Melting point=116–117° C.
Elemental Microanalysis:

|  | C | H | N |
|---|---|---|---|
| % calculated | 67.49 | 5.09 | 3.93 |
| % found | 66.99 | 5.22 | 3.97 |

Preparation 257

N-[2-(5-Bromo-1-benzothiophen-3-yl)ethyl]-4-phenyl-3-butenamide

Melting point=130–131° C.
Elemental Microanalysis:

|  | C | H | N |
|---|---|---|---|
| % calculated | 60.00 | 4.53 | 3.50 |
| % found | 60.19 | 4.61 | 3.51 |

Preparation 258

N-[2-(5-Chloro-1-benzothiophen-3-yl)ethyl]-3-butenamide

Melting point=76–77° C.
Elemental Microanalysis:

|  | C | H | N |
|---|---|---|---|
| % calculated | 51.86 | 4.35 | 4.32 |
| % found | 51.86 | 4.30 | 4.16 |

Preparation 259

N-[2-(5-Bromo-2-phenyl-1-benzothiophen-3-yl)ethyl]-3-butenamide

Melting point=109–111° C.
Elemental Microanalysis:

|  | C | H | N |
|---|---|---|---|
| % calculated | 60.01 | 4.53 | 3.50 |
| % found | 59.97 | 4.48 | 3.24 |

Preparation 260

2-Bromo-N-[2-(5-chloro-1-benzothiophen-3-yl)ethyl]acetamide

Preparation 261

2-Bromo-N-[2-(5-bromo-1-benzothiophen-3-yl)ethyl]acetamide

EXAMPLE 1

N-{2-[7-(Methylthio)-1-naphthyl]ethyl}acetamide

At 0° C. and with vigorous stirring, potassium carbonate (1.98 mmol) and acetyl chloride (1.82 mmol) are added to a solution of the product obtained in Preparation 1 (1.65 mmol) in a mixture of dichloromethane and water (2/1 ml). The reaction mixture is stirred for 30 minutes and the two phases are then separated. The organic phase is washed with water, dried over magnesium sulphate and evaporated. The residue is purified by chromatography on silica gel (eluant: acetone/toluene/cyclohexane 30/50/20) and is then recrystallised from a mixture of cyclohexane and toluene to yield the title acetamide in the form of a white solid.

Melting point=104–106° C.
Elemental Microanalysis:

|  | C | H | N |
|---|---|---|---|
| % calculated | 69.49 | 6.60 | 5.40 |
| % found | 69.78 | 6.44 | 5.36 |

EXAMPLE 2

N-{2-[7-(Methylthio)-1-naphthyl]ethyl}butanamide

By proceeding as in Example 1, but replacing the acetyl chloride by butanoyl chloride, the title product is obtained.
Melting point=55–57° C.
Elemental Microanalysis:

|  | C | H | N |
|---|---|---|---|
| % calculated | 71.04 | 7.36 | 4.87 |
| % found | 70.87 | 7.52 | 5.15 |

EXAMPLE 3

N-{2-[7-(Methylthio)-1-naphthyl]ethyl}-1-cyclopropanecarboxamide

By proceeding as in Example 1, but replacing the acetyl chloride by cyclopropanecarboxylic acid chloride, the title product is obtained in the form of a white solid.
Melting point=96–98° C.
Elemental Microanalysis:

|  | C | H | N |
|---|---|---|---|
| % calculated | 71.54 | 6.71 | 4.91 |
| % found | 71.34 | 6.56 | 4.95 |

EXAMPLE 4

N-{2-[7-(Methylthio)-1-naphthyl]ethyl}-2,2,2-trifluoroacetamide

At 0° C., pyridine (2.21 mmol) and trifluoroacetic anhydride (1.61 mmol) are added in succession to a solution of the product obtained in Preparation 1 (1.47 mmol) in 5 ml of dichloromethane. Stirring is carried out for 16 hours at ambient temperature and the reaction mixture is then washed with water, dried over magnesium sulphate and evaporated. The residue is chromatographed on silica gel (eluant: petroleum ether/dichloromethane 50/50) and is then recrystallised from a mixture of ethanol and water to yield the title product in the form of a white solid.
Melting point=94–96° C.
Elemental Microanalysis:

|  | C | H | N |
|---|---|---|---|
| % calculated | 57.50 | 4.50 | 4.47 |
| % found | 57.11 | 4.49 | 4.49 |

EXAMPLE 5

N-Methyl-N'-{2-[7-(methylthio)-1-naphthyl]ethyl}urea

At ambient temperature, methyl isocyanate (2.20 mmol) is added to a solution of the product obtained in Preparation 1 (1.84 mmol) in 8 ml of pyridine. Stirring is carried out for 16 hours at ambient temperature and the reaction mixture is then hydrolysed and subsequently extracted with ethyl acetate. The organic phase is washed with 3N hydrochloric acid solution and then with water, dried over magnesium sulphate and evaporated. The residue is purified by chromatography on silica gel (eluant: acetone/toluene/cyclohexane 40/40/20) and is then recrystallised from toluene to yield the title product in the form of a white solid.
Melting point=156–158° C.
Elemental Microanalysis:

|  | C | H | N |
|---|---|---|---|
| % calculated | 65.66 | 6.61 | 10.21 |
| % found | 65.61 | 6.49 | 9.92 |

EXAMPLE 6

N-{2-[3-Benzoyl-7-(methylthio)-1-naphthyl]ethyl}acetamide

At 0° C., benzoyl chloride (4.44 mmol) is added dropwise to a suspension of aluminium trichloride (7.40 mmol) in 15 ml of dichloromethane. The reaction mixture is stirred at 0° C. for 30 minutes; the compound obtained in Example 1, dissolved in 10 ml of dichloromethane, is then added dropwise and stirring is continued for 16 hours. After hydrolysis, the two phases are separated; the organic phase is washed with water, dried over magnesium sulphate and evaporated. The residue is chromatographed on silica gel (eluant: acetone/toluene/cyclohexane 30/50/20) and is recrystallised from a mixture of cyclohexane and toluene to yield the title product in the form of a white solid.
Melting point=126–128° C.
Elemental Microanalysis:

|  | C | H | N |
|---|---|---|---|
| % calculated | 72.70 | 5.82 | 3.85 |
| % found | 72.66 | 5.95 | 3.84 |

EXAMPLE 7

N-{2-[3-Benzyl-7-(methylthio)-1-naphthyl]ethyl)acetamide

A solution of the product obtained in Example 6 (2.06 mmol) in trifluoroacetic acid (20.6 mmol) is brought to 0° C. and then triethylsilane hydride (6.18 mmol) is added dropwise. Stirring is carried out at ambient temperature for one week and a fourth equivalent of triethylsilane hydride is then added. The reaction mixture is stirred for 24 hours more and is then hydrolysed and extracted with ethyl acetate. The organic phase is washed with water, dried over magnesium sulphate and evaporated. The residue is chromatographed on silica gel (eluant: acetone/toluene/cyclohexane 30/50/20) and is then recrystallised twice from toluene to yield the title product in the form of a white solid.
Melting point=126–128° C.
Elemental Microanalysis:

|  | C | H | N |
|---|---|---|---|
| % calculated | 75.61 | 6.63 | 4.01 |
| % found | 75.72 | 6.70 | 4.04 |

EXAMPLE 8

N-{2-[7-(Ethylthio)-1-naphthyl]ethyl}acetamide

The product obtained in Preparation 2 (0.01 mmol), diluted with trifluoromethanesulphonic acid (0.03 mmol), is introduced into a two-necked flask under a nitrogen atmosphere and with stirring. Ethanethiol (0.015 mmol) is added and the mixture is heated at 65° C. for 2 hours with the aid of an oil bath. After cooling, the reaction mixture is poured into an ice/water mixture. The aqueous phase is extracted with ethyl acetate, and the organic phases are then washed successively with water, with 10% sodium hydroxide solution and then again with water. After drying over magnesium sulphate and concentrating under reduced pressure, the residue is chromatographed on silica gel (eluant: dichloromethane/ethyl acetate 50/50) to yield the pure title product.

Melting point=65–66° C.
Elemental Microanalysis:

|  | C | H | N |
|---|---|---|---|
| % calculated | 70.29 | 7.00 | 5.12 |
| % found | 70.21 | 7.04 | 5.10 |

EXAMPLE 9

N-{2-[7-(Propylthio)-1-naphthyl]ethyl}acetamide

By proceeding as in Example 8, but replacing the ethanethiol by propanethiol, the title product is obtained in the form of an oil.

Elemental Microanalysis:

|  | C | H | N |
|---|---|---|---|
| % calculated | 71.04 | 7.36 | 4.87 |
| % found | 71.26 | 7.49 | 4.75 |

EXAMPLE 10

N-[2-(7-Mercapto-1-naphthyl)ethyl]benzamide

The product obtained in Preparation 5 (9 mmol) is added to a solution of potassium hydroxide (10 mmol) dissolved in 15 ml of water and 16 ml of tetrahydrofuran, with stirring. The solution is cooled using a bath of ice and salt, and dimethylthiocarbamoyl chloride (9 mmol) dissolved in tetrahydrofuran (15 ml) is added dropwise, without stirring. After stirring for half an hour, whilst maintaining the cold state, the reaction mixture is extracted with chloroform. The organic phases are combined, dried over magnesium sulphate, filtered and then concentrated under reduced pressure. The residue is taken up in diphenyl ether (10 ml) and is heated at reflux for one hour under a nitrogen atmosphere. The diphenyl ether is evaporated off under reduced pressure until a solution of approximately 2 ml is obtained. The 2 ml of distillate, whilst still hot, are poured with caution into 50 ml of hexane to yield, after cooling, a solid that is isolated by filtration. The solid thus collected is added to a solution of potassium hydroxide (380 mg) dissolved in a mixture of water/methanol (1 ml/10 ml). The solution is heated at reflux for 12 hours and is then cooled and concentrated under reduced pressure. The residue is taken up in 20 ml of chloroform and is extracted 3 times with water. The organic phase is dried over magnesium sulphate, filtered and concentrated under reduced pressure. The residue is chromatographed on silica gel to yield the title product.

Examples 11 to 36 are obtained by proceeding as in Example 10, starting from the appropriate hydroxylated compound.

EXAMPLE 11

N-[2-(7-Mercapto-1-naphthyl)ethyl]heptanamide

Starting Compound: Preparation 10

EXAMPLE 12

N-[2-(8-Allyl-7-mercapto-1-naphthyl)ethyl]-N'-cyclobutylthiourea

Starting Compound: Preparation 16

EXAMPLE 13

N-Cyclohexyl-4-(7-mercapto-1-naphthyl)butanamide

Starting Compound: Preparation 21

EXAMPLE 14

N-Methyl-N'-propyl-N-[2-(7-mercapto-1-naphthyl)ethyl]urea

Starting Compound: Preparation 25

EXAMPLE 15

N-Di-(4-chlorophenyl)methyl-N'-[2-(7-mercapto-1-naphthyl)ethyl]urea

Starting Compound: Preparation 27

EXAMPLE 16

N-[3-(7-Mercapto-1-naphthyl)propyl]-1-cyclohexanecarboxamide

Starting Compound: Preparation 34

EXAMPLE 17

N-[2-(2-Mercapto-1-naphthyl)ethyl]-2,2,2-trifluoroacetamide

Starting Compound: Preparation 36

EXAMPLE 18

N-[2-(3-Benzoyl-7-mercapto-1-naphthyl)ethyl]-N'-propylurea

Starting Compound: Preparation 42

EXAMPLE 19

N-[2-(3-Benzyl-7-mercapto-1-naphthyl)ethyl]-1-cyclohexanecarboxamide

Starting Compound: Preparation 48

EXAMPLE 20

N-[2-(5-Mercaptobenzo[b]furan-3-yl)ethyl]acetamide

Starting Compound: Preparation 56

EXAMPLE 21

N-[2-(4-Allyl-5-mercaptobenzo[b]thiophen-3-yl)ethyl]benzamide

Starting Compound: Preparation 61

EXAMPLE 22

N-{2-[2-(4-Fluorobenzyl)-1-methyl-5-mercapto-1H-pyrrolo[2,3-b]pyridin-3-yl]ethyl}acetamide Starting Compound: Preparation 69

EXAMPLE 23

N-[2-(2-Phenyl-5-mercapto-1H-pyrrolo[2,3-b]pyridin-3-yl)ethyl]-3-butenamide

Starting Compound: Preparation 73

EXAMPLE 24

N-[2-(2-Benzyl-5-mercaptobenzo[b]furan-3-yl)ethyl]-1-cyclopropane-carboxamide

Starting Compound: Preparation 77

EXAMPLE 25

N-[(6-Mercapto-3,4-dihydro-2H-4-chromenyl)methyl]acetamide

Starting Compound: Preparation 82

EXAMPLE 26

N-Methyl-3-(6-mercapto-2H-3-chromenyl)propanamide

Starting Compound: Preparation 89

EXAMPLE 27

N-[2-(6-Mercapto-3,4-dihydro-2H-4-thiochromenyl)ethyl]acetamide

Starting Compound: Preparation 92

EXAMPLE 28

N-[(3-Benzyl-7-mercapto-1,4-benzodioxin-2-yl)methyl]acetamide

Starting Compound: Preparation 94

EXAMPLE 29

N-[2-(6-Mercapto-2,3-dihydro-1,4-benzodioxin-5-yl)ethyl]acetamide

Starting Compound: Preparation 99

EXAMPLE 30

N-[2-(5-Mercaptobenzo[d]isoxazol-3-yl)ethyl]-1-cyclopropane-carboxamide

Starting Compound: Preparation 101

EXAMPLE 31

N-Methyl-9-mercaptobenzo-3H-benzo[f]chromene-2-carboxamide

Starting Compound: Preparation 106

EXAMPLE 32

N-Cyclohexyl-N'-(4-mercapto-2,3-dihydro-1H-2-phenalenyl)urea

Starting Compound: Preparation 110

EXAMPLE 33

N-[2-(4-Mercapto-2,3-dihydro-1H-1-phenalenyl)ethyl]-1-cyclopropane-carboxamide

Starting Compound: Preparation 113

EXAMPLE 34

N-{[2-(2-Furylmethyl)-5-mercaptobenzo[b]thiophen-3-yl]methyl}acetamide

Starting Compound: Preparation 119

EXAMPLE 35

N-{[2-(3-Phenyl-2-propenyl)-5-mercaptobenzo[b]thiophen-3-yl]methyl}-1-cyclobutanecarboxamide Starting Compound: Preparation 121

EXAMPLE 36

N-{[7-Mercapto-3-(2-thienyl)-1-naphthyl]methyl}butanamide

Starting Compound: Preparation 125

In Examples 37 to 170 the procedure is as in Example 8, but the ethanethiol is replaced by the appropriate thiol and the N-[2-(7-hydroxy-1-naphthyl)ethyl]acetamide by the appropriate hydroxylated compound.

(Note: When the thiol used is unstable, it is prepared extemporaneously and stored under argon.)

EXAMPLE 37

N-[2-[7-(Allylthio)-1-naphthyl]ethyl}-2-phenylacetamide

Starting Compounds: Preparation 3 and 2-propene-1-thiol

EXAMPLE 38

N-{2-[7-(Cyclohexylthio)-1-naphthyl]ethyl]-2-thiophenecarboxamide

Starting Compounds: Preparation 7 and Cyclohexanethiol

EXAMPLE 39

N-{2-[7-(Benzylthio)-1-naphthyl]ethyl}heptanamide

Starting Compounds: Preparation 10 and Benzylthiol

EXAMPLE 40

N-{2-[7-(2-Propynylthio)-1-naphthyl]ethyl}-2-bromoacetamide

Starting Compounds: Preparation 8 and 2-propyne-1-thiol

EXAMPLE 41

N-{2-[7-((4-Methylphenyl)thio)-1-naphthyl]ethyl}-3-(trifluoromethyl)benzamide

Starting Compounds: Preparation 6 and 4-methylphenylthiol

EXAMPLE 42

Methyl 2-{[8-(2-{[2-(2-oxotetrahydro-1H-1-pyrrolyl)acetyl]amino}ethyl)-2-naphthyl]thio}benzoate Starting Compounds: Preparation 4 and Methyl 2-mercaptobenzoate

EXAMPLE 43

N-{2-[7-((Cyclopropylmethyl)thio)-1-naphthyl]ethyl}-4-chlorobutanamide

Starting Compounds: Preparation 9 and Cyclopropylmethanethiol

EXAMPLE 44

N-{2-[8-Allyl-7-(isopropylthio)-1-naphthyl]ethyl}acetamide

Starting Compounds: Preparation 11 and Isopropanethiol

EXAMPLE 45

N-{2-[8-Allyl-7-(2-pyridylthio)-1-naphthyl]ethyl}heptanamide

Starting Compounds: Preparation 12 and 2-pyridinethiol

EXAMPLE 46

Methyl 4-{[8-(2-(acetylamino)ethyl)-1-propenyl-2-naphthyl]thio}butanoate

Starting Compounds: Preparation 13 and Methyl 4-mercaptobutanoate

EXAMPLE 47

N-{2-[7-(2-Butynylthio)-8-(2-propynyl)-1-naphthyl]ethyl}-2-acetamide

Starting Compounds: Preparation 14 and 2-propynyl-1-thiol

EXAMPLE 48

N-{2-[8-Hexyl-7-(hexylthio)-1-naphthyl]ethyl}-2-phenylacetamide

Starting Compounds: Preparation 15 and Hexanethiol

EXAMPLE 49

N-{2-[8-Allyl-7-(benzylthio)-1-naphthyl]ethyl}-N'-cyclobutylthiourea

Starting Compounds: Preparation 16 and Benzylthiol

EXAMPLE 50

N-[2-[8-Hexyl-7-(cyclohexylthio)-1-naphthyl]ethyl}-2-phenylacetamide

Starting Compounds: Preparation 15 and Cyclohexanethiol

EXAMPLE 51

N-Methyl-2-[7-(cyclopentylthio)-1-naphthyl]acetamide

Starting Compounds: Preparation 17 and Cyclopentanethiol

EXAMPLE 52

N-Cyclobutyl-3-[7-(2-propynylthio)-1-naphthyl]propanamide

Starting Compounds: Preparation 18 and 2-propynyl-1-thiol

EXAMPLE 53

N-Propyl-4-[7-(benzylthio)-1-naphthyl]butanamide

Starting Compounds: Preparation 19 and Benzylthiol

EXAMPLE 54

N-Cyclopropylmethyl-2-[7-(1H-5-imidazolylthio)-1-naphthyl]acetamide

Starting Compounds: Preparation 20 and 1H-5-imidazolylthiol

EXAMPLE 55

N-Cyclohexyl-4-[7-(phenylthio)-1-naphthyl]butanamide

Starting Compounds: Preparation 21 and Benzenethiol

EXAMPLE 56

N-Allyl-3-[7-(neopentylthio)-1-naphthyl]propanamide

Starting Compounds: Preparation 22 and Neopentylthiol

EXAMPLE 57

N-Cyclobutyl-N'-{2-[7-(2-propynylthio)-1-naphthyl]ethyl}urea

Starting Compounds: Preparation 23 and 2-propynyl-1-thiol

EXAMPLE 58

N-Isopropyl-N'-{2-[7-((4-(trifluoromethyl)benzyl)thio)-1-naphthyl]ethyl}urea

Starting Compounds: Preparation 24 and 4-trifluoromethylbenzylthiol

EXAMPLE 59

N-{2-[7-(tert-Butylthio)-1-naphthyl]ethyl}-N-methyl-N'-propylurea

Starting Compounds: Preparation 25 and Tert-butylthiol

EXAMPLE 60

Methyl 2-{[8-(2-[((butylamino)carbothioyl)amino]ethyl)-2-naphthyl]thio}benzoate

Starting Compounds: Preparation 26 and Methyl 2-mercaptobenzoate

EXAMPLE 61

N-Di-(4-chlorophenyl)methyl-N'-{2-[7-(2-pyridylthio)-1-naphthyl]ethyl}urea

Starting Compounds: Preparation 27 and 2-pyridinethiol

EXAMPLE 62

N-{2-[7-(Cyclopentylthio)-1-naphthyl]ethyl}-N-methyl-N'-propylurea

Starting Compounds: Preparation 25 and Cyclopentanethiol

EXAMPLE 63

Methyl 4-{[8-(2-methoxy-1-{[(2-morpholinoacetyl)amino]methyl}-2-oxoethyl))-2-naphthyl]thio}butanoate Starting Compounds: Preparation 28 and Methyl 4-mercaptobutanoate

EXAMPLE 64

Methyl 3-[(cyclopropylcarbonyl)amino]-2-[7-(2-propynylthio)-1-naphthyl]propanoate Starting Compounds: Preparation 29 and 2-propynethiol

EXAMPLE 65

Methyl 2-[7-(phenylthio)-1-naphthyl]-3-[(2,2,2-trifluoroacetyl)amino]propanoate

Starting Compounds: Preparation 30 and Benzenethiol

EXAMPLE 66

Methyl 2-{[7-(cyclopropylmethyl)thio]-1-naphthyl}-3-[(2,2,2-trifluoroacetyl)amino]propanoate Starting Compounds: Preparation 30 and Cyclopropylmethylthiol

EXAMPLE 67

O-{2 [7-(2-Propynylthio)-1-naphthyl]methyl}-N-acetyl-hydroxylamine

Starting Compounds: Preparation 31 and 2-propynethiol

EXAMPLE 68

O-{[7-(Phenylthio)-1-naphthyl]methyl}-N-(2-butenoyl)hydroxylamine

Starting Compounds: Preparation 32 and Benzenethiol

EXAMPLE 69

O-{[7-(Cyclohexylmethylthio)-1-naphthyl]methyl}-N-acetylhydroxylamine

Starting Compounds Preparation 31 and Cyclohexylmethanethiol

EXAMPLE 70

N-{3-[7-(1-Propenylthio)-1-naphthyl]propyl}acetamide

Starting Compounds: Preparation 33 and 1-propenethiol

EXAMPLE 71

N-{3-[7-(Butylthio)-1-naphthyl]propyl}-1-cyclohexanecarboxamide

Starting Compounds: Preparation 34 and Butanethiol

EXAMPLE 72

N-{3-[7-(Benzylthio)-1-naphthyl]propyl}-N'-propylthiourea

Starting Compounds: Preparation 35 and Benzylthiol

EXAMPLE 73

N-{3-[7-([1-Isopropyl-2-propynyl]thio)-1-naphthyl]propyl}acetamide

Starting Compounds: Preparation 33 and 1-isopropyl-2-propynylthiol

EXAMPLE 74

N-{2-[2(Phenylthio)-1-naphthyl]ethyl}-2,2,2-trifluoroacetamide

Starting Compounds: Preparation 36 and Benzenethiol

EXAMPLE 75

N-{2-[2-(2-Pyridylthio)-1-naphthyl]ethyl}-2-butenamide

Starting Compounds: Preparation 37 and 2-pyridinethiol

EXAMPLE 76

N-{2-[2-(2-Cyclohexenylthio)-1-naphthyl]ethyl}-1-cyclohexane-carboxamide

Starting Compounds: Preparation 38 and 2-cyclohexenylthiol

EXAMPLE 77

N-{1-Methyl-2-[2-(propylthio)-1-naphthyl]ethyl}propanamide

Starting Compounds: Preparation 39 and Propanethiol

EXAMPLE 78

N-{2-[7-(Allylthio)-3-phenyl-1-naphthyl]ethyl}acetamide

Starting Compounds: Preparation 40 and 2-propenethiol

EXAMPLE 79

N-{2-[7-(Benzylthio)-3-phenyl-1-naphthyl]ethyl)acetamide

Starting Compounds: Preparation 40 and Benzylthiol

EXAMPLE 80

Methyl 2-{[8-(2-[acetylamino]ethyl)-6-benzoyl-2-naphthyl]thio}benzoate

Starting Compounds: Preparation 41 and Methyl 2-mercaptobenzoate

EXAMPLE 81

N-{2-[3-Benzoyl-7-(2-propynylthio)-1-naphthyl]ethyl}-N'-propylurea

Starting Compounds: Preparation 42 and 2-propynylthiol

EXAMPLE 82

N-{2-[3-(Cyclopropylcarbonyl)-7-(isopropylthio)-1-naphthyl]ethyl}-1-cyclobutanecarboxamide Starting Compounds: Preparation 43 and Isopropanethiol

EXAMPLE 83

N-{2-[7-(Cyclopentylthio)-3-(cyclopropylcarbonyl)-1-naphthyl]ethyl}-N'-propylurea Starting Compounds: Preparation 44 and Cyclopentanethiol

EXAMPLE 84

N-{2-[3,7-Di-(1-propenylthio)-1-naphthyl]ethyl}propanamide

Starting Compounds: Preparation 45 and 1-propenethiol

Note: The procedure is as in the preceding Examples, but twice the equivalents of the thiol are used.

EXAMPLE 85

Methyl 4-{[6-(acetyloxy)-8-(2-[(cyclopropylcarbonyl)amino]ethyl)-2-naphthyl]thio}butanoate Starting Compounds: Preparation 46 and Methyl 4-mercaptobutanoate

EXAMPLE 86

N-{2-[(3-Benzyl-7-[(2,5-dihydro-1H-4-imidazolylthio]ethyl)-1-naphthyl]ethyl}pentanamide Starting Compounds: Preparation 47 and 2,5-dihydro-1H-4-imidazolethiol

EXAMPLE 87

N-{2-[3-Benzyl-7-(benzylthio)-1-naphthyl]ethyl}-N'-cyclohexylurea

Starting Compounds: Preparation 48 and Benzylthiol

EXAMPLE 88

N-Cyclohexyl-N'-[2-[3-ethyl-7-(isobutylthio)-1-naphthyl]ethyl}urea

Starting Compounds: Preparation 49 and Isobutanethiol

EXAMPLE 89

N-{2 [3-(Cyclopropylmethyl)-7-(hexylthio)-1-naphthyl]ethyl}acetamide

Starting Compounds: Preparation 50 and Hexanethiol

EXAMPLE 90

N-{[5-(Phenylthio)benzofuran-3-yl]methyloxy}-N'-propylthiourea

Starting Compounds: Preparation 51 and Benzenethiol

EXAMPLE 91

N-{3-[5-([1-Methyl-2-propynyl]thio)benzo[b]furan-3-yl]propyl}acetamide

Starting Compounds: Preparation 52 and 1-methyl-2-propynethiol

EXAMPLE 92

N-[2-(2-Methyl-5-{[4-(trifluoromethyl)benzyl]thio}benzo[b]furan-3-yl)ethyl]heptanamide Starting Compounds: Preparation 53 and 4-trifluoromethyl-benzenethiol

EXAMPLE 93

N-Methyl-4-[5-(cyclohexylthio)benzo[b]furan-3-yl]butanamide

Starting Compounds: Preparation 54 and Cyclohexanethiol

EXAMPLE 94

N-{2-(4-Allyl-[5-[(3-phenyl-2-propenyl)thio]benzo[b]furan-3-yl]ethyl}benzamide

Starting Compounds: Preparation 55 and 3-phenyl-2-propanethiol

EXAMPLE 95

N-{2-[5-(2-Pyridylthio)benzo[b]furan-3-yl]ethyl)acetamide

Starting Compounds: Preparation 56 and 2-pyridinethiol

EXAMPLE 96

O-{[5-([1-(tert-Butyl)-2-propynyl]thio)benzothiophen-3-yl]methyl}-N-thiopropionylhydroxylamine Starting Compounds: Preparation 57 and 1-tert-butyl-2-propynethiol

EXAMPLE 97

N-{3-[5-(Benzylthio)benzo[b]thiophen-3-yl]propyl}-1-cyclopropanecarboxamide

Starting Compounds: Preparation 58 and Benzylthiol

EXAMPLE 98

N-{[2-Benzyl-5-(3-butenylthio)benzo[b]thiophen-3-yl]methyl}acetamide

Starting Compounds: Preparation 59 and 3-butenethiol

EXAMPLE 99

Methyl 2{[3-(acetylamino]methyl)thieno[3,2-b]pyridin-5-yl]thio]benzoate

Starting Compounds: Preparation 60 and Methyl 2-mercaptobenzoate

EXAMPLE 100

N-{2-[4-Allyl-5-(allylthio)benzo[b]thiophen-3-yl]ethyl}benzamide

Starting Compounds: Preparation 61 and 2-propene-]-thiol

EXAMPLE 101

N-{2-[5-({3-Phenyl-2-propenyl}thio)-1H-4-indolyl]ethyl}-1-cyclopropane-carboxamide Starting Compounds: Preparation 62 and 3-phenyl-2-propenethiol

EXAMPLE 102

N-Methyl-4-[5-(2-propynylthio)-1H-3-indolyl]butanamide

Starting Compounds: Preparation 63 and 2-propynethiol

EXAMPLE 103

N-{2-[5-(2-Pyridylthio)-1H-3-indolyl]ethyl]-2-morpholinoacetamide

Starting Compounds: Preparation 64 and 2-pyridinethiol

EXAMPLE 104

N-Benzyl-N'-{2-[5-(tert-butylthio)-1H-3-indolyl]ethyl}urea

Starting Compounds: Preparation 65 and Tert-butylthiol

EXAMPLE 105

N-[2-[5-([Cyclopentylmethyl]thio)-1H-3-indolyl]ethyl}benzamide

Starting Compounds: Preparation 66 and Cyclopentylmethanethiol

EXAMPLE 106

N-{2-[1-Methyl-2-phenyl-5-(propylthio)-1H-pyrrolo[2,3-b]pyridin-3-yl]ethyl}acetamide Starting Compounds: Preparation 67 and Propanethiol

EXAMPLE 107

N-{2-[2-(2-Methoxyphenyl)-1-methyl-5-(2-propynylthio)-1H-pyrrolo-[2,3-b]pyridin-3-yl]ethyl}acetamide Starting Compounds: Preparation 68 and 2-propynethiol

EXAMPLE 108

N-{2-[2-(4-Fluorobenzyl)-1-methyl-5-{[4-(trifluoromethyl)benzyl]thio}-1H-pyrrolo[2,3-b]pyridin-3-yl]ethyl}acetamide Starting Compounds: Preparation 69 and 4-trifluoromethyl-benzylthiol

EXAMPLE 109

N-[2-(2-Benzyl-1-methyl-5-[(3-phenyl-2-propenyl)thio]-1H-pyrrolo-[2,3-b]pyridin-3-yl)ethyl]acetamide Starting Compounds: Preparation 70 and 3-phenyl-2-propenethiol

EXAMPLE 110

N-{2-[5-(2-Pyridylthio)-1H-pyrrolo[2,3-b]pyridin-3-yl]ethyl}acetamide

Starting Compounds: Preparation 71 and 2-pyridinethiol

EXAMPLE 111

N-{2-[5-(1-Propenylthio)-1H-pyrrolo[2,3-b]pyridin-3-yl]ethyl}-2,2,2-trifluoroacetamide Starting Compounds: Preparation 72 and 1-propenethiol

EXAMPLE 112

N-{2-[5-([1-Cyclohexyl-2-propynyl]thio)-2-phenyl-1H-pyrrolo[2,3-b]-pyridin-3-yl]ethyl}acetamide Starting Compounds: Preparation 73 and 1-cyclohexyl-2-propynethiol

EXAMPLE 113

N-{2-[5-(2-Cyclohexenylthio)-2-phenyl-1H-pyrrolo[2,3-b]pyridin-3-yl]ethyl}acetamide Starting Compounds: Preparation 73 and 2-cyclohexenethiol

EXAMPLE 114

Methyl 2-{[3-(2-[(cyclobutylcarbonyl)amino]ethyl)-1H-pyrrolo[2,3-b]pyridin-5-yl]thio}benzoate Starting Compounds: Preparation 75 and Methyl 2-mercaptobenzoate

EXAMPLE 115

N-[2-[5-(Benzylthio)-1H-pyrrolo[2,3-b]pyridin-3-yl]ethyl)-N'-butylthiourea

Starting Compounds: Preparation 76 and Benzylthiol

EXAMPLE 116

N-{2-[5-(Allylthio)-2-benzylbenzo[b]furan-3-yl]ethyl}-1-cyclopropane-carboxamide Starting Compounds: Preparation 77 and 2-propenethiol

EXAMPLE 117

N-{2-[5-(tert-Butylthio)-2-benzylbenzo[b]furan-3-yl]ethyl}-1-cyclopropanecarboxamide Starting Compounds: Preparation 77 and Tert-butylthiol

EXAMPLE 118

N-[2-[6-(2-Cyclohexenylthio)-1H-benzo[d]imidazol-1-yl]ethyl}-1-cyclopropanecarboxamide Starting Compounds: Preparation 78 and 2-cyclohexenethiol

EXAMPLE 119

N-{2-[5-(3-Butynylthio)-2-benzylbenzo[b]furan-3-yl]ethyl)-1-cyclopropanecarboxamide Starting Compounds: Preparation 77 and 3-butynylthiol

EXAMPLE 120

N-{2-[5-(Propylthio)-2-phenylbenzo[b]thiophen-3-yl]ethyl}acetamide

Starting Compounds: Preparation 210 and Propylthiol

EXAMPLE 121

N-{[6-([1-Methyl-1H-2-imidazolyl]thio)-3,4-dihydro-2H-3-yl-chromenyl]methyl}acetamide Starting Compounds: Preparation 79 and 1-methyl-1H-2-imidazolylthiol

EXAMPLE 122

N-{[6-(Allylthio)-3,4-dihydro-2H-3-chromenyl]methyl}-1-cyclopropane-carboxamide

Starting Compounds: Preparation 80 and 2-propenethiol

EXAMPLE 123

N-{2-[5-(2-Cyclohexenylthio)benzo[b]thiophen-3-yl]ethyl}acetamide

Starting Compounds: Preparation 211 and 2-cyclohexenethiol

EXAMPLE 124

N-{[6-(Benzylthio)-3,4-dihydro-2H-4-chromenyl]methyl}acetamide

Starting Compounds: Preparation 82 and Benzylthiol

EXAMPLE 125

Methyl 2-{[4-([butyrylamino]methyl)-3,4-dihydro-2H-6-chromenyl]thio}benzoate

Starting Compounds: Preparation 83 and Methyl 2-mercaptobenzoate

EXAMPLE 126

N-{2-[6-([(4-Trifluoromethyl)benzyl]thio)-3,4-dihydro-2H-4-chromenyl]ethyl}-3-butanamide Starting Compounds: Preparation 84 and 4-trifluoromethylbenzylthiol

EXAMPLE 127

N-[2-[6-(2-Propynylthio)-3,4-dihydro-2H-4-chromenyl]ethyl}acetamide

Starting Compounds: Preparation 85 and 2-propynethiol

EXAMPLE 128

N-{2-[6-([Cyclopropylmethyl]thio)-3,4-dihydro-2H-4-chromenyl]ethyl}-2-phenylacetamide Starting Compounds: Preparation 86 and Cyclopropylmethanethiol

EXAMPLE 129

N-{[6-(Cyclobutylthio)-2H-3-chromenyl]methyl}acetamide

Starting Compounds: Preparation 87 and 2-cyclobutanethiol

EXAMPLE 130

N-{[6-(Allylthio)-2H-3-chromenyl]methyl}butanamide

Starting Compounds: Preparation 88 and 2-propenethiol

EXAMPLE 131

N-Methyl-3-{6-[(1-isopropyl-2-propynyl)thio]-2H-3-chromenyl}propanamide

Starting Compounds: Preparation 89 and 1-isopropyl-2-propynethiol

EXAMPLE 132

N-{[6-(Benzylthio)-2-phenyl-2H-3-chromenyl]methyl}acetamide

Starting Compounds: Preparation 90 and Benzylthiol

EXAMPLE 133

N-{[2-Phenyl-6-(2-pyridylthio)-2H-3-chromenyl]methyl}butanamide

Starting Compounds: Preparation 91 and 2-pyridinethiol

EXAMPLE 134

Methyl 2-{[4-(2-(acetylamino)ethyl)-3,4-dihydro-2H-6-thiochromenyl]thio}benzoate Starting Compounds: Preparation 92 and Methyl 2-mercaptobenzoate

EXAMPLE 135

N-{[3-Phenyl-7-[(3-phenyl-2-propenyl)thio]-1,4-benzodioxin-2-yl]methyl}acetamide Starting Compounds: Preparation 93 and 3-phenyl-2-propenethiol

EXAMPLE 136

N-{[3-Benzyl-7-(2-propenylthio)-1,4-benzodioxin-2-yl]methyl}acetamide

Starting Compounds: Preparation 94 and 2-propenethiol

EXAMPLE 137

N-{[7-(2-Cyclohexenylthio)-1,4-benzodioxin-2-yl]methyl}-1-cyclopropanecarboxamide Starting Compounds: Preparation 95 and 2-cyclohexenethiol

EXAMPLE 138

N-{2-[5-(Isopentylthio)benzo[b]thiophen-3-yl]ethyl}acrylamide

Starting Compounds: Preparation 212 and Isopentanethiol

EXAMPLE 139

N-{2-[7-(2-Propynylthio)-2,3-dihydro-1,4-benzodioxin-2-yl]ethyl}acetamide

Starting Compounds: Preparation 97 and 2-propynethiol

EXAMPLE 140

Methyl 4-{[3-(2-anilino-2-oxoethyl)-2,3-dihydro-1,4-benzodioxin-6-yl]thio}butanoate Starting Compounds: Preparation 98 and Methyl 4-mercaptobutanoate

EXAMPLE 141

N-{2-[7-(2-Pyridylthio)-2,3-dihydro-1,4-benzodioxin-2-yl]ethyl}acetamide

Starting Compounds: Preparation 97 and 2-pyridinethiol

EXAMPLE 142

N-{[6-(Cyclopentylthio)-2,3-dihydro-1,4-benzodioxin-5-yl]methyl}acetamide

Starting Compounds: Preparation 99 and Cyclopentanethiol

EXAMPLE 143

N-{3-[7-(1-Propenylthio)-1,2,3,4-tetrahydro-1-naphthyl]propyl}acetamide

Starting Compounds: Preparation 100 and 1-propenethiol

EXAMPLE 144

N-[8-(Ethylthio)-5-methyl-1,2,3,4-tetrahydro-2-naphthyl]acetamide

Starting Compounds: Preparation 220 and Ethanethiol

EXAMPLE 145

N-{2-[5-(Cyclobutylthio)-benzo[d]isoxazol-3-yl]ethyl}-1-cyclopropane-carboxamide Starting Compounds: Preparation 101 and Cyclobutanethiol

EXAMPLE 146

N-{2-[7-((4-Methylphenyl)thio)-1,2,3,4-tetrahydro-1-naphthyl]ethyl}acetamide

Starting Compounds: Preparation 219 and 4-methyl-benzenethiol

EXAMPLE 147

N-[9-(Allylthio)-2,3,6,10b-tetrahydro-1H-benzo[f]chromen-2-yl]acetamide

Starting Compounds: Preparation 102 and 2-propenethiol

EXAMPLE 148

N-[9-(Isobutylthio)-2,3,6,10b-tetrahydro-1H-benzo[f]chromen-2-yl]-2-cyclopropylacetamide Starting Compounds: Preparation 103 and Isobutanethiol

EXAMPLE 149

N-[9-(Phenylthio)-2,3,6,10b-tetrahydro-1H-benzo[f]chromen-1-yl]butanamide

Starting Compounds: Preparation 104 and Benzenethiol

EXAMPLE 150

N-{[9-(Benzylthio)-2,3,6,10b-tetrahydro-1H-benzo[f]chromen-1-yl]methyl}acetamide Starting Compounds: Preparation 105 and Benzylthiol

EXAMPLE 151

Methyl 2-{[2-([methylamino]carbonyl)-6,10b-dihydro-3H-benzo[f]chromen-9-yl]thio}benzoate Starting Compounds: Preparation 106 and Methyl 2-mercaptobenzoate

EXAMPLE 152

N-[4-(Butylthio)-2,3-dihydro-1H-2-phenalenyl]propanamide

Starting Compounds: Preparation 107 and Butanethiol

EXAMPLE 153

N-[4-[(1-Methyl-1H-2-imidazolyl)thio]-2,3-dihydro-1H-2-phenalenyl}-2-methylpropanamide Starting Compounds: Preparation 108 and 1-methyl-1H-2-imidazolethiol

EXAMPLE 154

N-Cyclopropyl-N'-[4-(phenylthio)-2,3-dihydro-1H-2-phenalenyl]thiourea

Starting Compounds: Preparation 109 and Benzenethiol

EXAMPLE 155

N-Cyclohexyl-N'-{4-[(4-[trifluoromethyl]phenyl)thio]-2,3-dihydro-1H-2-phenalenyl}urea Starting Compounds: Preparation 110 and 4-trifluoromethylbenzenethiol

EXAMPLE 156

N-[4,9-Di(tert-butylthio)-2,3-dihydro-1H-2-phenalenyl]acetamide

Starting Compounds: Preparation 111 and Tert-butylthiol

EXAMPLE 157

N-{[4-(Benzylthio)-2,3-dihydro-1H-1-phenalenyl]methyl}acetamide

Starting Compounds: Preparation 112 and Benzylthiol

EXAMPLE 158

Methyl 2-{[1-(2-[(cyclopropylcarbonyl)amino]ethyl)-2,3-dihydro-1H-4-phenalenyl]thio}benzoate Starting Compounds: Preparation 113 and Methyl 2-mercaptobenzoate

EXAMPLE 159

N-Methyl-N'-{[4,9-di-([3-phenyl-2-propenyl]thio)-2,3-dihydro-1H-1-phenalenyl]methyl}urea Starting Compounds: Preparation 114 and 3-phenyl-2-propenethiol Note: The procedure is as in Example 84.

EXAMPLE 160

N-[6-(Cyclopropylthio)-1,3,4,5-tetrahydrobenzo[cd]indol-4-yl acetamide

Starting Compounds: Preparation 115 and Cyclopropanethiol

EXAMPLE 161

N-[6-(2-Cyclohexenylthio)-4,5-dihydro-3H-benzo[cd]isobenzofuran-4-yl]-acetamide

Starting Compounds: Preparation 116 and 2-cyclohexenethiol

EXAMPLE 162

N-[6-(Benzylthio)-4,5-dihydro-3H-naphtho[1,8-bc]thiophen-4-yl]acetamide

Starting Compounds: Preparation 117 and Benzylthiol

EXAMPLE 163

N-Cyclobutyl-6-(2-pyridylthio)-4,5-dihydro-3H-benzo[cd]isobenzofuran-4-carboxamide Starting Compounds: Preparation 118 and 2-pyridinethiol

EXAMPLE 164

N-{[2-(2-Furylmethyl)-5-(2-propynylthio)benzo[b]furan-3-yl]methyl}acetamide

Starting Compounds: Preparation 119 and 2-propynethiol

EXAMPLE 165

N-{[5-([Cyclobutylmethyl]thio)-2(3-pyridylmethyl)benzo-[b]furan-3-yl]methyl}benzamide Starting Compounds: Preparation 120 and Cyclobutylmethanethiol

EXAMPLE 166

N-{[5-(2-Cyclohexenylthio)-2-(3-phenyl-2-propenyl)benzo[b]thiophen-3-yl]methyl}-1-cyclobutanecarboxamide Starting Compounds: Preparation 121 and 2-cyclohexenethiol

EXAMPLE 167

N-{2-[7-(2-Butenylthio)-3-(2-naphthyl)-1-naphthyl]ethyl}heptanamide

Starting Compounds: Preparation 122 and 2-butenethiol

EXAMPLE 168

4-[2-(Benzoylamino)ethyl]-6-(tert-butylthio)-2-naphthyl trifluoromethanesulphonate Starting Compounds: Preparation 123 and Tert-butanethiol

EXAMPLE 169

N-{2-[3-(3-Phenyl-2-propenyl)-7-(2-pyridylthio-1-naphthyl]ethyl}-2-cyclohexylacetamide Starting Compounds: Preparation 124 and 2-pyridinethiol

EXAMPLE 170

N-{[7-([4-Isopropylphenyl]thio)-3-(2-thienyl)-1-naphthyl]methyl}butanamide

Starting Compounds: Preparation 125 and 4-isopropylphenylthiol

EXAMPLE 171

N-{2-[7-([Cyclopropylmethyl]sulphinyl)-1-naphthyl]ethyl}-4-chlorobutanamide

The product obtained in Example 43 (10 mmol) is added to an aqueous 0.5M sodium periodate solution (21 ml, 10.5 mmol) at 0° C. Stirring at 0–5° C. is carried out overnight. The solution is filtered and the filtrate is extracted with chloroform. The organic phase is dried over magnesium sulphate and is concentrated under reduced pressure. The residue is chromatographed on silica gel to yield the title compound.

In Examples 172 to 184 the procedure is the same as in Example 171, starting from the appropriate thioether.

EXAMPLE 172

N-{2-[7-(Cyclohexylsulphinyl)-8-hexyl-1-naphthyl]ethyl}-2-phenylacetamide

Starting Compound: Example 50

EXAMPLE 173

N-Cyclopropylmethyl-2-[7-(1H-5-imidazolylsulphinyl)-1-naphthyl]acetamide

Starting Compound: Example 54

EXAMPLE 174

N-{1-Methyl-2-[2-(propylsulphinyl)-1-naphthyl]ethyl}propanamide

Starting Compound: Example 77

EXAMPLE 175

N-{2-[3-(Cyclopropylcarbonyl)-7-(isopropylsulphinyl)-1-naphthyl]ethyl}-1-cyclobutanecarboxamide Starting Compound: Example 82

EXAMPLE 176

N-{2-[2-Methyl-5-([4-(trifluoromethyl)benzyl]sulphinyl)benzo[b]furan-3-yl]ethyl}heptamide Starting Compound: Example 92

EXAMPLE 177

N-{3-[5-(Benzylsulphinyl)benzo[b]thiophen-3-yl]propyl}-1-cyclopropane-carboxamide Starting Compound: Example 97

EXAMPLE 178

N-{2-[5-([Cyclopentylmethyl]sulphinyl)-1H-3-indolyl]ethyl}benzamide

Starting Compound: Example 105

EXAMPLE 179

N-{2-[5-(2-Pyridylsulphinyl)-1H-pyrrolo[2,3-b]pyridin-3-yl]ethyl}acetamide

Starting Compound: Example 110

EXAMPLE 180

N-{2-[2-Benzyl-5-(tert-butylsulphinyl)benzo[b]furan-3-yl]ethyl}-1-cyclopropanecarboxamide Starting Compound: Example 117

EXAMPLE 181

N-{[6-(Benzylsulphinyl)-3,4-dihydro-2H-4-chromenyl]methyl}acetamide

Starting Compound: Example 124

EXAMPLE 182

N-{2-[5-(Cyclobutylsulphinyl)benzo[d]isoxazol-3-yl]ethyl}-1-cyclopropanecarboxamide Starting Compound: Example 145

EXAMPLE 183

N-[4,9-Di-(tert-butylsulphinyl)-2,3-dihydro-1H-2-phenalenyl]acetamide

Starting Compound: Example 156

EXAMPLE 184

N-{[5-(Cyclobutylmethyl)sulphinyl-2-(2-furylmethyl)benzo[b]furan-3-yl]-methyl}benzamide Starting Compound: Example 165

EXAMPLE 185

N-{2-[7-(Benzylsulphonyl)-1-naphthyl]ethyl}heptanamide

The product obtained in Example 39 (10 mmol) is dissolved in 40 ml of methanol and is cooled to 0° C. with the aid of an ice bath. A 49.5% solution of $KHSO_5$ (30 mmol) in water (40 ml) is added. Stirring is carried out for 4 hours at ambient temperature. The reaction mixture is then diluted with water and extracted 3 times with chloroform. The organic phases are combined, washed with water and with saturated NaCl solution and then dried over $Na_2SO_4$ and concentrated under reduced pressure. The title product is obtained after chromatography on silica gel.

Examples 186 to 193 are obtained by proceeding as in Example 185, starting from the corresponding thioether.

EXAMPLE 186

N-Cyclohexyl-4-[7-(phenylsulphonyl)-1-naphthyl]butanamide

Starting Compound: Example 55

EXAMPLE 187

N-{1-Methyl-2-[2-(propylsulphonyl)-1-naphthyl]ethyl}propanamide

Starting Compound: Example 77

EXAMPLE 188

N-Methyl-4-[5-(cyclohexylsulphonyl)benzo[b]furan-3-yl]butanamide

Starting Compound: Example 93

EXAMPLE 189

N-{2-[1-Methyl-2-phenyl-5-(propylsulphonyl)-1H-pyrrolo[2,3-b]pyridin-3-yl]ethyl}acetamide Starting Compound: Example 106

EXAMPLE 190

N-{2-[6-([Cyclopropylmethyl]sulphonyl)-3,4-dihydro-2H-4-chromenyl]ethyl}-2-phenylacetamide Starting Compound: Example 128

EXAMPLE 191

N-{[6-(Cyclopentylsulphonyl)-2,3-dihydro-1,4-benzodioxin-5-yl]methyl}acetamide

Starting Compound: Example 142

EXAMPLE 192

N-[4-(Butylsulphonyl)-2,3-dihydro-1H-2-phenalenyl]propanamide

Starting Compound: Example 152

EXAMPLE 193

N-Cyclobutyl-6-(2-pyridylsulphonyl)-4,5-dihydro-3H-benzo[cd]isobenzofuran-4-carboxamide Starting Compound: Example 163

EXAMPLE 194

8-[2-(Benzoylamino)ethyl]-2-naphthyl propanethioate

Polyphosphate ester (20 ml) is added to a mixture of propanoic acid (30 mmol) and the product obtained in Example 10 (31 mmol) and the reaction mixture is stirred for 15 hours at ambient temperature. The mixture is then treated with saturated aqueous sodium hydrogen carbonate solution (200 ml) and is extracted with chloroform (3×30 ml). The organic phases are combined, dried over magnesium sulphate and then concentrated under reduced pressure. The residue is chromatographed on silica gel to yield the title product.

(Polyphosphate ester is prepared according to the method described by W. Pollmann et al., Biochem. Biophys. Acta, 80 (1), 1964).

Examples 195 to 204 are prepared according to the procedure of Example 194, starting from appropriate reactants.

EXAMPLE 195

1-Allyl-8-{2-[([cyclobutylamino]carbothioyl)amino]ethyl}-2-naphthyl benzenecarbothioate Starting Compound: Example 12

EXAMPLE 196

3-[2-(Acetylamino)ethyl]-2-phenyl-1H-pyrrolo[2,3-b]pyridin-5-yl cyclopentanecarbothioate Starting Compound: Example 23

EXAMPLE 197

1-{2-[(2,2,2-Trifluoroacetyl)amino]ethyl}-2-naphthyl 2-pentenethioate

Starting Compound: Example 17

EXAMPLE 198

6-Benzoyl-8-{2-[([propylamino]carbonyl)amino]ethyl}-2-naphthyl 4-(trifluoromethyl)-1-benzenecarbothioate Starting Compound: Example 18

EXAMPLE 199

4-Allyl-3-[2-(benzoylamino)ethyl]benzo[b]thiophen-5-yl 2-cyclobutylethanethioate Starting Compound: Example 21

EXAMPLE 200

2-Benzyl-3-{2-[(cyclopropylcarbonyl)amino]ethyl}benzo[b]furan-5-yl 2-(2-oxotetrahydro-1H-1-pyrrolyl)ethanethioate Starting Compound: Example 24

EXAMPLE 201

3-[3-(Methylamino)-3-oxopropyl]-2H-6-chromenyl 2-morpholino-ethanethioate

Starting Compound: Example 26

EXAMPLE 202

3-[(Acetylamino)methyl]-2-benzyl-1,4-benzodioxin-6-yl 2-furan-carbothioate

Starting Compound: Example 28

EXAMPLE 203

1-{2-[(Cyclopropylcarbonyl)amino]ethyl}-2,3-dihydro-1H-4-phenalenyl ethanethioate Starting Compound: Example 33

EXAMPLE 204

8-[(Butanoylamino)methyl]-6-(2-thienyl)-2-naphthyl 2-butenethioate

Starting Compound: Example 36

EXAMPLE 205

8-[(Heptanoylamino)methyl]-2-naphthyl(propylamino)methanethioate

Propyl isocyanate (11 mmol) and the product obtained in Example 11 (10 mmol) are dissolved in dimethylformamide (20 ml). The reaction mixture is stirred at ambient temperature for 16 hours under nitrogen. After evaporating off the dimethylformamide, the residue is chromatographed on silica gel to yield the title product.

In Examples 206 to 209 the procedure is as in Example 205, starting from appropriate reactants.

EXAMPLE 206

3-[2-(Acetylamino)ethyl]-2-phenyl-1H-pyrrolo[2,3-b]pyridin-5-yl (cyclohexylamino)methanethioate Starting Compound: Example 23

EXAMPLE 207

1-{2-[(Cyclopropylcarbonyl)amino]ethyl}-2,3-dihydro-1H-4-phenalenyl (propylamino)methanethioate Starting Compound: Example 33

EXAMPLE 208

3-{[(Cyclobutylcarbonyl)amino]methyl}-2-(3-phenyl-2-propenyl)benzo-[b]thiophen-5-yl anilinomethanethioate Starting Compound: Example 35

EXAMPLE 209

8-[(Butanoylamino)methyl]-6-(2-thienyl)-2-naphthyl (benzylamino)methanethioate

Starting Compound: Example 36

EXAMPLE 210

Ethyl 9-[4-(cyclohexylamino)-4-oxobutyl]-1-methylnaphtho-[2,1-b]thiophene-2-carboxylate Step A: Ethyl 2-{[8-[4-(cyclohexylamino)-4-oxobutyl]-2-naphthyl]sulphanyl}-3-oxo-butanoate Sodium (34 mmol) is added, with vigorous stirring, over a period of one hour, to a boiling solution of the product obtained in Example 13 (34 mmol) in 70 ml of anhydrous xylene. Stirring is continued, under reflux, for 2 hours and the mixture is allowed to cool to approximately 80° C. Ethyl chloro-2-acetylacetate (38 mmol) is then added dropwise. The mixture is then heated at reflux again for one hour. After cooling, the organic phase is washed with water, dried and concentrated to dryness under reduced pressure to yield the title product.

Step B: Ethyl 9-[4-(cyclohexylamino)-4-oxobutyl]-1-methylnaphtho[2,1-b]thiophene-2-carboxylate The product obtained in Step A (18 mmol) is added all at once to 5 ml of sulphuric acid (d=1.81). The temperature of the reaction mixture rises rapidly to approximately 80° C. After stirring for 5 minutes, the mixture is poured into 100 ml of ice-cold water and is then extracted with dichloromethane. The organic phase is then washed with water, then with saturated sodium hydrogen carbonate solution and then again with water. The organic phase is then dried over magnesium sulphate and is then concentrated under reduced pressure. The residue is chromatographed to yield the title product.

In Examples 211 to 215 the procedure is as in Example 210, starting from appropriate reactants.

EXAMPLE 211

Ethyl 9-{2-[({[di(4-chlorophenyl)methyl]amino}carbonyl)amino]ethyl}-1-ethylnaphtho[2,1-b]thiophene-2-carboxylate Starting Compound: Example 15

EXAMPLE 212

Ethyl 10-{3-[(cyclohexylcarbonyl)amino]propyl}-1-methyl-3H-benzo[f]thiochromene-3-carboxylate Starting Compound: Example 16

EXAMPLE 213

Isopropyl 9-[(acetylamino)methyl]-1-methyl-8,9-dihydro-7H-thieno-[3,2-f]chromene-2-carboxylate Starting Compound: Example 25

EXAMPLE 214

Ethyl 10-[2-(acetylamino)ethyl]-1-methyl-3,8,9,10-tetrahydrothiopyrano-[3,2-f]thiochromene-3-carboxylate Starting Compound: Example 27

EXAMPLE 215

Methyl 8-{[(cyclobutylcarbonyl)amino]methyl}-1-isopropyl-7-(3-phenyl-2-propenyl)thieno[3',2':3,4]benzo[b]thiophene-2-carboxylate Starting Compound: Example 35

EXAMPLE 216

Ethyl 9-{2-[({[di-(4-chlorophenyl)methyl]amino}carbonyl)amino]ethyl}-1-ethyl-3-oxo-3H-3$\lambda^4$-naphtho[2,1-b]thiophene-2-carboxylate The procedure is as in Example 171, starting from Example 211.

EXAMPLE 217

Ethyl 10-{3-[(cyclohexylcarbonyl)amino]propyl}-1-methyl-4,4-dioxo-3,4-dihydro-4$\lambda^6$-benzo[f]thiochromene-3-carboxylate The procedure is as in Example 185, starting from Example 212.

EXAMPLE 218

N-[2-(1-Oxo-2,3-dihydro-1H-benzo[f]thiochromen-10-yl)ethyl]-3-(trifluoromethyl)benzamide Step A: Ethyl 3-{[8-(2-{[3-(trifluoromethyl)benzoyl]amino}ethyl)-2-naphthyl]sulphanyl}propanoate The procedure is as in Example 8, but the ethanethiol is replaced by ethyl 3-mercaptopropanoate and the product of Preparation 6 is used.

Step B: 3-{[8-(2-{[3-(Trifluoromethyl)benzoyl]amino}ethyl)-2-naphthyl]sulphonyl}propanoic acid A 0.5N aqueous solution of $K_2CO_3$ (10 ml) is added to the product obtained in Step A (4 mmol) dissolved in methanol (10 ml).

When the reaction has ceased, the solution is acidified to pH 6 using 1N HCl solution. The reaction mixture is extracted with dichloromethane. The organic phase is washed with water, dried over magnesium sulphate, concentrated under reduced pressure and chromatographed on silica gel to yield the title product.

Step C: 3-{[8-(2-{[3-(Trifluoromethyl)benzoyl]amino}ethyl)-2-naphthyl]sulphonyl-propanoyl chloride The product obtained in Step B (3 mmol), dissolved in thionyl chloride, is stirred at 60° C. under a current of nitrogen for one hour. The thionyl chloride is evaporated off under reduced pressure and the residue is dried with the aid of a vane pump to yield the title product.

Step D: N-[2-(1-Oxo-2,3-dihydro-1H-benzo[f]thiochromen-10-yl)ethyl]-3-(trifluoromethyl)benzamide The product obtained in Step C (3 mmol), dissolved in 1,1,2,2-tetrachloroethane (30 ml), is poured dropwise into a solution of aluminium chloride (10 mmol) in the same solvent (20 ml) under nitrogen. The reaction mixture is heated at 60° C., with stirring, until the reaction has ceased. The solution is then poured into a mixture of ice (10 g) and concentrated HCl (0.3 ml) and stirring is carried out for one hour. The aqueous phase is extracted with chloroform (twice); the combined organic phases are then dried over magnesium sulphate, concentrated under reduced pressure and then chromatographed on silica gel to yield the title product.

In Examples 219 to 228, the procedure is as in Example 218, but the appropriate thiol and Preparation are used to obtain the title compound.

EXAMPLE 219

N-Cyclopropylmethyl-2-(1-oxo-2,3-dihydro-1H-benzo[f]thiochromen-10-yl)acetamide

Starting Compound: Preparation 20

EXAMPLE 220

N-[2-(2,2-Dimethyl-1-oxo-1,2-dihydronaphtho[2,1-b]thiophen-9-yl)ethyl]-N-methyl-N'-propylurea Starting Compound: Preparation 25

EXAMPLE 221

N-[3-(1-Oxo-2,3,7,8,9,10-hexahydro-1H-benzo[f]thiochromen-10-yl)-propyl]acetamide Starting Compound: Preparation 100

EXAMPLE 222

N-[2-(8-Benzyl-1-oxo-1,2-dihydro-1H-benzo[f]thiochromen-10-yl)ethyl]-1-cyclohexanecarboxamide Starting Compound: Preparation 48

EXAMPLE 223

N-Methyl-4-(7,7-dimethyl-8-oxo-7,8-dihydrothieno[3',2':3,4]benzo[f]furan-1-yl)butanamide Starting Compound: Preparation 54

EXAMPLE 224

N-[(2-Benzyl-9-oxo-8,9-dihydro-7H-thieno[3,2-f]
thiochromen-1-yl)-methyl]acetamide Starting Compound: Preparation 59

EXAMPLE 225

N-[2-(7,7-Dimethyl-9-oxo-3,7,8,9-tetrahydrothiopy-
rano[3,2-e]indol-1-yl)-ethyl]benzamide Starting Compound: Preparation 66

EXAMPLE 226

N-[(1-Oxo-1,7,8,9-tetrahydro-2H-thieno[3,2-f]
chromen-9-yl)methyl]acetamide

Starting Compound: Preparation 82

EXAMPLE 227

N-{[1-Oxo-8-(3-phenyl-2-propenyl)-2,3-dihydro-
1H-benzo[f]thiochromen-10-yl]methyl}-2-cyclo-
hexylacetamide Starting Compound: Preparation 124

EXAMPLE 228

N-[(3-Benzyl-9-oxo-8,9-dihydrothieno[2',3':5,6]
benzo[b][1,4]dioxin-2-yl)-methyl]acetamide Starting Compound: Preparation 94

EXAMPLE 229

N-[2-(2,3-Dihydro-1H-benzo v]thiochromen-9-yl)
ethyl]-3-(trifluoromethyl)benzamide The compound of Example 218 (3 mmol) is dissolved in acetic acid (70 ml) and, after several purges with argon, 10% palladium-on-carbon (600 mg) is added and the mixture is placed under a hydrogen atmosphere. Stirring is carried out at ambient temperature until the reaction is complete and the palladium is filtered off over Celite. The acetic acid is evaporated off to dryness and the residue is chromatographed on silica gel to yield the title product.

In Examples 230 to 235, the procedure is as for Example 229, but the product of Example 218 is replaced by the appropriate reactant.

EXAMPLE 230

N-Cyclopropylmethyl-2-(2,3-dihydro-1H-benzo[f]
thiochromen-10-yl)-acetamide

Starting Compound: Example 219

EXAMPLE 231

N-[2-(2,2-Dimethyl-1,2-dihydronaphtho[2,1-b]
thiophen-9-yl)ethyl]-N-methyl-N'-propylurea Starting Compound: Example 220

EXAMPLE 232

N-[(2-Benzyl-8,9-dihydro-7H-thieno[3,2-f]thio-
chromen-1-yl)methyl]acetamide

Starting Compound: Example 224

EXAMPLE 233

N-[2-(7,7-Dimethyl-3,7,8,9-tetrahydrothiopyrano[3,
2-e]indol-1-yl)ethyl]benzamide Starting Compound: Example 225

EXAMPLE 234

N-(1,7,8,9-Tetrahydro-2H-thieno[3,2-]]chromen-9-
yl-methyl]acetamide

Starting Compound: Example 226

EXAMPLE 235

N-[(3-Benzyl-8,9-dihydrothieno[2',3':5,6]benzo[b]
[1,4]dioxin-2-yl)-methyl]acetamide Starting Compound: Example 228

In Examples 236 to 239 the procedure is as in Example 171, starting from appropriate reactants.

EXAMPLE 236

N-[2-(1,4-Dioxo-1,2,3,4-tetrahydro-4$\lambda^4$-benzo[f]
thiochromen-10-yl)ethyl]-3-(trifluoromethyl)benza-
mide Starting Compound: Example 218

EXAMPLE 237

N-Cyclopropylmethyl-2-(4-oxo-1,2,3,4-tetrahydro-
4$\lambda^4$-benzo[f]thiochromen-10-yl)acetamide Starting Compound: Example 230

EXAMPLE 238

N-[2-(2,2-Dimethyl-3-oxo-2,3-dihydro-1H-3$\lambda^4$-
naphtho[2,1-b]thiophen-9-yl)ethyl]-N-methyl-N'-
propylurea Starting Compound: Example 231

EXAMPLE 239

N-[2-(7,7-Dimethyl-6-oxo-6,7,8,9-tetrahydro-3H-
6$\lambda^4$-thiopyrano[3,2-e]indol-1-yl)ethyl]benzamide Starting Compound: Example 233

In Examples 240 to 243 the procedure is as in Example 185, starting from appropriate substrates.

EXAMPLE 240

N-Methyl-4-(7,7-dimethyl-6,6,8-trioxo-7,8-dihydro-6H-6λ$^6$-thieno-[3',2':3,4]benzo[f]furan-1-yl)butanamide Starting Compound: Example 223

EXAMPLE 241

N-Cyclopropylmethyl-2-(4,4-dioxo-1,2,3,4-tetrahydro-4λ$^6$-benzo[f]thiochromen-10-yl)acetamide Starting Compound: Example 230

EXAMPLE 242

N-[(3,3-Dioxo-1,2,3,7,8,9-hexahydro-3λ$^6$-thieno[3,2-f]chromen-9-yl)methyl]acetamide Starting Compound: Example 234

EXAMPLE 243

N-[(3-Benzyl-7,7-dioxo-8,9-dihydro-7H-7λ$^6$-thieno[2',3':5,6]benzo[b][1,4]dioxin-2-yl)methyl]acetamide Starting Compound: Example 235

EXAMPLE 244

N-[2-(3H-Benzo[f]thiochromen-10-yl)ethyl]-2-bromoacetamide

The product of Example 40 (10 mmol) and triethylene glycol are introduced into a two-necked flask. Heating is carried out at 160–170° C., under nitrogen and with stirring, for five hours. The reaction mixture is poured into ice-cold water and is extracted with ethyl acetate. The organic phase is washed with water and dried over calcium chloride. After filtration, the organic phase is concentrated under reduced pressure. The residue is chromatographed on silica gel to yield the title product.

In Examples 245 to 260, the same method as in Example 244 is applied, but the product of Example 40 is replaced by the appropriate substrate.

EXAMPLE 245

N-Cyclobutyl-3-(3H-benzo[f]thiochromen-10-yl)propanamide

Starting Compound: Example 52

EXAMPLE 246

N-[2-(3H-Benzo[f]thiochromen-10-yl)ethyl]-N'-cyclobutylurea

Starting Compound: Example 57

EXAMPLE 247

Methyl 2-(3H-benzo[f]thiochromen-10-yl)-3-[(cyclopropylcarbonyl)amino]propanoate Starting Compound: Example 64

EXAMPLE 248

O-[(3H-Benzo[f]thiochromen-10-yl)methyl]-N-acetylhydroxylamine

Starting Compound: Example 67

EXAMPLE 249

N-[2-(3-Isopropyl-3H-benzo[f]thiochromen-10-yl)ethyl]acetamide

Starting Compound: Example 73

EXAMPLE 250

N-[2-(8-Benzoyl-3H-benzo[f]thiochromen-10-yl)ethyl]-N'-propylurea

Starting Compound: Example 81

EXAMPLE 251

N-[3-(7-Methyl-7H-thiochromeno[6,5-b]furan-1-yl)propyl]acetamide

Starting Compound: Example 91

EXAMPLE 252

O-{[(7-tert-Butyl-7H-thiochromeno[6,5-b]thiophen-1-yl)methyl]-N-thiopropionyl-hydroxylamine Starting Compound: Example 96

EXAMPLE 253

N-Methyl-4-(3,7-dihydrothiopyrano[3,2-e]indol-1-yl)butanamide

Starting Compound: Example 102

EXAMPLE 254

N-{2-[2-(2-Methoxyphenyl)-3-methyl-3,7-dihydropyrrolo[2,3-b]thiopyrano[3,2-d]pyridin-1-yl]ethyl}]acetamide Starting Compound: Example 107

EXAMPLE 255

N-[2-(7-Cyclohexyl-2-phenyl-3,7-dihydropyrrolo[2,3-b]thiopyrano-[3,2-d]pyridin-1-yl}]acetamide Starting Compound: Example 112

EXAMPLE 256

N-[2-(2-Benzyl-7,8-dihydrothiepino[3',2':3,4]benzo[b]furan-1-yl)ethyl]-1-cyclopropanecarboxamide Starting Compound: Example 119

EXAMPLE 257

N-[2-(1,2,3,8-Tetrahydrothiopyrano[3,2-f]chromen-1-yl)ethyl]acetamide

Starting Compound: Example 127

EXAMPLE 258

N-Methyl-3-(8-isopropyl-3,8-dihydrothiopyrano[3,2-f]chromen-1-yl)propanamide

Starting Compound: Example 131

EXAMPLE 259

N-[2-(2,3-Dihydro-8H-thiochromeno[5,6-b][1,4]dioxin-2-yl)ethyl]acetamide

Starting Compound: Example 139

EXAMPLE 260

N-{[2-(2-Furylmethyl)-7H-thiochromeno[6,5-b]furan-1-yl]methyl}acetamide

Starting Compound: Example 164

EXAMPLE 261

N-Cyclobutyl-3-(2,3-dihydro-1H-benzo[f]thiochromen-10-yl)-propanamide

Dissolve the product obtained in Example 245 (2 mmol) in 80 ml of methanol and cool with the aid of a bath of ice and salt. Add magnesium (80 mmol) in small portions and stir for 16 hours at ambient temperature. Add 30 cm$^3$ of 6N hydrochloric acid solution dropwise, while continuing to stir. Leave to cool, extract with ether, wash the organic phase with water, dry over magnesium sulphate, filter and concentrate under reduced pressure. The residue is chromatographed on silica gel to yield the title product.

In Examples 262 to 267 the procedure is the same as in Example 261, using appropriate reactants.

EXAMPLE 262

Methyl 3-[(cyclopropylcarbonyl)amino]-2-(2,3-dihydro-1H-benzo[f]thiochromen-10-yl)propanoate Starting Compound: Example 247

EXAMPLE 263

N-[3-(7,7-Dimethyl-8,9-dihydro-7H-thiochromeno[6,5-b]furan-1-yl)-propyl]acetamide Starting Compound: Example 251

EXAMPLE 264

O-{[(7-tert-Butyl)-8,9-dihydro-7H-thieno[3,2-f]thiochromen-1-yl]methyl}-N-thiopropionylhydroxylamine Starting Compound: Example 252

EXAMPLE 265

N-{2-[2-(2-Methoxyphenyl)-3-methyl-3,7,8,9-tetrahydropyrrolo[3,2-d]pyridin-1-yl]ethyl}acetamide Starting Compound: Example 254

EXAMPLE 266

N-[2-(2-Benzyl-7,8,9,10-tetrahydrothiepino[3',2':3,4]benzo[b]furan-1-yl)-ethyl]-1-cyclopropanecarboxamide Starting Compound: Example 256

EXAMPLE 267

N-[2-(2,3,9,10-Tetrahydro-8H-thiochromeno[5,6-b][1,4]dioxin-2-yl)-ethyl]acetamide Starting Compound: Example 259

EXAMPLE 268

N-[2-(7-Amino-1-naphthyl)ethyl]-2-phenylacetamide

Step A: N-[2-(7-Vinyl-1-naphthyl)ethyl]-2-phenylacetamide 15 mmol of the product obtained in Preparation 160, 16 mmol of vinyltributyltin and 0.43 mmol of tetrakis(triphenylphosphine)palladium are heated in 30 ml of N-methylpyrrolidinone at 110° C. for 3 hours, with stirring. After evaporating off the solvent, the residue is taken up in 20 ml of dichloromethane and treated with 10% aqueous potassium fluoride solution. After extraction, concentration under reduced pressure and chromatography on silica gel, the pure title product is obtained.

Step B: N-[2-(7-Formyl-1 naphthyl)ethyl]-2-phenylacetamide

To a solution of 10 mmol of the product obtained in Step A in a mixture of 50 ml of dioxane and 25 ml of water there are added, at ambient temperature, 1.10 g of osmium tetroxide in 2-methyl-2-propanol and then 8.70 g of sodium periodate. After stirring overnight at ambient temperature, the suspension is filtered and the filtrate is concentrated under reduced pressure. The residue obtained is taken up in dichloromethane. The organic phase is washed with water, dried and evaporated. The residue is purified by chromatography on silica gel to yield the title product.

Step C: 8-{2-[(2-Phenylacetyl)amino]ethyl}-2-naphthoic acid 2.7 g of potassium permanganate in 50 ml of an acetone/water mixture (50/50) are added, at ambient temperature, to a solution of 6.88 mmol of the product obtained in Step B in 30 ml of acetone. The solution is stirred for 2 hours at ambient temperature and is then filtered. The filtrate is concentrated under reduced pressure and chromatographed on silica gel to yield the title product.

Step D: 8-{2-[(2-Phenylacetyl)amino]ethyl}-2-naphthalenecarbonyl chloride 5 mmol of the product obtained in Step C are dissolved in 40 ml of thionyl chloride. After stirring under an inert atmosphere for 1 hour, the thionyl chloride is evaporated off under reduced pressure to yield the title product.

87

Step E: N-[2-(7-Amino-1-naphthyl)ethyl]-2-phenylacetamide

A solution of the product obtained in Step D (20 mmol) in dichloromethane (30 ml) containing tetrabutylammonium bromide (20 mg) is cooled in an ice bath. After adding sodium azide (24 mmol) dissolved in 5 ml of water, the solution is stirred vigorously at 0° C. for 2 hours. The organic phase is separated off, washed with water (2×5 ml) and dried over magnesium sulphate. After filtration, trifluoroacetic acid (30 mmol) is added and the solution is stirred under reflux for 60 hours. After cooling, the organic phase is washed with saturated sodium hydrogen carbonate solution (2×5 ml) and is concentrated under reduced pressure. The residue is then taken up in methanol (20 ml); water (80 ml) and then potassium carbonate (30 mmol) are added. After stirring at ambient temperature for 20 hours, the reaction mixture is concentrated under reduced pressure to a volume of about 60 ml and is then extracted 3 times with ether (3×50 ml). After drying over sodium sulphate, the organic phase is filtered and then evaporated under reduced pressure. The residue is chromatographed on silica gel to yield the title product.

In Examples 269 to 289 the procedure is as in Example 268, starting from the appropriate substrate.

EXAMPLE 269

N-[2-(7-Amino-1-naphthyl)ethyl]-2-bromoacetamide

Starting Compound: Preparation 198

EXAMPLE 270

N-[2-(7-Amino-8-hexyl-1-naphthyl)ethyl]-2-phenylacetamide

Starting Compound: Preparation 199

EXAMPLE 271

N-Cyclohexyl-4-(7-amino-1-naphthyl)butanamide

Starting Compound: Preparation 200

EXAMPLE 272

N-[3-(7-Amino-1-naphthyl)propyl]acetamide

Starting Compound: Preparation 201

EXAMPLE 273

N-[2-(2-Amino-1-naphthyl)-1-methylethyl]propanamide

Starting Compound: Preparation 202

EXAMPLE 274

N-[2-(7-Amino-3-benzoyl-1-naphthyl)ethyl]-N'-propylurea

Starting Compound: Preparation 167

88

EXAMPLE 275

N-{2-[7-Amino-3-(cyclopropylmethyl)-1-naphthyl]ethyl}acetamide

Starting Compound: Preparation 203

EXAMPLE 276

N-Methyl-4-(5-aminobenzo[b]furan-3-yl)butanamide

Starting Compound: Preparation 204

EXAMPLE 277

N-[2-(5-Aminothieno[3,2-b]pyridin-3-yl)ethyl]acetamide

Starting Compound: Preparation 205

EXAMPLE 278

N-[2-(5-Amino-1H-3-indolyl)ethyl]benzamide

Starting Compound: Preparation 206

EXAMPLE 279

N-{2-[5-Amino-2-(4-fluorobenzyl)-1-methyl-1H-pyrrolo[2,3-b]pyridin-3-yl]ethyl}acetamide Starting Compound: Preparation 172

EXAMPLE 280

N-[2-(5-Amino-2-benzylbenzo[b]furan-3-yl)ethyl]-1-cyclopropane-carboxamide

Starting Compound: Preparation 207

EXAMPLE 281

N-[(6-Amino-3,4-dihydro-2H-3-chromenyl)methyl]acetamide

Starting Compound: Preparation 174

EXAMPLE 282

N-[(6-Amino-2-phenyl-2H-3-chromenyl)methyl]butanamide

Starting Compound: Preparation 208

EXAMPLE 283

N-[2-(6-Amino-2,3-dihydro-1,4-benzodioxin-5-yl)ethyl]acetamide

Starting Compound: Preparation 179

EXAMPLE 284

N-[(9-Amino-2,3-dihydro-1H-benzo[f]chromen-2-yl)methyl]-2-cyclopropylacetamide

Starting Compound: Preparation 180

EXAMPLE 285

N-(4-Amino-2,3-dihydro-1H-2-phenalenyl)-N'-cyclopropylthiourea

Starting Compound: Preparation 181

EXAMPLE 286

N-[2-(7-Amino-3-phenyl-1-naphthyl)ethyl]acetamide

Starting Compound: Preparation 243

EXAMPLE 287

N-(6-Amino-1,3,4,5-tetrahydrobenzo[cd]indol-4-yl)acetamide

Starting Compound: Preparation 182

EXAMPLE 288

N-Cyclobutyl-6-amino-4,5-dihydro-3H-benzo[cd]isobenzofuran-4-carboxamide

Starting Compound: Preparation 183

EXAMPLE 289

N-[2-(7-Amino-3-naphthyl-1-naphthyl)ethyl]heptanamide

Starting Compound: Preparation 184

EXAMPLE 290

N-{2-[7-(Diethylamino)-1-naphthyl]ethyl}-2-phenylacetamide

To a solution of the product of Preparation 160 (5 mmol), diethylamine (12 mmol) and sodium tert-butoxide (14 mmol) in dioxane (20 ml) there are added tris(dibenzylideneacetone)dipalladium (0.25 mmol, 1 mole percent of palladium) and tri(o-tolyl)phosphine (0.1 mmol). Heating is then carried out at 100° C., with stirring, until all the starting compound has been used up (monitored by HPLC). The solution is then cooled to ambient temperature and 150 ml of ether are added. The organic phase is washed with brine (75 ml) and is then dried over magnesium sulphate, filtered and concentrated under reduced pressure. The residue is then chromatographed on silica gel to yield the title product.

In Examples 291 to 315 the procedure is as in Example 290, starting from the appropriate Preparation.

EXAMPLE 291

N-[2-(8-Allyl-7-piperidino-1-naphthyl)ethyl]-N'-cyclobutylthiourea

Starting Compound: Preparation 161

EXAMPLE 292

N-Cyclopropylmethyl-2-[7-(3,5-dimethylpiperazino)-1-naphthyl]acetamide

Starting Compound: Preparation 162

EXAMPLE 293

N-Methyl-N-{2-[7-(methylanilino)-1-naphthyl]ethyl}-N'-propylurea

Starting Compound: Preparation 163

EXAMPLE 294

Methyl 2-[7-(1H-1-imidazolyl)-1-naphthyl]-3-[(2,2,2-trifluoroacetyl)-amino]propanoate Starting Compound: Preparation 164

EXAMPLE 295

N-{3-[7-(Benzyl[1-ethynyl]amino)-1-naphthyl]propyl}-1-cyclohexanecarboxamide

Starting Compound: Preparation 165

EXAMPLE 296

N-{2-[7-(Hexylamino)-1,2,3,4-tetrahydro-1-naphthyl]ethyl}acetamide

Starting Compound: Preparation 244

EXAMPLE 297

N-{2-3-Benzoyl-7-(propylamino)-1-naphthyl]ethyl}-N'-propylurea

Starting Compound: Preparation 167

EXAMPLE 298

N-{3-[5-(Hexyl[2-propynyl]amino)benzo[b]furan-3-yl]propyl}acetamide

Starting Compound: Preparation 168

EXAMPLE 299

N-{[2-Benzyl-5-([1-ethyl-2-propynyl]amino)benzo[b]thiophen-3-yl]methyl}acetamide Starting Compound: Preparation 169

EXAMPLE 300

N-{2-[4-Allyl-5-(1-naphthylamino)benzo[b]thiophen-3-yl]ethyl}benzamide

Starting Compound: Preparation 170

EXAMPLE 301

N-[2-(5-Phenylamino-1H-3-indolyl)ethyl]-2-morpholinoacetamide

Starting Compound: Preparation 171

EXAMPLE 302

N-{2-[2-(4-Fluorobenzyl)-5-(1-propenylamino)-1-methyl-1H-pyrrolo-[2,3-b]pyridin-3-yl]ethyl}acetamide Starting Compound: Preparation 172

EXAMPLE 303

N-{2-[6-(Methylanilino)-1H-benzo[d]imidazol-1-yl]ethyl}-1-cyclopropanecarboxamide Starting Compound: Preparation 173

EXAMPLE 304

N-[(6-Piperidino-3,4-dihydro-2H-3-chromenyl)methyl]acetamide

Starting Compound: Preparation 174

EXAMPLE 305

N-{2-[6-(Butyl[3-butynyl]amino)-3,4-dihydro-2H-4-chromenyl]ethyl}-2-phenylacetamide Starting Compound: Preparation 175

EXAMPLE 306

N-[(6-Morpholino-2-phenyl-2H-3-chromenyl)methyl]acetamide

Starting Compound: Preparation 176

EXAMPLE 307

N-[2-(6-Anilino-3,4-dihydro-2H-4-thiochromenyl)ethyl]acetamide

Starting Compound: Preparation 177

EXAMPLE 308

N-{2-[7-(Benzyl[methyl]amino)-1,4-benzodioxin-2-yl]ethyl}-N'-propylurea

Starting Compound: Preparation 178

EXAMPLE 309

N-{2-[6-(Diethylamino)-2,3-dihydro-1,4-benzodioxin-5-yl]ethyl}-N'-acetamide

Starting Compound: Preparation 179

EXAMPLE 310

N-{[9-(4,4-Dimethylpiperidino)-2,3,7,8,9,10-hexahydro-1H-benzo[f]chromen-2-yl]methyl}-2-cyclopropylacetamide Starting Compound: Preparation 180

EXAMPLE 311

N-[4-(Benzylamino)-2,3-dihydro-1H-2-phenalenyl]-N'-cyclopropylthiourea

Starting Compound: Preparation 181

EXAMPLE 312

N-[6-(Methylanilino)-1,3,4,5-tetrahydrobenzo[cd]indol-4-yl]acetamide

Starting Compound: Preparation 182

EXAMPLE 313

N-Cyclobutyl-6-(4-isopropylanilino)-4,5-dihydro-3H-benzo[cd]isobenzofuran-4-carboxamide Starting Compound: Preparation 183

EXAMPLE 314

N-{2-[7-(3,5-Dimethylpiperazino)-3-naphthyl-1-naphthyl]ethyl}heptanamide

Starting Compound: Preparation 184

EXAMPLE 315

N-{2-[3-Phenyl-2-propenyl)-7-[(3-phenyl-2-propenyl]amino)-1-naphthyl]-ethyl}-2-cyclohexylacetamide Starting Compound: Preparation 185

In Examples 316 to 322 the procedure is as in Example 244.

EXAMPLE 316

N-[2-(3-Benzyl-3H-benzo[e]indol-9-yl)propyl]-1-cyclohexanecarboxamide

Starting Compound: Example 295

EXAMPLE 317

N-[3-(6-Hexyl-6,7-dihydrofuro[3,2-]quinolin-1-yl)propyl]acetamide

Starting Compound: Example 298

EXAMPLE 318

N-[(2-Benzyl-6-ethyl-6,7-dihydrothieno[3,2-f]quinolin-1-yl)methyl]acetamide

Starting Compound: Example 299

EXAMPLE 319

N-[2-(7-Butyl-1,2,3,7,8,9-hexahydrochromeno[6,5-b]azepin-1-yl)ethyl]-2-phenylacetamide Starting Compound: Example 305

EXAMPLE 320

N-Methyl-4-(7-oxo-7,8-dihydro-6H-furo[3,2':3,4]benzo[b]azepin-1-yl)-butanamide

Step A: N-{3-[4-(Methylamino)-4-oxobutyl]benzo[b]furan-5-yl}-3-butynamide

A solution of butanoic acid chloride (10 mmol), dissolved in ether (5 ml), is added dropwise to a solution of the product obtained in Example 276 (10 mmol) in ether (10 ml) and triethylamine (2 ml). The solution is stirred at ambient temperature until the amine has disappeared (monitored by TLC). At the end of the reaction, the organic phase is washed with water, dried, concentrated under reduced pressure and chromatographed on silica gel to yield the title product.

Step B: N-Methyl-4-(7-oxo-7,8-dihydro-6H-furo[3',2':3,4]benzo[b]azepin-1-yl)butanamide The procedure is as in Example 244, starting from the compound obtained in Step A.

EXAMPLE 321

N-[2-(9-Benzyl-4-oxo-4,5-dihydro-3H-furo[3',2':3,4]benzo[d][1,3]diazepin-10-yl)ethyl]-1-cyclopropanecarboxamide Step A: N-{2-[2-Benzyl-5-{[(1-ethynylamino)carbonyl]amino}benzo[b]furan-3-yl]ethyl}-1-cyclopropanecarboxamide A solution of cyclohexyl isocyanate in dichloromethane (5 ml), is added dropwise to a solution of the product obtained in Example 280 (10 mmol) in dichloromethane (10 ml). Stirring is carried out at ambient temperature until the starting amine has disappeared (monitored by TLC); the reaction mixture is then evaporated and concentrated under reduced pressure and is then chromatographed on silica gel to yield the title product.

Step B: N-[2-(9-Benzyl-4-oxo-4,5-dihydro-3H-furo[3',2':3,4]benzo[d][1,3]diazepin-10-yl)ethyl]-1-cyclopropanecarboxamide The procedure is as in Example 244, starting from the compound obtained in Step A.

EXAMPLE 322

N-Methyl-4-(4-thioxo-4,5-dihydro-3H-furo[3',2':3,4]benzo[d][1,3]diazepin-10-yl)butanamide Step A: N-Methyl-4-{5-[([1-ethylamino]carbothioyl)amino]benzo[b]furan-3-yl}butanamide The procedure is as in Step A of Example 321, but the cyclohexyl isocyanate is replaced by 1-isothiocyanotoacetylene to obtain the title product.

Step B: N-Methyl-4-(4-thioxo-4,5-dihydro-3H-furo[3',2':3,4]benzo[d][1,3]diazepin-10-yl)butanamide The procedure is as in Example 244, starting from the compound obtained in Step A.

In Examples 323 to 327 the procedure is as in Example 210, starting from appropriate substrates.

EXAMPLE 323

Ethyl 9-[2-phenylacetylamino)ethyl]-1-methyl-3H-benzo[e]indole-2-carboxylate

Starting Compound: Example 268

EXAMPLE 324

Ethyl 10-[4-(cyclohexylamino)-4-oxobutyl]-3,4-dihydrobenzo[f]quinoline-3-carboxylate Starting Compound: Example 271

EXAMPLE 325

Ethyl 9-[2-(acetylamino)ethyl]-7-(cyclopropylmethyl)-3H-benzo[e]indole-2-carboxylate Starting Compound: Example 275

EXAMPLE 326

Ethyl 2-[(butyrylamino)methyl]-3-phenyl-7,8-dihydro-3H-pyrano[3,2-f]quinoline-8-carboxylate Starting Compound: Example 282

EXAMPLE 327

Ethyl 10-[2-(heptanoylamino)ethyl]-1-isopropyl-8-naphthyl-3,4-dihydro-benzo[f]quinoline-3-carboxylate Starting Compound: Example 289

EXAMPLE 328

N-[2-(1-Methyl-3H-benzo[e]indol-9-yl)ethyl]benzamide

The compound obtained in Example 323 (5 mmol) is dissolved in ethanol (10 ml), to which 2N sodium hydroxide solution (6 ml) is added. The reaction mixture is heated at reflux until the reaction has ceased. Half the solvent is evaporated off. Extraction is carried out once with ether and then the aqueous phase is acidified to pH=1 with 1N potassium hydrogen sulphate solution. The aqueous phase is then extracted with ethyl acetate. The organic phase is washed with water, dried over magnesium sulphate and concentrated under reduced pressure. The residue is chromatographed on silica gel to yield the title product.

In Examples 329 to 331 the procedure is as in Example 328, starting from appropriate substrates.

EXAMPLE 329

N-Cyclohexyl-4-(3,4-dihydrobenzo[f]quinolin-10-yl)butanamide

Starting Compound: Example 324

EXAMPLE 330

N-[(3-Phenyl-7,8-dihydro-3H-pyrano[3,2-f]quinolin-2-yl)methyl]butanamide

Starting Compound: Example 326

EXAMPLE 331

N-[2-(1-Isopropyl-8-naphthyl-3,4-dihydrobenzo[f]quinolin-10-yl)ethyl]heptanamide Starting Compound: Example 327

EXAMPLE 332

N-[2-(4-Methyl-1-oxo-1,2,3,4-tetrahydrobenzo[f]quinolin-10-yl)ethyl]-2-phenylacetamide Step A: Ethyl 3-{methyl-[8-(2-{[2-phenylacetyl]amino}ethyl)-2-naphthyl]amino}propanoate The procedure is as in Example 290, but the diethylamine is replaced by ethyl N-methyl-3-aminopropanoate.

Step B: 3-[Methyl(8-{2-[(2-phenylacetyl)amino]ethyl}-2-naphthyl)amino]propanoic Acid An aqueous 0.5N solution of $K_2CO_3$ (10 ml) is added to the product obtained in Step A (4 mmol) dissolved in methanol (10 ml). When the reaction has ceased, the solution is acidified to pH 6–7 using 1N hydrochloric acid solution. The reaction mixture is extracted with dichloromethane. The organic phase is washed with water, dried over magnesium sulphate and concentrated under reduced pressure. The residue is chromatographed on silica gel to yield the title product.

Step C: 3-[Methyl-(8-{2-[(2-phenylacetyl)amino]ethyl}-2-naphthyl)amino]propanoyl chloride The product obtained in Step B (3 mmol), dissolved in thionyl chloride, is stirred at 60° C. under a stream of nitrogen for one hour. The thionyl chloride is evaporated off under reduced pressure and the residue is dried using a vane pump to yield the title product.

Step D: N-[2-(4-Methyl-1-oxo-1,2,3,4-tetrahydrobenzo[f]quinolin-10-yl)ethyl]-2-phenylacetamide The product obtained in Step C (3 mmol), dissolved in 1,1,2,2-tetrachloroethane (30 ml), is added dropwise to a solution of aluminium chloride (10 mmol) in the same solvent (20 ml) under nitrogen. The reaction mixture is heated at 60° C., with stirring, until the reaction has ceased and it is then poured into a mixture of ice (10 g) and concentrated HCl (0.3 ml); stirring is continued for one hour. The aqueous phase is extracted twice with chloroform; the combined organic phases are then dried over magnesium sulphate and concentrated under reduced pressure. The residue is chromatographed on silica gel to yield the title product.

In Examples 333 to 337 the procedure is as in Example 332, but starting from appropriate reactants.

EXAMPLE 333

N-[2-(7-Benzoyl-1-oxo-3-phenyl-2,3-dihydro-1H-benzo[e]indol-9-yl)ethyl]-N'-propylurea Starting Compound: Preparation 167

EXAMPLE 334

N-Methyl-4-(6-isopropyl-9-oxo-6,7,8,9-tetrahydrofuro[3,2-f]quinolin-1-yl)butanamide Starting Compound: Preparation 168

EXAMPLE 335

N-{2-[2-(4-Fluorobenzyl)-3-methyl-9-oxo-6,7,8,9-tetrahydro-3H-pyrrolo-[3,2-f][1,7]naphthyridin-1-yl]ethyl}acetamide Starting Compound: Preparation 172

EXAMPLE 336

N-[2-(8,8-Dimethyl-9-oxo-8,9-dihydro-7H-[1,4]dioxino[2,3-e]indol-2-yl)-ethyl]-N'-propylurea Starting Compound: Preparation 178

EXAMPLE 337

N-(2-{4-Benzyl-1-oxo-8-[3-phenyl-2-propenyl]-1,2,3,4-tetrahydrobenzo-[f]quinolin-10-yl}ethyl)-2-cyclohexylacetamide Starting Compound: Preparation 185

EXAMPLE 338

N-[2-(4-Methyl-1,2,3,4-tetrahydro[f]quinolin-10-yl)ethyl]-2-phenylacetamide

The product of Example 332 (3 mmol) is dissolved in acetic acid (70 ml). After several purges with argon, 10% palladium-on-carbon (600 mg) is added and the mixture is placed under a hydrogen atmosphere. Stirring is carried out at ambient temperature until the reaction is complete (monitored by TLC) and the palladium is filtered off over Celite. The acetic acid is evaporated off to dryness and the residue is chromatographed on silica gel to yield the title product.

In Examples 339 to 342 the procedure is as in Example 338, starting from appropriate reactants.

EXAMPLE 339

N-[2-(7-Benzoyl-3-phenyl-2,3-dihydro-1H-benzo[e]indol-9-yl)ethyl]-N'-propylurea

Starting Compound: Example 333

EXAMPLE 340

N-Methyl-4-(6-isopropyl-6,7,8,9-tetrahydrofuro[3,2-f]quinolin-1-yl)-butanamide

Starting Compound: Example 334

EXAMPLE 341

N-[2-(8,8-Dimethyl-8,9-dihydro-7H-[1,4]dioxino[2,3-e]indol-2-yl)ethyl]-N'-propylurea Starting Compound: Example 336

EXAMPLE 342

N-[2-{4-Benzyl-8-[3-phenyl-2-propenyl]-1,2,3,4-tetrahydrobenzo[f]quinolin-10-yl}ethyl)-2-cyclohexylacetamide Starting Compound: Example 337

EXAMPLE 343

N-Cyclopropylmethyl-2-(1-hydroxy-2,3-dihydro-1H-benzo[f]thiochromen-10-yl)acetamide A solution of the product obtained in Example 219 (2 mmol) dissolved in methanol (10 ml) is added dropwise to a suspension of sodium hydride (2.2 mmol) in methanol (50 ml) at −40° C. Stirring is carried out until the starting compound has completely disappeared (about 3 hours). At the end of the reaction, the solution is poured into water (30 ml). The reaction mixture is concentrated under reduced pressure to a volume of about 30 ml and is then extracted with ethyl acetate. The aqueous phase is washed with water, dried over magnesium sulphate and concentrated under reduced pressure. The residue is chromatographed on silica gel to yield the title product.

In Examples 344 to 349, the procedure is as in Example 343, but the product of Example 219 is replaced by the product of the appropriate Example.

EXAMPLE 344

N-Methyl-4-(8-hydroxy-7,7-dimethyl-7,8-dihydrothieno[3',2':3,4]benzo-[f]furan-1-yl)butanamide Starting Compound: Example 223

EXAMPLE 345

N-[2-(9-Hydroxy-7,7-dimethyl-3,7,8,9-tetrahydrothiopyrano[3,2-e]indol-1-yl)ethyl]benzamide Starting Compound: Example 225

EXAMPLE 346

N-[(3-Benzyl-9-hydroxy-8,9-dihydrothieno[2',3':5,6]benzo[b][1,4]dioxin-2-yl)methyl]acetamide Starting Compound: Example 228

EXAMPLE 347

N-[2-(1-Hydroxy-4-methyl-1,2,3,4-tetrahydrobenzo f]quinolin-10-yl)ethyl]-2-phenylacetamide Starting Compound: Example 332

EXAMPLE 348

N-Methyl-4-(9-hydroxy-6-isopropyl-6,7,8,9-tetrahydrofuro[3,2-f]quinolin-1-yl)butanamide Starting Compound: Example 334

EXAMPLE 349

N-{2-[2-(4-Fluorobenzyl)-9-hydroxy-3-methyl-6,7,8,9-tetrahydro-3H-pyrrolo[3,2-f][1,7]naphthyridin-1-yl]ethyl}acetamide Starting Compound: Example 335

Examples 350 to 353 are obtained by proceeding as in Example 268, starting from appropriate substrates.

EXAMPLE 350

N-[2-(5-Aminobenzo[b]furan-3-yl)ethyl]acetamide

Starting Compound: Preparation 246

EXAMPLE 351

N-[2-(7-Amino-1,2,3,4-tetrahydro-1-naphthyl)ethyl]acetamide

Starting Compound: Preparation 244

EXAMPLE 352

N-[2-(6-Amino-2,3-dihydro-1H-1-indenyl)ethyl]acetamide

Starting Compound: Preparation 241

EXAMPLE 353

N-{2-[5-(Methylamino)benzo[b]furan-3-yl)ethyl]acetamide

The procedure is as in Example 290, starting from Preparation 246.

EXAMPLE 354

N-{2-[7-(Methylsulphinyl)-1-naphthyl]ethyl}acetamide 1 eq. of the compound obtained in Example 1 is dissolved in anhydrous dichloromethane and is cooled with the aid of an ice bath. A solution of 1 eq. of m-chloroperbenzoic acid in dichloromethane is added dropwise and the mixture is stirred until the reaction is complete (monitored by TLC). The solvent is then evaporated off in vacuo and the residue obtained is taken up in saturated $Na_2CO_3$ solution. The precipitate formed, which corresponds to the title product, is filtered off.

EXAMPLE 355

N-{2-[7-(Methylsulphonyl)-1-naphthyl]ethyl}acetamide

The procedure is as in Example 354 using 3 eq. of m-chloroperbenzoic acid.

EXAMPLE 356

N-{2-[7-(Methylthio)-1,2,3,4-tetrahydro-1-naphthyl]ethyl}acetamide

Step A: 4-[4-(Methylthio)phenyl]-4-oxobutanoic acid

In a 500 ml flask with a ground neck, 0.17 mol of succinic anhydride is added to a solution of 0.17 mol of thioanisole in 140 ml of tetrachloroethane. The mixture is cooled with the aid of an ice bath, and 0.34 mol of aluminium chloride is added in small portions. The mixture is then heated at 60° C. for 3 hours. The reaction mixture is then cooled, poured into ice-cold water and acidified with 3M HCl solution. The precipitate formed is filtered off under suction, washed with cyclohexane and recrystallised.

Melting point=153–155° C.

Step B: 4-[4-(Methylthio)phenyl]butanoic acid

In a 500 ml round-bottomed flask, 0.088 mol of the compound obtained in Step A is dissolved in 0.881 ml of trifluoroacetic acid. The solution is cooled to 0° C. with the aid of an ice bath and 0.220 ml of triethylsilane hydride is added with the aid of a dropping funnel. The reaction mixture is stirred for 18 hours at ambient temperature and is then hydrolysed. The precipitate formed is filtered off under suction, is washed with water and with cyclohexane and is then dissolved in ethyl acetate. The organic phase is dried over $MgSO_4$ and evaporated to obtain the title product in the form of a white solid.

Melting point=53–55° C.

Step C: 7-(Methylthio)-3,4-dihydro-1(2H)-naphthalenone 0.055 mol of the compound obtained in Step B and 100 g of polyphosphoric acid are introduced into a 500 ml round-bottomed flask. The reaction mixture is heated at 60° C. for 3 hours and is then cooled and poured into water. Extraction with ethyl ether is carried out; the organic phase is washed with water, dried over $MgSO_4$ and evaporated under reduced pressure. The residue obtained is purified by chromatography on silica gel. Yellow oil Step D: 2-[7-(Methylthio)-3,4-dihydro-1(2H)-naphthalenylidene]acetonitrile 0.041 ml of sodium hydride is suspended in 30 ml of anhydrous tetrahydrofuran under a nitrogen atmosphere in a 250 ml three-necked flask. Cooling is carried out in a bath of ice/salt and 0.041 ml of diethyl cyanomethylenephosphonate diluted with 40 ml of anhydrous tetrahydrofuran is added dropwise; magnetic stirring is carried out for 45 minutes. Whilst still cold, 0.031 mol of the compound obtained in Step C, dissolved in 30 ml of anhydrous tetrahydrofuran, is added dropwise. Stirring is carried out under a nitrogen atmosphere for 3 hours at ambient temperature. The reaction mixture is poured onto a mixture of water/ice, is acidified with aqueous 3M hydrochloric acid solution and is extracted 3 times with ethyl ether. The organic phase is dried over $MgSO_4$ and is evaporated. The residue obtained is recrystallised.

Melting point=59–61° C.

Step E: 2-[7-(Methylthio)-1,2,3,4-tetrahydro-1-naphthyl]-1-ethylamine hydrochloride 0.0046 mol of the compound obtained in Step D is dissolved in 70 ml of methanol. 0.0092 mol of cobalt chloride is added, with magnetic stirring, and then, in small portions, 0.0325 ml of sodium borohydride. Stirring is carried out for 3 hours at ambient temperature and the mixture is then acidified with 6M hydrochloric acid solution until the black precipitate dissolves. The methanol is evaporated off under reduced pressure and then extraction with ethyl ether is carried out. The two phases are separated, and the aqueous phase is then rendered alkaline with 20% ammonium hydroxide solution. Extraction with ethyl ether is carried out twice; the organic phase is dried over magnesium sulphate and evaporated under reduced pressure. The oil obtained is dissolved in alcohol at 95° C. and then an ethanolic solution saturated with HCl is added. The solvent is evaporated off under reduced pressure and the residue obtained is recrystallised.

Step F: N-{2-[7-(Methylthio)-1,2,3,4-tetrahydro-1-naphthyl]ethyl}acetamide

In a 50 ml round-bottomed flask, 0.0025 mol of the compound obtained in Step E is dissolved in 5 ml of pyridine. The solution is cooled with the aid of an ice bath and 5 ml of acetic anhydride are added dropwise. Stirring is carried out for 5 hours at ambient temperature. The reaction mixture is poured into aqueous 3M hydrochloric acid solution and is then extracted with ethyl ether. The organic phase is washed with aqueous 10% potassium carbonate solution and then with water, is dried over magnesium sulphate and is evaporated under reduced pressure. The residue obtained is recrystallised.

EXAMPLE 357

N-{2-[7-(Methylsulphinyl)-1,2,3,4-tetrahydro-1-naphthyl]ethyl}acetamide

The procedure is as in Example 354, starting from the compound obtained in Example 356.

EXAMPLE 358

N-{2-[7-(Methylsulphonyl)-1,2,3,4-tetrahydro-1-naphthyl]ethyl}acetamide

The procedure is as in Example 355, starting from the compound obtained in Example 356.

EXAMPLE 359

N-{2-[7-(Methylsulphinyl)-1-naphthyl]ethyl}butanamide

The procedure is as in Example 354, starting from the compound obtained in Example 2.

EXAMPLE 360

N-{2-[7-(Methylsulphonyl)-1-naphthyl]ethyl}butanamide

The procedure is as in Example 355, starting from the compound obtained in Example 2.

EXAMPLE 361

N-{2-[7-(Methylsulphinyl)-1-naphthyl]ethyl}cyclopropanecarboxamide

The procedure is as in Example 354, starting from the compound obtained in Example 3.

EXAMPLE 362

N-{2-[7-(Methylsulphonyl)-1-naphthyl]ethyl}cyclopropanecarboxamide

The procedure is as in Example 355, starting from the compound obtained in Example 3.

EXAMPLE 363

2,2,2-Trifluoro-N-{2-[7-(methylsulphinyl)-1-naphthyl]ethyl}acetamide

The procedure is as in Example 354, starting from the compound obtained in Example 4.

EXAMPLE 364

2,2,2-Trifluoro-N-{2-[7-(methylsulphonyl)-1-naphthyl]ethyl}acetamide

The procedure is as in Example 355, starting from the compound obtained in Example 4.

EXAMPLE 365

N-Methyl-N'-{2-[7-(methylsulphinyl)-1-naphthyl]ethyl}urea

The procedure is as in Example 354, starting from the compound obtained in Example 5.

EXAMPLE 366

N-Methyl-N'-{2-[7-(methylsulphonyl)-1-naphthyl]ethyl}urea

The procedure is as in Example 355, starting from the compound obtained in Example 5.

EXAMPLE 367

N-{2-[3-Benzoyl-7-(methylsulphinyl)-1-naphthyl]ethyl}acetamide

The procedure is as in Example 354, starting from the compound obtained in Example 6.

EXAMPLE 368

N-{2-[3-Benzoyl-7-(methylsulphonyl)-1-naphthyl]ethyl}acetamide

The procedure is as in Example 355, starting from the compound obtained in Example 6.

EXAMPLE 369

N-{2-[3-Benzyl-7-(methylsulphinyl)-1-naphthyl]ethyl}acetamide

The procedure is as in Example 354, starting from the compound obtained in Example 7.

EXAMPLE 370

N-{2-[3-Benzyl-7-(methylsulphonyl)-1-naphthyl]ethyl}acetamide

The procedure is as in Example 355, starting from the compound obtained in Example 7.

EXAMPLE 371

N-{2-[7-(Ethylsulphinyl)-1-naphthyl]ethyl}acetamide

The procedure is as in Example 354, starting from the compound obtained in Example 8.

EXAMPLE 372

N-{2-[7-(Ethylsulphonyl)-1-naphthyl]ethyl}acetamide

The procedure is as in Example 355, starting from the compound obtained in Example 8.

EXAMPLE 373

N-{2-[7-(Propylsulphinyl)-1-naphthyl]ethyl}acetamide

The procedure is as in Example 354, starting from the compound obtained in Example 9.

EXAMPLE 374

N-{2-[7-(Propylsulphonyl)-1-naphthyl]ethyl}acetamide

The procedure is as in Example 355, starting from the compound obtained in Example 9.

EXAMPLE 375

N-{2-[7-(Benzylthio)-1-naphthyl]ethyl}acetamide 4.4 mmol of the compound obtained in Preparation 2 are dissolved in 20 ml of dichloromethane and the whole is introduced into a two-necked flask surmounted by a condenser and equipped with a septum under a current of nitrogen. 6.5 mmol of benzylthiol are added by means of a syringe, and then 8.8 mmol of triflic acid. The mixture is heated at the reflux of dichloromethane for 24 hours. The mixture is cooled and then hydrolysed using 10% $Na_2CO_3$ solution. The organic phase is washed with 10% sodium hydroxide solution and then with water, until the washing waters are neutral, and is dried over $MgSO_4$, filtered and evaporated. The residue is taken up in ether and the precipitate formed is filtered off. The filtrate is evaporated, taken up in petroleum ether and the precipitate formed is filtered and then recrystallised from a mixture of toluene/cyclohexane (1/4).

Melting point=80–83° C.

EXAMPLE 376

N-{2-[7-(Benzylsulphinyl)-1-naphthyl]ethyl}acetamide

The procedure is as in Example 354, starting from Example 375.

EXAMPLE 377

N-{2-[7-(Benzylsulphonyl)-1-naphthyl]ethyl}acetamide

The procedure is as in Example 355, starting from Example 375.

Pharmacological Study

EXAMPLE A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

EXAMPLE B

Melatonin Receptor Binding Study on Pars Tuberalis Cells of Sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol
1) Sheep pars tuberalis membranes are prepared and used as target tissue in saturation experiments to determine the binding capacities and affinities for 2-[$^{125}$I]-iodomelatonin.
2) Sheep pars tuberalis membranes are used as target tissue in competitive binding experiments using the various test compounds in comparison with melatonin.

Each experiment is carried out in triplicate and a range of different concentrations is tested for each compound. The results enable the determination, after statistical processing, of the binding affinities of the compound tested.

Results

The compounds of the invention appear to have a strong affinity for melatonin receptors.

EXAMPLE C

Melatonin $mt_1$ and $MT_2$ Receptor Binding Study

The $mt_1$ or $MT_2$ receptor binding experiments are carried out using 2-[$^{125}$I]-melatonin as reference radioligand. The radioactivity retained is determined using a liquid scintillation counter.

Competitive binding experiments are then carried out in triplicate using the various test compounds. A range of different concentrations is tested for each compound. The results enable the binding affinities of the compounds tested ($IC_{50}$) to be determined.

The $IC_{50}$ values found for the compounds of the invention demonstrate binding to one or other of the $mt_1$ or $MT_2$ receptor sub-types, the values being $\leq 10$ µM.

EXAMPLE D

Action of the Compounds of the Invention on the Circadian Rhythms of Locomotive Activity of the Rat The involvement of melatonin in influencing, by day/night alternation, the majority of physiological, biochemical and behavioural circadian rhythms has made it possible to establish a pharmacological model for research into melatoninergic ligands.

The effects of the molecules are tested on numerous parameters and, in particular, on the circadian rhythms of locomotive activity, which are a reliable indicator of the endogenous circadian clock.

In this study, the effects of such molecules on a particular experimental model, namely the rat placed in temporal isolation (permanent darkness), is evaluated.

Experimental Protocol

One-month-old male rats are subjected, as soon as they arrive at the laboratory, to a light cycle of 12 hours' light per 24 hours (LD 12:12).

After 2 to 3 weeks' adaptation, they are placed in cages fitted with a wheel connected to a recording system, in order to detect the phases of locomotive activity and thus monitor the nychthemeral rhythms (LD) or circadian rhythms (DD).

As soon as the rhythms recorded show a stable pattern during the light cycle LD 12:12, the rats are placed in permanent darkness (DD).

Two to three weeks later, when the free course (rhythm reflecting that of the endogenous clock) is clearly established, the rats are given a daily administration of the molecule to be tested.

The observations are made by means of visualisation of the rhythms of activity:
- influence on the rhythms of activity by the light/dark cycle,
- disappearance of the influence on the rhythms in permanent darkness,
- influence on the activity by the daily administration of the molecule; transitory or durable effect.

A software package makes it possible:
- to measure the duration and intensity of the activity, the period of the rhythm of the animals during free course and during treatment,
- possibly to demonstrate by spectral analysis the existence of circadian and non-circadian (for example ultradian) components.

Results

The compounds of the invention clearly appear to allow powerful action on the circadian rhythm via the melatoninergic system.

EXAMPLE E

Light/Dark Cages Test

The compounds of the invention are tested on a behavioural model, the light/dark cages test, which allows the anxiolytic activity of the compounds to be demonstrated.

The apparatus consists of two polyvinyl boxes covered with Plexiglass. One of the boxes is in darkness. A lamp is placed above the other box, yielding a light intensity of approximately 4000 lux in the centre of the box. An opaque plastic tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

After administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE F

Activity of Compounds of the Invention on the Caudal Artery of the Rat

The compounds of the invention were tested in vitro on the caudal artery of the rat. Melatoninergic receptors are present in those vessels, thus providing a relevant pharmacological model for studying melatoninergic ligand activity. The stimulation of the receptors can cause either vasoconstriction or dilation depending on the arterial segment studied.

Protocol

One-month old rats are accustomed to a light/dark cycle of 12 h/12 h during a period of 2 to 3 weeks.

After sacrifice, the caudal artery is isolated and maintained in a highly oxygenated medium. The arteries are then cannulated at both ends, suspended vertically in an organ chamber in a suitable medium and perfused via their proximal end. The pressure changes in the perfusion flow enable evaluation of the vasoconstrictive or vasodilatory effect of the compounds.

The activity of the compounds is evaluated on segments that have been pre-contracted by phenylephrine (1 µM). A concentration/response curve is determined non-cumulatively by the addition of a concentration of the test compound to the pre-contracted segment. When the observed effect reaches equilibrium, the medium is changed and the preparation is left for 20 minutes before the addition of the same concentration of phenylephrine and a further concentration of the test compound.

Results

The compounds of the invention significantly modify the diameter of caudal arteries pre-constricted by phenylephrine.

EXAMPLE G

Pharmaceutical Composition: Tablets

| | |
|---|---|
| 1000 tablets each comprising 5 mg of N-{2-[7-methylthio)-1-naphthyl-ethyl}acetamide (Example 1) | 5 g |
| wheat starch | 20 g |
| maize starch | 20 g |
| lactose | 30 g |
| magnesium stearate | 2 g |
| silica | 1 g |
| hydroxypropyl cellulose | 2 g |

We claim:

1. A compound selected from those of formula (I):

R-A-R'  (I)

wherein:
A represents:
a ring system of formula (II):

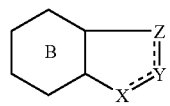

(II)

wherein
X represents oxygen or sulphur
Y represents $C(H)_q$ (wherein q is 0, 1 or 2),
Z represents $C(H)_q$ (wherein q is 0, 1 or 2),
B represents benzene, the symbol ----- means that the bonds may be single or double, it being understood that the valency of the atoms is respected, wherein R substitutes the ring B and R' substitutes the ring containing X, Y and Z, or R and R' substitute the ring B, it being understood that the ring system of formula (II) may be unsubstituted or substituted (in addition to the substituents R and R') by from 1 to 6 radicals, which may be the same or different, selected from $R_a$, $OR_a$, $COR_a$, $COOR_a$, $OCOR_a$, $OSO_2CF_3$, cyano, nitro and halogen, wherein $R_a$ represents hydrogen, unsubstituted or substituted linear or branched ($C_1$–$C_6$)alkyl, unsubstituted or substituted linear or branched ($C_2$–$C_6$)alkenyl, unsubstituted or substituted linear or branched ($C_2$–$C_6$)alkynyl, linear or branched ($C_1$–$C_6$)polyhaloalkyl, unsubstituted or substituted ($C_3$–$C_8$)cycloalkyl, unsubstituted or substituted ($C_3$–$C_8$)cycloalkyl-($C_1$–$C_6$)alkyl in which alkyl is linear or branched, unsubstituted or substituted ($C_3$–$C_8$)cycloalkenyl, unsubstituted or substituted ($C_3$–$C_8$)cycloalkenyl-($C_1$–$C_6$)alkyl in which alkyl is linear or branched, aryl, aryl-($C_1$–$C_6$)alkyl in which the alkyl moiety is linear or branched, aryl-($C_1$–$C_6$)alkenyl in which the alkenyl moiety is linear or branched, heteroaryl, heteroaryl-($C_1$–$C_6$)alkyl in which the alkyl moiety is linear or branched, heteroaryl-($C_1$–$C_6$)alkenyl in which the alkenyl moiety is linear or branched, unsubstituted or substituted linear or branched ($C_1$–$C_6$)heterocycloalkyl, unsubstituted or substituted heterocycloalkenyl, substituted or unsubstituted heterocycloalkyl-($C_1$–$C_6$)alkyl in which the alkyl moiety is linear or branched, or substituted or unsubstituted heterocycloalkenyl-($C_1$–$C_6$)alkyl in which the alkyl moiety is linear or branched, R represents:
a group of formula (V):

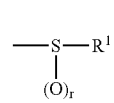

(V)

wherein
r is an integer such that 0≦r≦2,
$R^1$ represents halogen, $R_a$, $OR_a$, $COR_a$ or $COOR_a$, wherein $R_a$ is as defined hereinbefore, it being understood that R cannot represent $SO_3H$, —$NR'_aR''_a$ wherein $R'_a$ and $R''_a$, which may be the same or different, may take any of the values of $R_a$ and also may form, together with the nitrogen atom carrying them, a 5- to 10-membered cyclic group which may contain, in addition to the nitrogen atom, from one to three hetero atoms selected from oxygen, sulphur and nitrogen, and R' represents a group of formula (VII):

-G-$R^2$  (VII)

wherein

G represents an alkylene chain —(CH$_2$)$_t$— (wherein t is an integer such that 0≦t≦4), optionally substituted by one or more radicals, which may be the same or different, selected from R$_a$, OR$_a$, COOR$_a$, COR$_a$ (wherein R$_a$ is as defined hereinbefore) and halogen, and R$^2$ represents a group

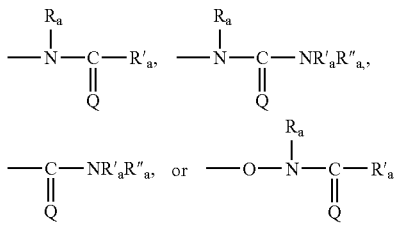

wherein Q is oxygen or sulfur, and R$_a$, R'$_a$ and R"$_a$ (which may be the same or different) are as defined hereinbefore, it being possible for R'$_a$ and R"$_a$ to form, together with nitrogen atom carrying them, a cyclic group as defined hereinbefore, it being understood that:

"heterocycloalkyl" is taken to mean any saturated mono- or poly-cyclic group containing from 5 to 10 atoms containing from 1 to 3 hetero atoms selected from nitrogen, oxygen and sulphur, "heterocycloalkenyl" is taken to mean any non-aromatic mono- or poly-cyclic group containing one or more unsaturations, containing from 5 to 10 atoms and which may contain from 1 to 3 hetero atoms selected from nitrogen, oxygen and sulphur, the term "substituted" used in respect of the expressions "alkyl", "alkenyl" and "alkynyl" indicates that the groups in question are substituted by one or more radicals, which may be the same or different, selected from hydroxy, linear or branched (C$_1$–C$_6$) alkoxy, linear or branched (C$_1$–C$_6$)alkyl, linear or branched (C$_1$–C$_6$)polyhaloalkyl, amino and halogen, the term "substituted" used in respect of the expressions "cycloalkyl", "cycloalkylalkyl", "cycloalkenyl", "cycloalkenylalkyl", "heterocycloalkyl", "heterocycloalkenyl", "heterocycloalkylalkyl" and "heterocycloalkenylalkyl" indicates that the cyclic moiety of the groups in question is substituted by one or more radicals, which may be the same or different, selected from hydroxy, linear or branched (C$_1$–C$_6$) alkoxy, linear or branched (C$_1$–C$_6$)alkyl, linear or branched (C$_1$–C$_6$)polyhaloalkyl, amino and halogen, "aryl" is taken to mean any aromatic, mono- or poly-cyclic group containing from 6 to 22 carbon atoms, and also the biphenyl group, "heteroaryl" is taken to mean any aromatic mono- or poly-cyclic group containing from 5 to 10 atoms containing from 1 to 3 hetero atoms selected from nitrogen, oxygen and sulphur, it being possible for the "aryl" and "heteroaryl" groups to be substituted by one or more radicals, which may be the same or different, selected from hydroxy, linear or branched (C$_1$–C$_6$)alkoxy, linear or branched (C$_1$–C$_6$)alkyl, linear or branched (C$_1$–C$_6$)polyhaloalkyl, cyano, nitro, amino and halogen, it being understood that:

when A represents a ring system of formula (IIa):

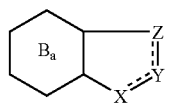

(IIa)

wherein X, Y, Z and the symbol ••••• are as defined hereinbefore, B$_a$ represents a benzene nucleus and R represents a group of formula (V), then R' cannot represent G-R$^2$ wherein G represents a single bond (t=0) and R$^2$ represents —CONR'$_a$R"$_a$ wherein R'$_a$ and R"$_a$ are as defined hereinbefore, its enantiomers and diastereoisomers, and addition salts thereof with a pharmaceutically acceptable acid or base.

2. A compound of claim 1, wherein A represents a ring system of formula (II) substituted in the 5-position by R and in the 3-position by R', its enantiomers and diastereoisomers, and addition salts thereof with a pharmaceutically acceptable acid or base.

3. A compound of claim 1, wherein R represents a group of formula (V), its enantiomers and diastereoisomers, and addition salts thereof with a pharmaceutically acceptable acid or base.

4. A compound of claim 1, wherein R represents NR'$_a$R"$_a$ its enantiomers and diastereoisomers, and addition salts thereof with a pharmaceutically acceptable acid or base.

5. A compound of claim 1, wherein R represents a group of formula (V) wherein r is 0 and R$^1$ represents R$_a$ as defined in claim 1, its enantiomers and diastereoisomers, and addition salts thereof with a pharmaceutically acceptable acid or base.

6. A compound of claim 1, wherein R' represents G-R$^2$ wherein G represents an unsubstituted or substituted alkylene chain —(CH$_2$)$_t$—, wherein t is 2 or 3, and and R$^2$ represents a group

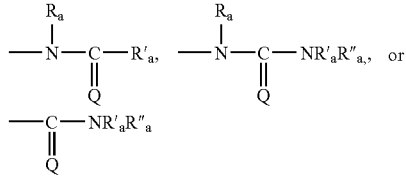

its enantiomers and diastereoisomers, and addition salts thereof with a pharmaceutically acceptable acid or base.

7. A compound of claim 1, wherein R' represents G-R$^2$ wherein G represents an alkylene chain —(CH$_2$)$_t$—, wherein t is 2 or 3, and R$^2$ represents —NHCOR'$_a$ or —CONHR'$_a$ wherein R'a is as defined in claim 1, its enantiomers and diastereoisomers, and addition salts thereof with a pharmaceutically acceptable acid or base.

8. A compound of claim 1, wherein A represents a ring system of formula (II) substituted in the 5-position by a group of formula (V) and in the 3-position by a group of formula (VII), its enantiomers and diastereoisomers, and addition salts thereof with a pharmaceutically acceptable acid or base.

9. A compound of claim 1, wherein A represents a ring system of formula (II) substituted in the 5-position by $-NR'_aR''_a$ and in the 3-position by a group of formula (VII), its enantiomers and diastereoisomers, and addition salts thereof with a pharmaceutically acceptable acid or base.

10. A compound of claim 1, wherein A represents a ring system of formula (II), which is substituted in the 5-position by a group of formula

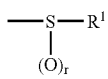   (V)

and substituted in the 3-position by a group of formula (VII) wherein G represents an unsubstituted or substituted chain $-(CH_2)_t-$, wherein t is 2 or 3, and $R^2$ represents

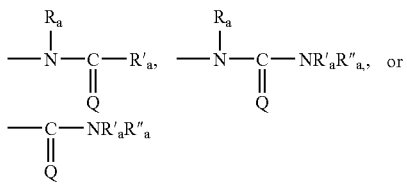

its enantiomers and diastereoisomers, and addition salts thereof with a pharmaceutically acceptable acid or base.

11. A compound of claim 1, wherein A represents a ring system of formula (II), which is substituted in the 5-position by a group of formula $-NR'_aR''_a$ and substituted in the 3-position by a group of formula (VII) wherein G represents an unsubstituted or substituted chain $-(CH_2)_t-$, wherein t is 2 or 3, and $R^2$ represents

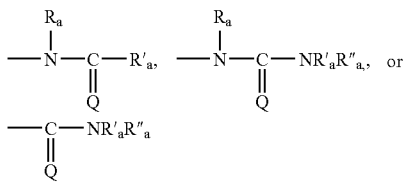

its enantiomers and diastereoisomers, and addition salts thereof with a pharmaceutically acceptable acid or base.

12. A compound of claim 1, wherein A represents benzofuran or dihydrobenzofuran, which is optionally substituted (in addition to the substituents R and R'), its enantiomers and diastereoisomers, and addition salts thereof with a pharmaceutically acceptable acid or base.

13. A compound of claim 1, wherein A represents benzofuran or dihydrobenzofuran, which is optionally substituted (in addition to the substituents R and R') in the 2-position, its enantiomers and diastereoisomers, and addition salts thereof with a pharmaceutically acceptable acid or base.

14. A compound of claim 1, wherein A represents benzothiophene or dihydrobenzothiophene, which is optionally substituted (in addition to the substituents R and R'), its enantiomers and diastereoisomers, and addition salts thereof with a pharmaceutically acceptable acid or base.

15. A compound of claim 1, wherein A represents benzothiophene or dihydrobenzothiophene, which is optionally substituted (in addition to the substituents R and R') in the 2-position, its enantiomers and diastereoisomers, and addition salts thereof with a pharmaceutically acceptable acid or base.

16. A compound of claim 1, wherein A represents benzofuran or dihydrobenzofuran, which is optionally substituted (in addition to the substituents R and R') in the 2-position, substituted in the 5-position by

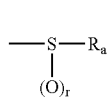

and substituted in the 3-position by $-(CH_2)_t-NHCOR'_a$ or $-(CH_2)_t-CONHR'_a$, wherein t is 2 or 3, its enantiomers and diastereoisomers, and addition salts thereof with a pharmaceutically acceptable acid or base.

17. A compound of claim 1, wherein A represents benzothiophene or dihydrobenzothiophene, which is optionally substituted (in addition to R and R') in the 2-position, substituted in the 5-position by

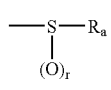

and substituted in the 3-position by $-(CH_2)_t-NHCOR'_a$ or $-(CH_2)_t-CONHR'_a$, wherein t is 2 or 3, its enantiomers and diastereoisomers, and addition salts thereof with a pharmaceutically acceptable acid or base.

18. A compound of claim 1, wherein A represents benzofuran or dihydrobenzofuran, which is optionally substituted (in addition to the substituents R and R') in the 2-position, substituted in the 5-position by $-NR'_aR''_a$ and substituted in the 3-position by $-(CH_2)_t-NHCOR'_a$ or $-(CH_2)_t-CONHR'_a$, wherein t is 2 or 3, its enantiomers and diastereoisomers, and addition salts thereof with a pharmaceutically acceptable acid or base.

19. A compound of claim 1, wherein A represents benzothiophene or dihydrobenzothiophene, which is optionally substituted (in addition to the substituents R and R') in the 2-position, substituted in the 5-position by $-NR'_aR''_a$ wherein $R'_a$ and $R''_a$ are as defined in claim 1, and substituted in the 3-position by $-(CH_2)_t-NHCOR'_a$ or $-(CH_2)_t-CONHR'_a$, wherein t is 2 or 3 and $R'_a$ is as defined in claim 1, its enantiomers and diastereoisomers, and addition salts thereof with a pharmaceutically acceptable acid or base.

20. A compound of claim 1 which is:
N-[2-(5-mercaptobenzo[b]furan-3-yl)ethyl]acetamide, or
N-[2-(2-benzyl-5-mercaptobenzo[b]furan-3-yl)ethyl]-1-cyclopropanecarboxamide,
its enantiomers and diastereoisomers, and addition salts thereof with a pharmaceutically acceptable acid or base.

21. A compound of claim 1 which is:
N-{2-[5-(2-pyridylthio)benzo[b]furan-3-yl]ethyl}acetamide,
N-{[2-benzyl-5-(3-butenylthio)benzo[b]thiophen-3-yl]methyl}acetamide,
N-{2-[5-(allylthio)-2-benzylbenzo[b]furan-3-yl]ethyl}-1-cyclopropanecarboxamide,
N-{2-[5-(propylthio)-2-phenylbenzo[b]thiophen-3-yl]ethyl}acetamide,
N-{2-[5-(isopentylthio)benzo[b]thiophen-3-yl]ethyl}acrylamide, or N-{[2-(2-furylmethyl)-5-(2-propynylthio)benzo[b]furan-3-yl]methyl}acetamide, its enantiomers and diastereoisomers, and addition salts thereof with a pharmaceutically acceptable acid or base.

22. A compound of formula $(XX_A)$:

$$Hal\text{-}A_A\text{-}R'_A \qquad (XX_A)$$

wherein:

Hal represents halogen (fluorine, chlorine, bromine, iodine), $A_A$ represents:

a ring system of formula (a):

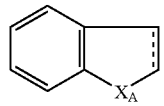

(a)

wherein $X_A$ represents sulphur and the symbol ----- is as defined hereinbefore, wherein the halogen atom substitutes the benzene nucleus and R'A substitutes the 5-membered ring, which ring systems of formula (a) may be substituted (in addition to the halogen atom and the group $R'_A$) by one or more groups selected from $R_a$, $COR_a$, $COOR_a$, $OCOR_a$ wherein $R_a$ is as defined hereinbefore, and $R'_A$ represents $G\text{-}R^2_A$ wherein G is as defined hereinbefore and $R^2_A$ represents

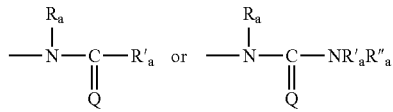

wherein $R_a$, $R'_a$, $R''_a$ and Q are as defined hereinbefore, its enantiomers and diastereoisomers, and addition salts thereof with a pharmaceutically acceptable acid or base, as synthesis intermediates but also as compounds for use in the treatment of disorders associated with the melatoninergic system.

23. A method for treating a living animal body, including a human, afflicted with disorders of the melatoninergic system, comprising the step of administering to the living animal body, including a human, an amount of a compound of claim 1, which is effective for the alleviation of the condition.

24. A pharmaceutical composition comprising, as active principle, an effective amount of a compound of claim 1, together with one or more pharmaceutically acceptable excipients or vehicles.

* * * * *

UNITED STATES PATENT AND TRADEMARK OFFICE
CERTIFICATE OF CORRECTION

PATENT NO. : 7,126,012 B2  
APPLICATION NO. : 10/947757  
DATED : October 24, 2006  
INVENTOR(S) : Daniel Lesieur et al.

Page 1 of 1

It is certified that error appears in the above-identified patent and that said Letters Patent is hereby corrected as shown below:

Cover Page, References Cited: "8,605,632" should be --6,605,632--.

Cover Page, Item (57) Abstract: "-$(CH^2)t-R^5$" should be -- -$(CH_2)t-R^5$--.

Cover Page, Formula (VII):

$$\begin{array}{c} | \\ -S-R^4 \\ | \\ (O)_o \end{array} \quad (VII)$$

should be $$-- \begin{array}{c} | \\ -S-R^4 \\ | \\ (O)_v \end{array} \quad (VII) \; --$$

Signed and Sealed this

Tenth Day of April, 2007

JON W. DUDAS  
*Director of the United States Patent and Trademark Office*